(12) United States Patent
Dimarchi et al.

(10) Patent No.: US 8,981,047 B2
(45) Date of Patent: Mar. 17, 2015

(54) GLUCAGON ANTAGONISTS

(75) Inventors: Richard D. Dimarchi, Carmel, IN (US); Bin Yang, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 910 days.

(21) Appl. No.: 12/739,342

(22) PCT Filed: Oct. 23, 2008

(86) PCT No.: PCT/US2008/080973
§ 371 (c)(1),
(2), (4) Date: Apr. 22, 2010

(87) PCT Pub. No.: WO2009/058662
PCT Pub. Date: May 7, 2009

(65) Prior Publication Data
US 2012/0122783 A1 May 17, 2012

Related U.S. Application Data

(60) Provisional application No. 60/983,783, filed on Oct. 30, 2007.

(51) Int. Cl.
*A61K 38/26* (2006.01)
*C07K 14/605* (2006.01)
*C07K 14/00* (2006.01)
*A61K 38/00* (2006.01)

(52) U.S. Cl.
CPC ............... *C07K 14/605* (2013.01); *A61K 38/00* (2013.01)
USPC ............................ 530/308; 530/324; 530/325

(58) Field of Classification Search
None
See application file for complete search history.

(56) References Cited

U.S. PATENT DOCUMENTS

| | | | |
|---|---|---|---|
| 4,275,152 A | 6/1981 | Esders et al. | |
| 5,359,030 A | 10/1994 | Ekwuribe | |
| 5,510,459 A | 4/1996 | Smith et al. | |
| 5,512,549 A | 4/1996 | Chen et al. | |
| 5,665,705 A | 9/1997 | Merrifield et al. | |
| 5,783,674 A | 7/1998 | Geysen | |
| 6,191,102 B1 | 2/2001 | DiMarchi et al. | |
| 6,583,111 B1 | 6/2003 | DiMarchi et al. | |
| 6,677,136 B2 * | 1/2004 | Marshall et al. | 435/69.1 |
| 7,192,922 B2 | 3/2007 | Shannon et al. | |
| 7,211,557 B2 | 5/2007 | DiMarchi et al. | |
| 7,576,059 B2 | 8/2009 | Jonassen et al. | |
| 2003/0021795 A1 | 1/2003 | Houston et al. | |
| 2003/0032588 A1 * | 2/2003 | Marshall et al. | 514/12 |
| 2003/0143183 A1 | 7/2003 | Knudsen et al. | |
| 2003/0204063 A1 | 10/2003 | Gravel et al. | |
| 2004/0002468 A1 | 1/2004 | Wadsworth et al. | |
| 2004/0235710 A1 | 11/2004 | DeFilippis et al. | |
| 2005/0070469 A1 | 3/2005 | Bloom et al. | |
| 2005/0095679 A1 | 5/2005 | Prescott et al. | |
| 2005/0124550 A1 | 6/2005 | Peri | |
| 2005/0153890 A1 | 7/2005 | Pan et al. | |
| 2005/0288248 A1 | 12/2005 | Pan et al. | |
| 2006/0003417 A1 | 1/2006 | Pan et al. | |
| 2006/0003935 A1 | 1/2006 | Pan et al. | |
| 2006/0171920 A1 | 8/2006 | Shechter et al. | |
| 2006/0210534 A1 | 9/2006 | Lee et al. | |
| 2006/0252916 A1 | 11/2006 | DiMarchi et al. | |
| 2006/0286129 A1 | 12/2006 | Sarubbi | |
| 2007/0042956 A1 | 2/2007 | Johansen et al. | |
| 2007/0173452 A1 | 7/2007 | DiMarchi et al. | |
| 2007/0203058 A1 | 8/2007 | Lau et al. | |
| 2007/0275900 A1 * | 11/2007 | Balzarini | 514/14 |
| 2007/0287670 A1 | 12/2007 | Natarajan et al. | |
| 2008/0113905 A1 | 5/2008 | DiMarchi et al. | |
| 2008/0318837 A1 | 12/2008 | Quay et al. | |
| 2009/0036364 A1 | 2/2009 | Levy et al. | |
| 2009/0054305 A1 | 2/2009 | Schlein et al. | |
| 2009/0062192 A1 | 3/2009 | Christensen et al. | |
| 2009/0074769 A1 | 3/2009 | Glaesner et al. | |
| 2009/0125574 A1 | 5/2009 | Sheffer et al. | |

(Continued)

FOREIGN PATENT DOCUMENTS

| | | |
|---|---|---|
| CA | 2024855 | 3/1992 |
| EP | 0220958 | 5/1987 |

(Continued)

OTHER PUBLICATIONS

Azizeh et al., "The Role of Phenylalanine at Position 6 in Glucagon's Mechanism of Biological Action: Multiple Replacement Analogues of Glucagon", J. Med. Chem., 1997, pp. 2555-2562.*

(Continued)

*Primary Examiner* — Karlheinz R Skowronek
*Assistant Examiner* — Lianko Garyu
(74) *Attorney, Agent, or Firm* — Barnes & Thornburg LLP

(57) ABSTRACT

Glucagon antagonists are provided which comprise amino acid substitutions and/or chemical modifications to glucagon sequence. In one embodiment, the glucagon antagonists comprise a native glucagon peptide that has been modified by the deletion of the first two to five amino acid residues from the N-terminus and (i) an amino acid substitution at position 9 (according to the numbering of native glucagon) or (ii) substitution of the Phe at position 6 (according to the numbering of native glucagon) with phenyl lactic acid (PLA). In another embodiment, the glucagon antagonists comprise the structure A-B-C as described herein, wherein A is PLA, an oxy derivative thereof, or a peptide of 2-6 amino acids in which two consecutive amino acids of the peptide are linked via an ester or ether bond.

23 Claims, 9 Drawing Sheets

(56) References Cited

U.S. PATENT DOCUMENTS

| | | |
|---|---|---|
| 2009/0137456 A1 | 5/2009 | DiMarchi et al. |
| 2009/0192072 A1 | 7/2009 | Pillutla et al. |
| 2010/0190699 A1 | 7/2010 | DiMarchi et al. |
| 2010/0190701 A1* | 7/2010 | Day et al. ................. 514/12 |
| 2011/0065633 A1 | 3/2011 | DiMarchi et al. |
| 2011/0098217 A1 | 4/2011 | DiMarchi et al. |
| 2011/0166062 A1 | 7/2011 | DiMarchi et al. |
| 2011/0190200 A1 | 8/2011 | DiMarchi et al. |
| 2011/0257092 A1 | 10/2011 | DiMarchi et al. |
| 2011/0288003 A1 | 11/2011 | DiMarchi et al. |

FOREIGN PATENT DOCUMENTS

| | | |
|---|---|---|
| EP | 0479210 | 4/1992 |
| EP | 0815135 | 9/1996 |
| EP | 1695983 B1 | 8/2006 |
| EP | 2036539 A1 | 3/2009 |
| EP | 2036923 A1 | 3/2009 |
| EP | 2398483 | 8/2010 |
| EP | 2300035 | 1/2012 |
| WO | WO96/29342 | 9/1996 |
| WO | WO 9707814 | 3/1997 |
| WO | 97/29180 | 8/1997 |
| WO | 98/11126 | 3/1998 |
| WO | 98/19698 | 5/1998 |
| WO | WO 9824464 | 6/1998 |
| WO | WO 9946283 | 9/1999 |
| WO | WO 0020592 | 4/2000 |
| WO | WO00/042026 | 7/2000 |
| WO | WO 0058360 | 10/2000 |
| WO | 01/83527 A2 | 11/2001 |
| WO | WO 0181919 | 11/2001 |
| WO | 01/98331 | 12/2001 |
| WO | WO 0210195 | 2/2002 |
| WO | WO0213801 | 2/2002 |
| WO | 02/48183 | 6/2002 |
| WO | WO 02100390 | 12/2002 |
| WO | WO03/011892 | 2/2003 |
| WO | 03/020201 | 3/2003 |
| WO | WO03022304 | 3/2003 |
| WO | WO 03026635 | 4/2003 |
| WO | 03/035099 | 5/2003 |
| WO | WO 03082898 | 10/2003 |
| WO | 03/103572 | 12/2003 |
| WO | WO 03103697 | 12/2003 |
| WO | WO 03105760 | 12/2003 |
| WO | WO2004000354 | 12/2003 |
| WO | 2004/022004 | 3/2004 |
| WO | 2004/067548 | 8/2004 |
| WO | WO 2004078777 | 9/2004 |
| WO | 2004/093823 | 11/2004 |
| WO | 2004/105781 | 12/2004 |
| WO | 2004/105790 | 12/2004 |
| WO | WO 2004103390 | 12/2004 |
| WO | WO 2005082928 | 9/2005 |
| WO | WO 2006086769 | 8/2006 |
| WO | WO 2006121904 | 11/2006 |
| WO | WO2006124529 | 11/2006 |
| WO | WO2006134340 A2 | 12/2006 |
| WO | 2007/022123 | 2/2007 |
| WO | WO 2007028632 | 3/2007 |
| WO | WO2007028633 | 3/2007 |
| WO | 2007/056362 A2 | 5/2007 |
| WO | 2007/100535 | 9/2007 |
| WO | WO 2007109354 | 9/2007 |
| WO | WO 2008021560 | 2/2008 |
| WO | WO 2008022015 | 2/2008 |
| WO | WO2008023050 | 2/2008 |
| WO | WO 2008076933 | 6/2008 |
| WO | 2008/086086 | 7/2008 |
| WO | 2008/101017 | 8/2008 |
| WO | WO 2008101017 A2 * | 8/2008 |
| WO | WO2009030738 A1 | 3/2009 |
| WO | WO2009030774 A1 | 3/2009 |
| WO | WO2009034117 A1 | 3/2009 |
| WO | WO2009034118 A1 | 3/2009 |
| WO | WO2009034119 A1 | 3/2009 |
| WO | WO2009035540 A2 | 3/2009 |
| WO | 2009/058662 | 5/2009 |
| WO | 2009/058734 | 5/2009 |
| WO | WO 2009/058734 | 5/2009 |
| WO | 2009/095479 | 8/2009 |
| WO | WO/2009/099763 | 8/2009 |
| WO | 2009/155257 | 12/2009 |
| WO | 2009/155258 | 12/2009 |
| WO | 2010/011439 | 1/2010 |
| WO | 2010/071807 | 6/2010 |
| WO | 2010/080605 | 7/2010 |
| WO | 2010/096052 | 8/2010 |
| WO | 2010/148089 | 12/2010 |
| WO | 2011/075393 | 6/2011 |
| WO | WO 2011087671 | 7/2011 |
| WO | WO 2011087672 | 7/2011 |
| WO | 2011/094337 | 8/2011 |
| WO | WO2011119657 | 9/2011 |
| WO | WO2011143208 | 11/2011 |
| WO | WO2011143209 | 11/2011 |
| WO | WO2011163012 | 12/2011 |
| WO | WO2011163473 | 12/2011 |

OTHER PUBLICATIONS

De, et al., "Investigation of the feasibility of an amide-based prodrug under physiological conditions," Int. J. Pept. Res. Ther., 14, pp. 255-262 (2008).
Madsen, et al., "Structure-activity and protraction relationship of long-acting glucagon-like peptide-1 derivatives: Importance of fatty acid length, polarity, and bulkiness," J. Med. Chem., 50, pp. 6126-6132 (2007).
PCT International Search Report for PCT/US2011/041601 completed by the US Searching Authority on Nov. 10, 2011.
Yang, B., et al "Synthesis and Biological Assessment of Sulfonic Acid-Based Glucagon Analogs" Biopolymers, vol. 80, No. 4, 2005, p. 545.
Extended EP Search Report completed by the EP Searching Authority on 06APR11 in connection with EP Patent Application No. 08845852.6.
Database EMBL, Jul. 16, 2007, Richard DiMarchi and David Smiley, "Human Glucagon Peptide Seq ID No. 1" XP002631582, retrieved from EBI, Database Accession No. AGB07042, Abstract.
Evans et al., "Effect of β-Endorphin C-Terminal Peptides on Glucose Uptake in Isolated Skeletal Muscles of the Mouse," Peptides, vol. 18, No. 1, pp. 165-167, (1997).
Hansen et al., "Incretin hormones and insulin sensitivity," Trends in Endocrinology and Metabolism, vol. 16, No. 4, May/Jun. 2005, pp. 135-136.
"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.
Ahn, J.M. et al., A new approach to search for the bioactive conformation of glucagon: positional cyclization scanning, J. Med. Chem., 44(19): 3109-16, Sep. 13, 2001.
Ahn, J.M. et al., Development of potent truncated glucagon antagonists, J. Med. Chem., 44(9): 1372-9, Apr. 26, 2001.
Chabenne et al., Optimization of the native glucagon sequence for medicinal purposes, J. Diabetes. Sci. Technol., 4(6): 1322-31, Nov. 1, 2010.
Day et al., Charge inversion at position 68 of the glucagon and glucagon-like peptide-1 receptors supports selectivity in hormone action. J. Pept. Sci., 17(3): 218-25, Nov. 30, 2010.
De, Design of peptide-based prodrug chemistry and its application to glucagon-like peptide 1. Masters Thesis Aug. 2007. [Retrieved from the Internet on Jun. 16, 2009: <https://scholarworksiu.edu/dspace/browse?value=De%2C+ArnabBtype=author>[; p. 8, para 2; p. 16, para 3; p. 40, para 1; p. 66, para 2; p. 77, para 1-2; p. 79, para 1.
Gelfanov, et al., Discover and Structural Optimization of High Affinity Co-Agonists at the Glucagon and GLP-1 Receptors, Understanding Biology Using Peptides, Springer, pp. 763-764, Jun. 23, 2005.

(56) References Cited

OTHER PUBLICATIONS

GenBank entry AAII05278. Jul. 15, 2006. [Retrieved from the Internet Jun. 18, 2009: ~http://www. ncbi. nim.n ih.gov/protein/13528972>].

Habegger et al., The metabolic actions of glucagon revisited, *Nat. Rev. Endocrinol.*, 6(12): 689-97, Oct. 19, 2010.

Harris, J. Milton, Final Word: PEGylation-A "Sunset" Technology? <http://licence.icopyright.net/user/viewFreeUse.act?fuid=OTU1NjY3OA%3D%3D>, BioPharm International, Jun. 1, 2004.

Heppner et al., Glucagon regulation of energy metabolism, *Physiol Behav.*, 100(5): 545-8, Apr. 8, 2010.

Hruby et al., "The Design and Biological Activities of Glucagon Agonists and Antagonists, and Their Use in Examining the Mechanisms of Glucose Action," *Curr. Med. Chem.-Imm., Endoc. & Metab. Agents*, 2001, 1, pp. 199-215.

Jonathan Day et al., "A New Glucagon and GLP-1 Co-Agonist Eliminates Obesity in Rodents," Nature Chemical Biology, vol. 5, No. 10, Oct. 2009, pp. 749-757.

Joshi et al, "Studies on the Mechanism of Aspartic Acid Cleavage and Glutamine Deamidation in the Acidic Degradation of Glucagon," *Journal of Pharmaceutical Sciences*, vol. 94, No. 9, Sep. 2005, pp. 1912-1927.

Joshi et al., "The Degradation Pathways of Glucagon in Acidic Solutions," *International Journal of Pharmaceutics*, 203 (2000), pp. 115-125.

Joshi et al., "The Estimation of Glutaminyl Deamidation and Aspartyl Cleavage Rates in Glucagon," *International Journal of Pharmaceutics*, 273 (2004), pp. 213-219.

Krstenansky et al., "Importance of the C-terminal α-helical structure for glucagon's biological activity," Int. J. Peptide Protein Res., 32, 1988, 468-475.

Lee et al., "Synthesis, Characterization, and Pharmacokinetic Studies of PEGylated Glucagon-like Peptide-1," *Bioconjugate Chem.*, 2005, vol. 16, No. 2, pp. 377-382.

Levy et al., Optimization of the C-terminal Sequence in Glucagon to Maximize Receptor Affinity, Poster Presentation, Jun. 19, 2005.

Levy et al., Optimization of the C-terminal Sequence in Glucagon to Maximize Receptor Affinity, *Understanding Biology Using Peptides*, American Peptide Society, Apr. 2006.

Li et al., Crystallization and preliminary X-ray analysis of anti-obesity peptide hormone oxyntomodulin, *Protein & Peptide Letters*, 15(2): 232-4 (2008).

Li et al., Design, synthesis and crystallization of a novel glucagon analog as a therapeutic agent, *Acta Crystallogr. Sect. F Siruct. Biol. Cryst. Commun.*, 63(Pt 7):599-601, Jun. 15, 2007.

Li et al., Structural Basis for Enhanced Solublity of a C-Terminally Extended Glucagon Analog , *Biopolymers.*, 96(4): 480 (2011).

M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.

Marita P. Feldkaemper et al., "Localization and Regulation of Glucagon Receptors in the Chick Eye and Preproglucagon and Glucagon Receptor Expression in the Mouse Eye," Experimental Eye Research, Academic Press Ltd., London, vol. 79, No. 3, Sep. 1, 2004, pp. 321-329.

McKee et al., Receptor Binding and Adenylate Cyclase Activities of Glucagon Analogues Modified in the N-Terminal Region, Biochemistry, 25: 1650-6 (1986).

Nogueiras et al., Direct control of peripheral lipid deposition by CNS GLP-1 receptor signaling is mediated by the sympathetic nervous system and blunted in diet-induced obesity, J. Neurosci., 29(18): 5916-25, May 6, 2009.

Ouyang et al., Discovery of Bi-Functional Peptides Balanced in Glucagon Antagonism & GLP-1 Agonism. A Search for the Molecular Basis in the Inversion of Activity at Homologous Receptors, 71st Scientific sessions of American Diabetes Association 2011—Post-Conference Review and Analysis.

Patterson et al., A novel human-based receptor antagonist of sustained action reveals body weight control by endogenous GLP-1, *ACS Chem Biol.*, 6(2): 135-45 Nov. 4, 2010.

Patterson et al., Functional association of the N-terminal residues with the central region in glucagon-related peptides, *J. Peptide Sci.*, First published online Jun. 10, 2011.

PCT International Search Report for PCT/US2008/050099 completed by the US Searching Authority on Sep. 1, 2008.

PCT International Search Report for PCT/US2008/053857 completed by the US Searching Authority on Sep. 16, 2008.

PCT International Search Report for PCT/US2008/081333 completed by the US Searching Authority on Mar. 12, 2009.

PCT International Search Report for PCT/US2009/031593 completed by the US Searching Authority on Jun. 18, 2009.

Robberecht, P. et al., "Receptor Occupancy and Adenylate Cyclase Activation in Rat Liver and Heart Membranes by 10 Glucagon Analogs Modified in Position 2, 3, 4, 25, 27 and/or 29," Regulatory Peptides, 21 (1988), 117-128.

Sapse et al., The Role of Sale Bridge Formation in Glucagon: An Experimental and Theoretical Study of Glucagon Analogs and Peptide Fragments of Glucagon, *Molec. Med.*, 8(5): 251-62, May 1, 2002.

Stigsnaes et al., "Characterisation and Physical Stability of PEGylated Glucagon," *International Journal of Pharmaceutics*, 330 (2007), pp. 87-98.

Traylor et al., Identification of the High Potency Glucagon Agonist with Enhanced Biophysical Stability and Aqueous Solubility, Poster Abstract PY 10, pp. 505-506, Jun. 10, 2005.

Trivedi, D. et al., Design and synthesis of conformationally constrained glucagon analogues, *J. Med. Chem.*, 43(9): 1714-22, May 4, 2000 (Abstract).

Tschoep et al., A Novel Glucagon/GLP-1 Co-Agonist Eliminates Obesity in Rodents, Diabetes, 58 (Supp. 1): A83 (2009).

Unson et al., "Glucagon antagonists: Contribution to binding and activity of the amino-terminal sequence 1-5, position 12 and the putative alpha-helical segment 19-27," J. Biol. Chem. v264, pp. 789-794, Jan. 15, 1989, p. 792, para 1, Table 1.

Unson et al., Positively Charged Residues at Positions 12, 17, and 18 of Glucagon Ensure Maximum Biological Potency, *J. Biol. Chem.*, 273(17): 10308-12 (1998).

Ward et al., In vitro and in vivo evaluation of native glucagon and glucagon analog (MAR-D28) during aging: lack of cytotoxicity and preservation of hyperglycemic effect, J. Diabetes Sci. Technol., 4(6):1311-21, Nov. 1, 2010.

Wynne et al., "Subcutaneous Oxyntomodulin Reduces Body Weight in Overweight and Obese Subjects," *Diabetes*, vol. 54, Aug. 2005, pp. 2390-2395.

Ziiang et al., Design and synthesis of novel GLP1 analogues with significantly prolonged time action, Biopolymers., 80(4): 555 (2005).

Azizeh et al., "Topographical amino acid substitution in position 10 of glucagon leads to antagonists/partial agonists with greater binding differences," J. Med. Chem., vol. 39, No. 13, Jun. 21, 1996, pp. 2449-2455.

Azizeh et al., "Pure glucagon antagonists: biological activities and cAMP accumulation using phosphodiesterase inhibitors," Peptides 1997, vol. 18, No. 5, pp. 633-641.

Phillips et al., "Supramolecular Protein Engineering: Design of Zinc-Stapled Insulin Hexamers as a Long Acting Depot," J. Biol. Chem., vol. 285, No. 16, Apr. 16, 2010, pp. 11755-11759.

Murphy, et al., "Potent Long-Acting Alkylated Analogs of Growth Hormone-Releasing Factor," Pept. Res., vol. 1. No. 1, pp. 36-41 (1988).

Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," J. Biochem., 362 (2002), pp. 389-394.

Gysin ct al., "Design and Synthesis of Glucagon Partial Agonists and Antagonists," Biochemistry, 25, (1986), pp. 8278-8284.

PCT International Search Report for PCT/US2009/047437 completed by the US Searching Authority on Nov. 3, 2009.

(56) References Cited

OTHER PUBLICATIONS

Supplemental European Search Report issued in connection with EP Application No. 09767567.2 issued on Jun. 17, 2011.
Day, J.; Patterson, J.; Gelfanov, V. and DiMarchi, Richard Molecular-basis for Specificity in Biological Action at the Homologous Glucagon and GLP-1 Receptors, (2009) Proceedings of the 21$^{st}$ American Peptide Society 142-143.
De, A. and DiMarchi, R. Synthesis & Analysis of Peptide Hormone-based prodrugs, (2009) Proceedings of the 21st American Peptide Society 160-161.
De, Arnab; DiMarchi, Richard D. Investigation of the feasibility of an amide-based prodrug under physiological conditions. International Journal of Peptide Research and Therapeutics (2008), 14(4), 393.
De, et al., "Investigation of the feasibily of an amide-based prodrug under physiological conditions," Int. J. Pept. Res. Then, 14, pp. 255-262 (2008).
De, A. and DiMarchi, R. Synthesis & Characterization of Ester-Based Prodrugs of Glucagon-Like Peptide 1, Peptide Science (2010) 94(4) 448-456.
DiMarchi, Richard, "The Use of Bioproducts in the Treatments of Metabolic Diseases" presentation slides for the Keystone Symposia (Jan. 25, 2009, Banff, Alberta);.
Finan, B.; Gelfanov, V. and DiMarchi, R. Assessment of a Tat-Derived Peptide as a Vector for Hormonal Transport, (2009) Proceedings of the 21st American Peptide Society 321-322.
Kukuch, A.; Patterson, J.; DiMarchi, R. and Tolbert, T Immunoglobulin Fc-based Peptide Fusion Proteins as a Basis for Optimizing In Vivo Pharmacology, (2009) Proceedings of the 21$^{st}$ American Peptide Society 177-178.
Ma, T.; Day, J.; Gelfanov, V. and DiMarchi, R. Discovery and Structural Optimization of High Affinity Co-Agonists at the Glucagon and GLP-1 Receptors, (2009) Proceedings of the 21$^{st}$ American Peptide Society 146-147.
Ouyang et al., "Synthesis and Characterization of Peptides with Glucagon Antagonism and GLP-1 Agonism," poster presentation at the 21$^{st}$ American Peptide Symposium (Jun. 7-12, 2009, Bloomington, IN).
Tschoep et al., "A Novel Glucagon/GLP-1 Co-Agonist Eliminates Obesity in Rodents," American Diabetes Association Abstract No. 313-OR (2009).
Tschoep, Matthias, "A Novel Glucagon/GLP-1 Co-Agonist Eliminates Obesity in Rodents" presentation slides for the 2009 American Diabetes Association meeting (Jun. 5-9, 2009, New Orleans, LA).
Tschoep, Matthias, "Afferent Gut Hormones in the Control of Energy Balance and Metabolism" presentation slides for the 21st American Peptide Symposium (Jun. 7-12, 2009, Bloomington, IN).
Ward, B.; Finan, B.; Gelfanov, V. and DiMarchi, R. Exploring the N-terminal Hydrophobic Faces of Glucagon and Glucagon-like Peptide-1, (2009) Proceedings of the 21$^{st}$ American Peptide Society 153-154.
Yang, B. and DiMarchi, R.D. (2005). A Novel Approach to Resin-based Cysteine Alkylation Peptides: Chemistry, Structure and Biology, Proceedings of the XIX American Peptide Symposium, (88-89).
Irwin et al., "Early administration of the glucose-dependent insulinotropic polypeptide receptor antagonist (Pro$^3$) GIP prevents the development of diabetes and related metabolic abnormalities associated with genetically inherited obesity in ob/ob mice," Diabetologia 50:1532-1540 (2007).
Kulkarni, "GIP: No Longer the Neglected Incretin Twin?," Science Translational Medicine 2(49): p. 47, Sep. 15, 2010.
Montrose-Rafizadeh et al., "High Potency Antagonists of the Pancreatic Glucagon-like Peptide-1 Receptor," Journal of Biological Chemistry, 272(34) 21201-21206 (1997).
Sturm et al., "Structure-Function Studies on Positions 17, 18, and 21 Replacement Analogues of Glucagon: The Importance of Charged Residues and Salt Bridges in Glucagon Biological Activity," J Med Chem 1998, 41, 2693-2700.
Habi et al., Peptide Science, vol. 80, Issue 4, pp. 608 and 579 (abstracts only), 2005.

Habi, "Special Issue: Program and Abstracts for the 19th American Peptide Symposium, 2005, Abstracts of Poster Section C," (pp. 574-603) Article first published online: Jun. 10, 2005 | DOI: 10.1002/bip. 20325.
Blache et al., "Development of an oxyntomodulin/glicentin C-terminal radioimmunoassay using a "thiol-maleoyl" coupling method for preparing the immunogen," Anal Biochem 1988 173(1):151-159 (1988), abstract only.
Vijayalakshmi et al., "Comparison of Helix-Stabilizing Effects of α, α-dialkyl Glycines with Linear and Cycloalkyl Side Chains", Biopolymers 53: 84-98 (Jan. 21, 2000).
Andrews et al., "Forming Stable Helical Peptides Using Natural and Artificial Amino Acids", Tetrahedron 55: 11711-11743, (1999).
Battersby et al., "Diketopiperazine Formation and N-Terminal Degradation in Recombinant Human Growth Hormone", International Journal of Peptide & Protein Research 44: 215-222, (1994).
Eriksson et al., "hPEPT1 Affinity and Translocation of Selected Gln-Sar and Glu-Sar Dipeptide Derivatives", Molecular Pharmaceutics vol. 2, No. 3: 242-249 (May 10, 2005).
Garcia-Aparicio et al., "Design and Discovery of a Novel Dipeptidyl-peptidase IV (CD26)-Based Prodrug Approach", J. Med. Chem. 49: 5339-5351 (2006).
Goolcharran et al., "Comparison of the Rates of Deamidation, Diketopiperazine Formation, and Oxidation in Recombinant Human Vascular Endothelial Growth Factor and Model Peptides", AAPS Pharmsci 2000 2(1) article 5: 1-6 (Mar. 17, 2000).
Santos et al., Cyclization-Activated Prodrugs. Synthesis, Reactivity and Toxicity of Dipeptide Esters of Paracetamol, Bioorganic & Medicinal Chemistry Letters 15: 1595-1598 (2005).
Schafmeister et al., "An All-Hydrocarbon Cross-Linking System for Enhancing the Helicity and Metaboli Stability of Peptides", J. Am. Chem. Soc. 122: 5891-5892 (2000).
Walensky et al., "Activation of Apoptosis in Vivo by a Hydrocarbon-Stapled BH3 Helix", Science 205: 1466-1470 (Sep. 3, 2004).
Lebl, Michal, "Peptides: Breaking Away: The Proceedings of the Twenty-First American Peptide Symposium", Prompt Scientific Publishing (2009).
"Legacy Products—'Back to the Future'," presentation to Eli Lilly and Co., Sep. 22, 2005.
"Application of Chemical Biotechnology to Optimization of Endocrine Hormones," Carothers Lecture, Mar. 22, 2007.
"The Emergence of Chemical Biotechnology & Its Application to Optimization of Endocrine Hormones," UMBC presentation, Mar. 26, 2008.
"Emergence of Chemical Biotechnology," Eli Lilly and Co. presentation, Jun. 22, 2009.
"Novel Glucagon-Like Chimera Peptides—Virtues of Combinatorial Pharmacology," Keystone Conference, Apr. 12-17, 2010, Whistler, B.C.
"Novel Glucagon-Like Chimera Peptides—Virtues of Combinatorial Pharmacology," AAPS May 2010.
"Two for the Money" Gut Hormone Hybrids, Tschoep, ADA meeting, Jun. 25-29, 2010, Orlando, FL.
"Biotechnology—A Basis for Better Health & Economic Prosperity," Ohio State University presentation, Aug. 28, 2010.
"Novel Glucagon-Based Peptides—Virtues of Combinatorial Pharmacology," European Peptide Symposium, Sep. 5-9, 2010, Copenhagen, Denmark.
"Biotechnology—A Basis for Better Health & Economic Prosperity," Indiana University television presentation, Nov. 2010.
"Novel Glucagon-Based Peptides—Virtues of Combinatorial Pharmacology," University of Michigan, Oct. 13, 2010.
"Novel Glucagon-Based Peptides—Virtues of Combinatorial Pharmacology," Yale University, May 13, 2011.
"Speaking From the Gut: From Gastrointestinal Hormones to Combinatorial Therapies," Presentation to American Diabetes Association, Jun. 25, 2011.
"The Pursuit of Transformational Medicines," presentation to American Peptide Symposium, Jun. 25-30, 2011, San Diego, CA.
"The Pursuit of Transformational Medicines," NP2D presentation, Dec. 4, 2011.
"The Pursuit of Transformational Medicines," Keystone presentation, Jan. 29-Feb. 3, 2012, Santa Fe, NM.

(56) References Cited

OTHER PUBLICATIONS

"Novel Glucagon Peptides That Demonstrate the Virtues of Combinatorial Pharmacology," University of Toledo, Mar. 22, 2012.
Althage et al.,JBC "Targeted Ablation of GIP-Producing Cells in Transgenic mice reduces obesity and insulin resistance induced by a high fat diet" 2008).
Chia et al., "Exogenous glucose-dependent insulinotropic polypeptide worsens post-prandial hyperglycemia in type 2 diabetes," Diabetes, 58: 1342-1349 (2009).
Drucker, "Glucagon Gene Expression in Vertebrate Brain," The Journal of Biological Chemistry, vol. 263, No. 27, pp. 13475-13478, 1988.
Drucker, "The biology of incretin hormones," Cell Metabolism 3:153-165 (2006).
PCT International Search Report for PCT/US2009/034448 completed by the US Searching Authority on Jun. 4, 2010.
PCT International Search Report for PCT/US2009/068678 completed by the US Searching Authority on May 5, 2010.
Pan et al., "Synthesis of Cetuximab-Immunoliposomes via a Cholesterol-Based Membrane Anchor for Targeting of EGFR," Bioconjugate Chem., 18, pp. 101-108, 2007.
PCT International Search Report for PCT/US2009/047447 completed by the US Searching Authority on Mar. 19, 2010.
Collie et al., "Purification and sequence of rat oxyntomodulin," Proc. Natl. Acad. Sci. USA, vol. 91, pp. 9362-9366, Sep. 1994.
Sueiras-Diaz et al., "Structure-Activity Studies on the N-Terminal Region of Glucagon," J. Med. Chem., 27, pp. 310-315, 1984.
Hjorth et al., "glucagon and Glucagon-like Peptide 1: Selective Receptor Recognition via Distinct Peptide Epitopes," The Journal of Biological Chemistry, vol. 269, No. 48, pp. 30121-30124, Dec. 2, 1994.
Unson et al., "Role of Histidine-1 in Glucagon Action," Archives of Biochemistry and Biophysics, vol. 300, No. 2, pp. 747-750, Feb. 1, 1993.
Sato, H., "Enzymatic procedure for site-specific pegylation of proteins," Advanced Drug Delivery Reviews 54, pp. 487-504 (2002).
"Novel Glucagon-Like Chimera Peptides—Virtues of Combinatorial Pharmacology," University of Cincinnati, Jun. 2010.
"Molecular Miracles," Indiana University, Apr. 13, 2011.
"Novel Glucagon-Based Peptides—Virtues of Combinatorial Pharmacology," Aug. 31, 2011, Berlin.
Ward, "Fatty Acid Acylation of Peptides: Developing strategies to enhance medicines for treating metabolic disorders," Jan. 14, 2009.
DiMarchi, "Peptides—Development of Prodrug Chemistry," RBF Symposium Feb. 1-4, 2011 India.
Tschoep, "CNS Integration of Systems Metabolism: Target Opportunities for Diabetes Prevention and Therapy," RBF Symposium Feb. 1-4, 2011 India.
Yang et al., "Synthesis and Biological Assessment of Sulfonic Acid-Based Glucagon Antagonists," American Peptide Society, 2005.
Yang et al., "Synthesis and Biological Assessment of Sulfonic Acid-Based Glucagon Antagonists," poster presentation to American Peptide Society, 2005.
Yang et al., "A Novel Approach to Resin-Based Cysteine Alkylation," poster presentation to American Peptide Society, 2005.
PCT International Search Report for PCT/US2010/038825 completed by the US Searching Authority on Sep. 15, 2010.
PCT International Search Report for PCT/US2010/059724 completed by the US Searching Authority on Jun. 14, 2011.
Wibowo, "Synthesis, Purification, and Biological Activity of AIB Substituted Glucagon and GLP-1 Peptide Analogues," Project Report, Apr. 21, 2006.
PCT International Search Report for PCT/US2008/080973 completed by the US Searching Authority on Jun. 6, 2009.
Pan, et al. "Design of a Long Acting Peptide Functioning as Both a Glucagon-like Peptide-1 Receptor Agonist and a Glucagon Receptor Agonist" J. Biol. Chem.: May 5, 2006; vol. 281, No. 18; pp. 12506-12515. Table 1.

* cited by examiner

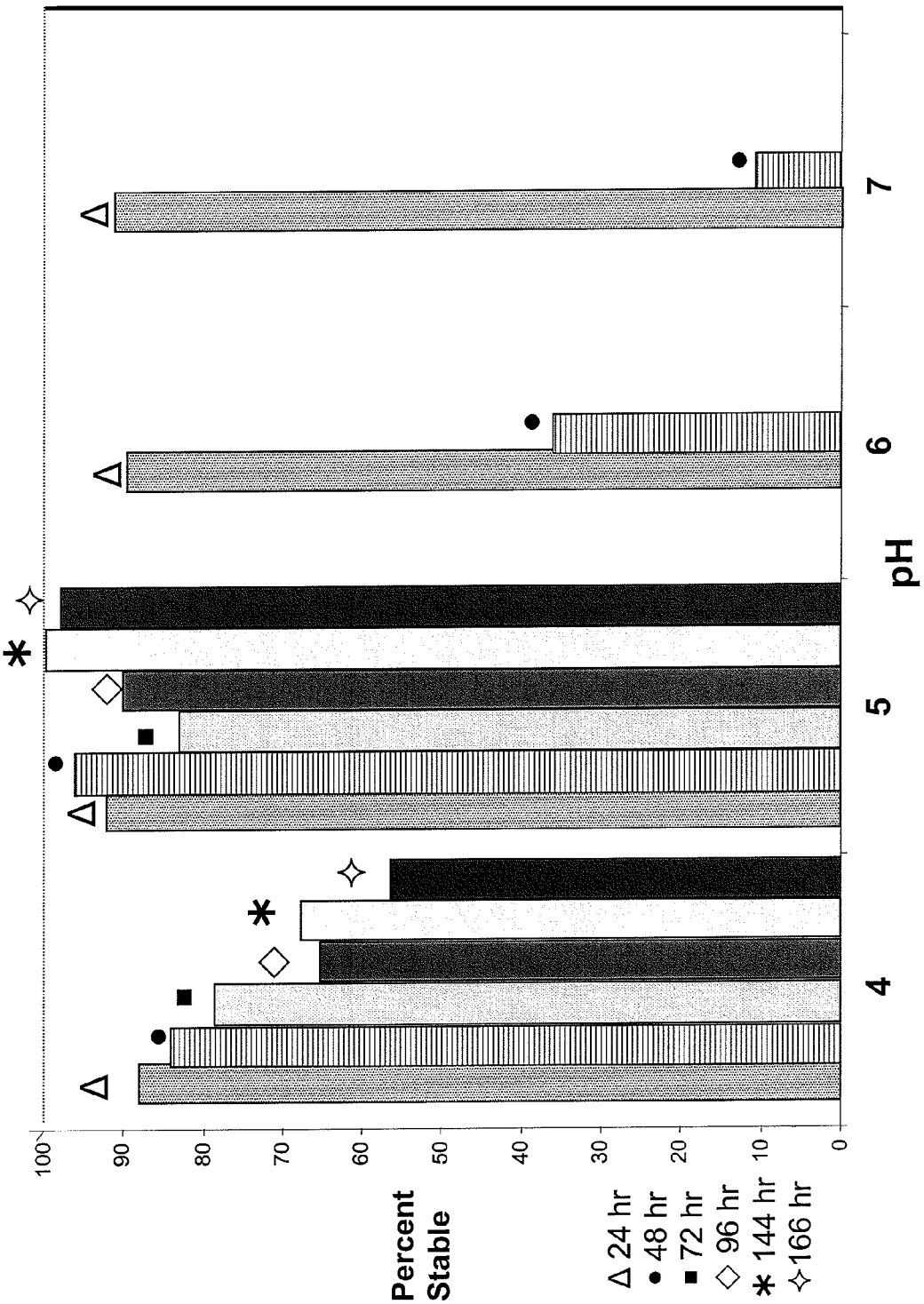

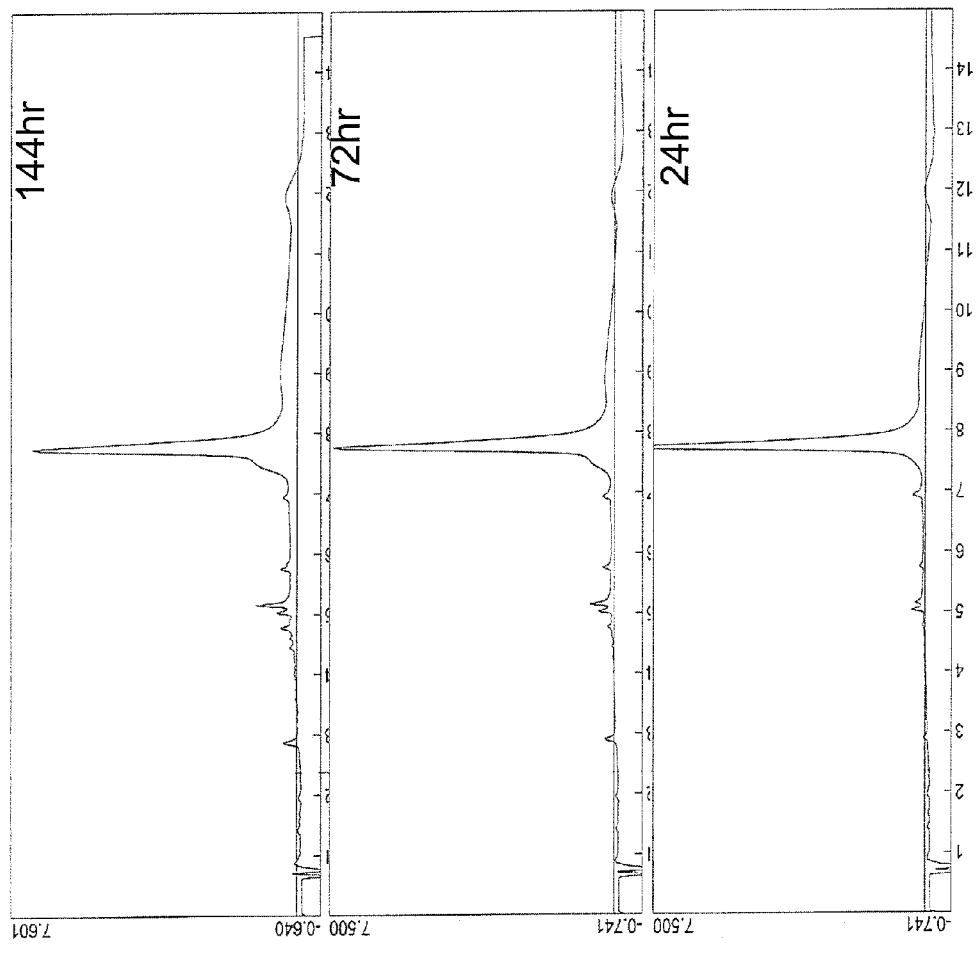
Fig. 2: HPLC Analysis of Glucagon Cys²¹-maleimidoPEG₅ₖ at pH 5 (37°C)

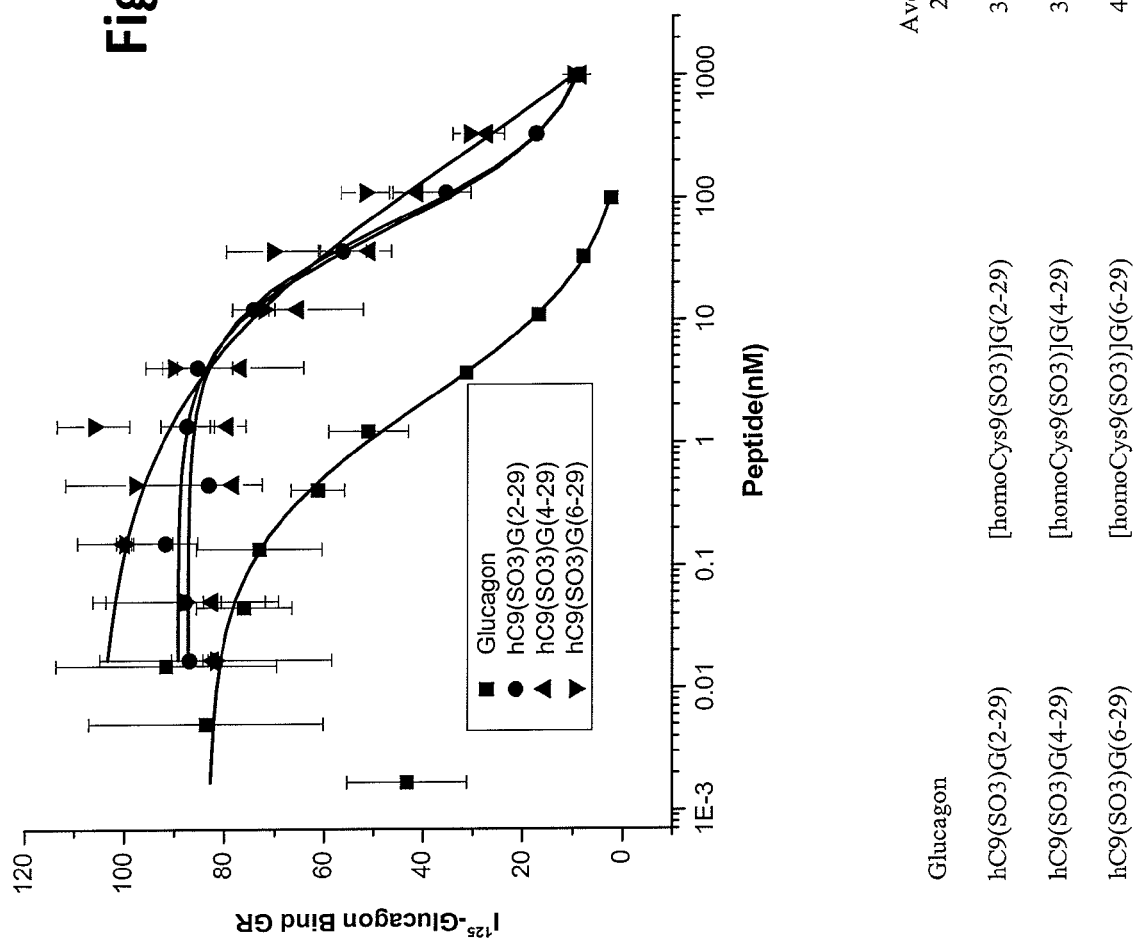

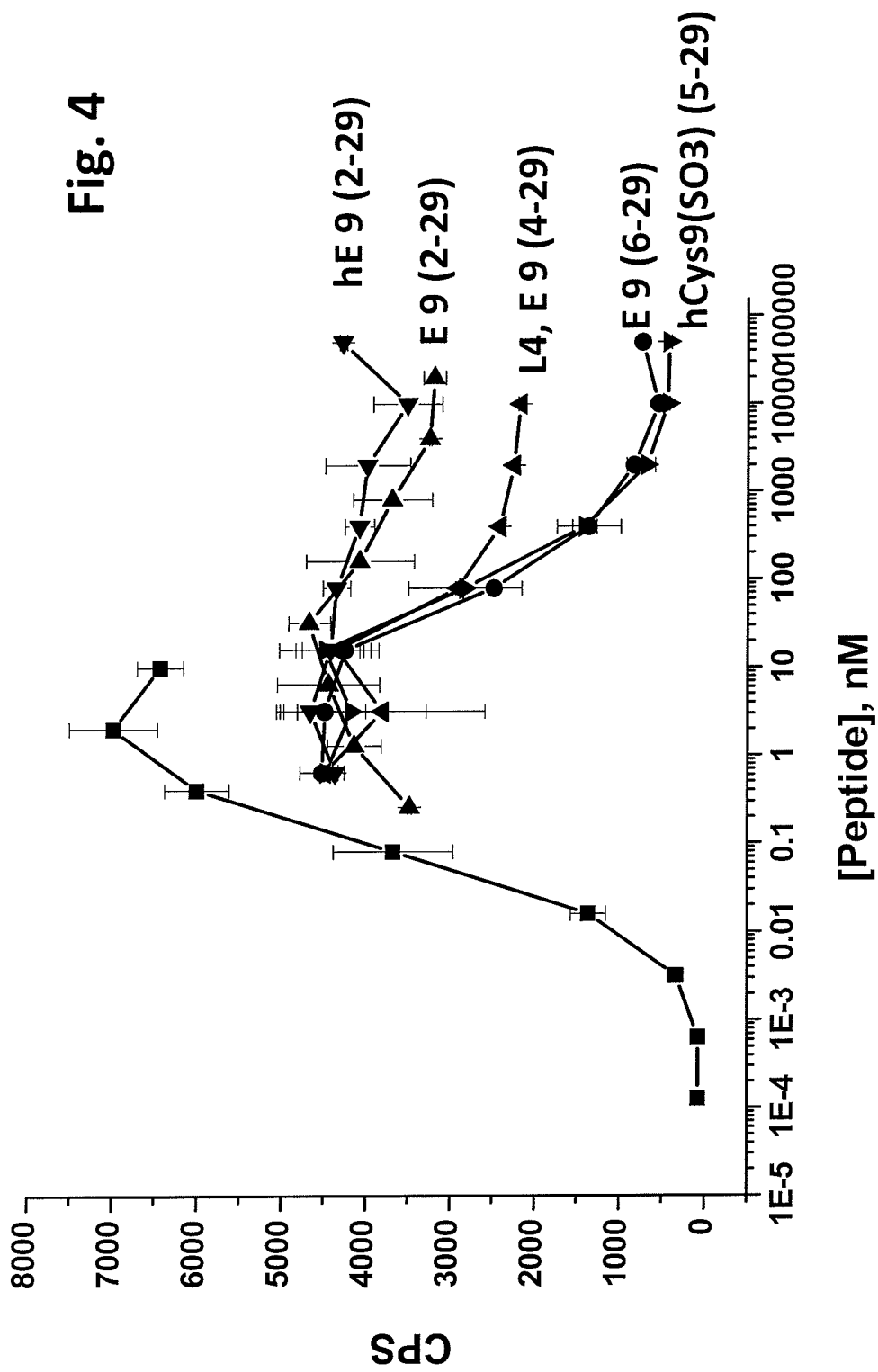

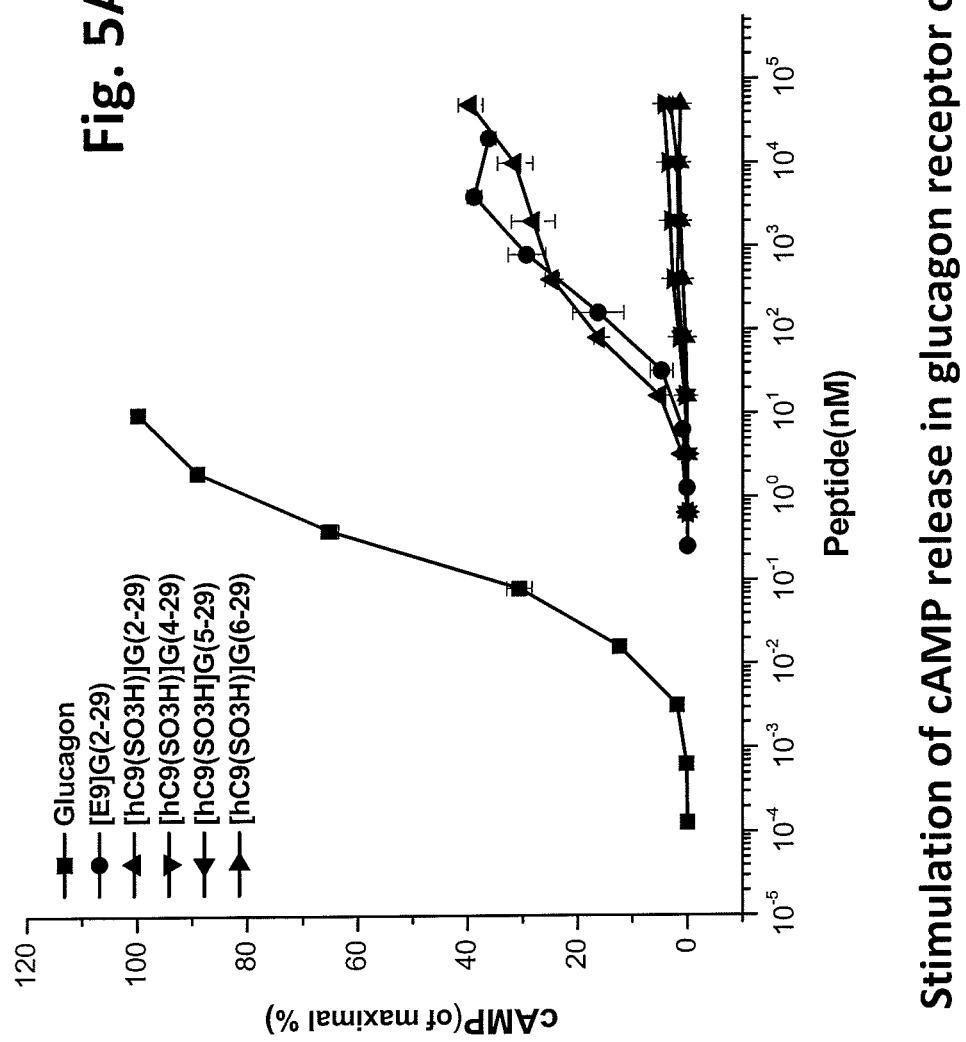

Scheme 1. Synthesis of Fmoc-hCys(SO₃Na)-COOH

Fig. 7: F⁶TSEYSKYLDSRRAQDFVQWLMNT [E9]glucagon(6-29)
| Peptide | Residue 6 | IC$_{50}$ (nM) | pA$_2$ | cAMP (I/A)$_{50}$ |
|---|---|---|---|---|
| [E⁹]G(6-29)-NH$_2$ | 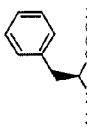 | 36.35 ± 5.23 (n=3) | 7.16 ± 0.27 | 486 |
| [3,4-2(F)-F⁶, E⁹]G(6-29)-NH$_2$ | 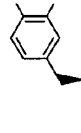 | 36.70 ± 0.54 (n=1) | 7.35±0.08 | 665 |
| [2-Nal⁶, E⁹]G(6-29)-NH$_2$ | 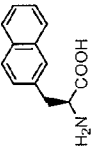 | 95.16±1.32 (n=2) | 7.17±0.64 | 206 (n=2) |
| [Ac-F⁶, E⁹]G(6-29)-NH$_2$ | 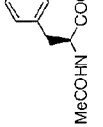 | 37.09±0.26 (n=2) | 6.67±0.63 | 749 (n=2) |
| [PLA⁶, E⁹]G(6-29)-NH$_2$ (PLA: 3-phenyllactic acid) | 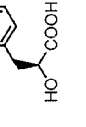 | 12.34 ± 0.13 (n=2) | 7.67±0.30 | 212 (n=3) |
| [MCA⁶, E⁹]G(6-29)-NH$_2$ (MCA: α-methylhydrocinnamic acid) | 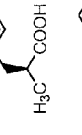 | 114.4±5.76 (n=2) | 6.90±0.83 | 233 (n=2) |
| [BMA⁶, E⁹]G(6-29)-NH$_2$ (BMA: benzylmalonic acid) | 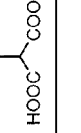 | 80.56± 17.91(n=2) | 6.43±1.44 | 1174 |

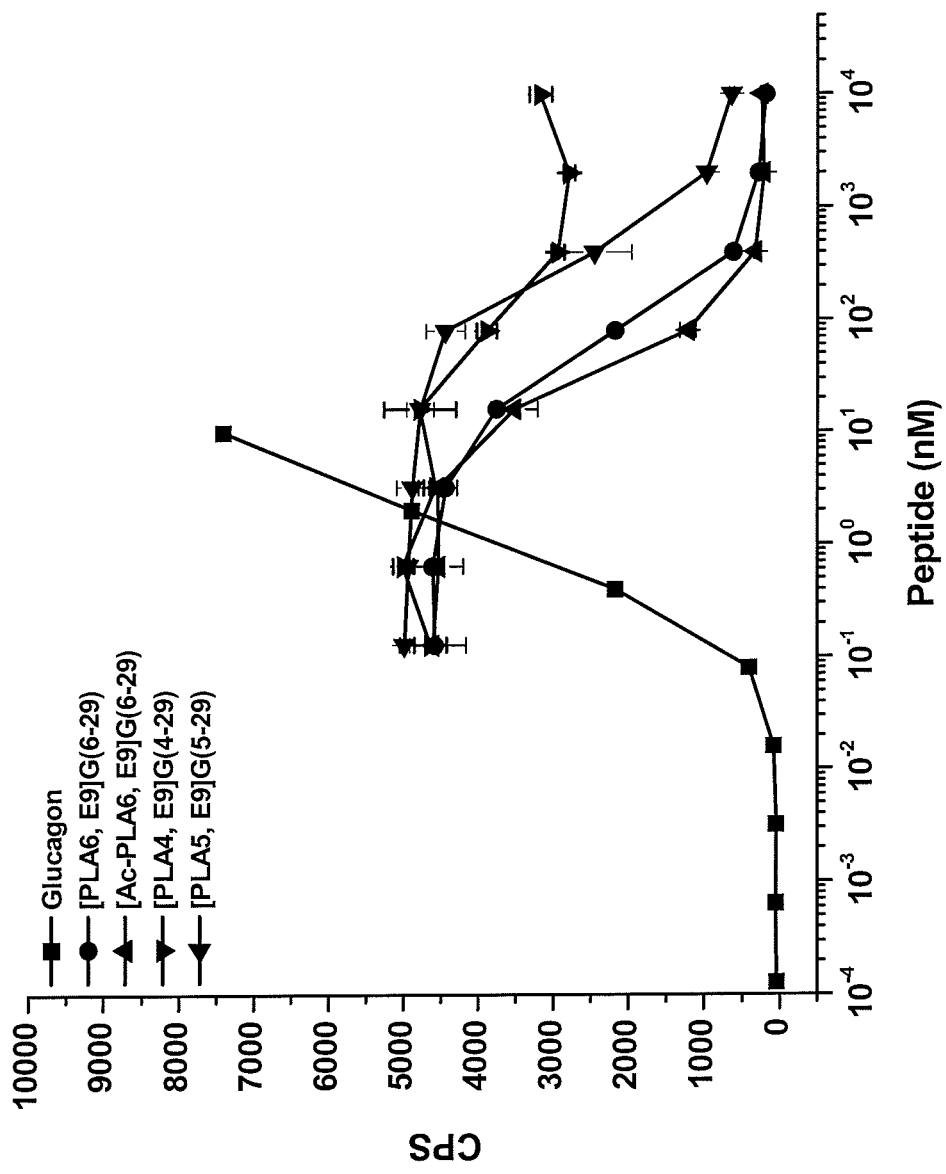
Fig. 8: Inhibition 0.8mM glucagon-induced cAMP release

GLUCAGON ANTAGONISTS

CROSS REFERENCE TO RELATED APPLICATIONS

This application is a U.S. national counterpart application of international application serial No. PCT/US2008/080973 filed Oct. 23, 2008, which claims priority to U.S. Provisional Patent Application No. 60/983,783, filed Oct. 30, 2007. The entire disclosures of PCT/US2008/080973 and U.S. Ser. No. 60/983,783 are hereby incorporated by reference.

INCORPORATION OF SEQUENCE LISTING

The sequence listing with file name 43853A_ST25.txt, created on Sep. 3, 2010 (47 KB) is expressly incorporated by reference in its entirety.

BACKGROUND

Native glucagon is a 29 amino acid peptide that regulates blood glucose levels through enhanced synthesis and mobilization of glucose in the liver. Consequently, the suppression of endogenous glucagon action has been a target for the development of drugs to treat conditions characterized by excessive glucose production, such as diabetes.

Glucagon generally functions as a counter-regulatory hormone, opposing the actions of insulin, to maintain the level of blood glucose, particularly in instances of hypoglycemia. However, in some patients with Type 1 or Type 2 diabetes, absolute or relative elevated glucagon levels have been shown to contribute to the hyperglycemic state. Both in healthy control animals as well as in animal models of Type 1 and Type 2 diabetes, removal of circulating glucagon with selective and specific antibodies has resulted in reduction of the glycemic level (Brand et al., Diabetologia 37, 985 (1994); Diabetes 43, [suppl 1], 172A (1994); Am. J. Physiol. 269, E469-E477 (1995); Diabetes 44 [suppl 1], 134A (1995); Diabetes 45, 1076 (1996)). These studies suggest that glucagon antagonism could be useful in glycemic control of diabetes.

Glucagon exerts its action by binding to and activating its receptor, which is part of the glucagon-secretin branch of the 7-transmembrane G-protein coupled receptor family. The receptor functions by an activation of the adenylyl cyclase resulting in increased cAMP levels. Previous reports have identified peptide-based, (see Unson, C. G. et al. (1989) J. Biol. Chem. 264, 789-94, Ahn, J. et al. (2001) J. Peptide Research 58, 151-8 and Ahn J. et al. (2001) J. Med. Chem. 44, 1372-9) as well as nucleotide-based glucagon antagonists (Sloop K. et al. (2004) J. Clinical Invest. 113, 1571-81). Peptide-based inhibition acts at the level of receptor binding while the latter functions by suppressing intracellular mRNA specific to the glucagon receptor.

Inhibitors of the glucagon receptor have been described, and are generally based on the amino acid sequence of glucagon. Several analogues in which one or more amino acids were either deleted or substituted to produce potent antagonists of glucagon receptor have been described, for example, [des His[1]] [Glu[9]]-glucagon amide (Unson et al., (1989) Peptides 10, 1171; Post et al., (1993) Proc. Natl. Acad. Sci. USA 90, 1662), des His[1], Phe[6] [Glu[9]]-glucagon amide (Azizh et al., (1995) Bioorg. & Med. Chem. Lett. 16, 1849) and Nle[9], Ala[11,16]-glucagon amide (Unson et al. (1994) J. Biol. Chem. 269(17), 12548). Other analogues include substitutions at positions 4 (Ahn J M et al. (2001) J. Pept. Res. 58(2):151-8), 1 (Dharanipragada, R. et al. (1993) Int. J. Pept. Res. 42(1): 68-77) and 4, 5, 12, 17 and 18 in the glucagon sequence (Gysin B et al. 1986. Biochemistry. 25(25):8278-84).

As described herein, high potency glucagon antagonists are provided that represent modifications of the native glucagon peptide. More particularly, the novel glucagon antagonist represent novel chemical modifications of the N-terminus of the native glucagon sequence, producing a highly specific antagonist that exhibits no apparent agonist activity. These compounds can be used in any setting where the suppression of glucagon agonism is desired. In accordance with one embodiment the compounds can be used in the treatment of diabetes.

SUMMARY

In accordance with one embodiment, analogs of glucagon are provided that have pure glucagon antagonist activities. The glucagon antagonists would be used in any setting where the suppression of glucagon agonism is desired. The most immediate and obvious use would be in the treatment of diabetes where glucagon antagonism has been demonstrated in pre-clinical models of hyperglycemia to yield a lowering of blood glucose. These glucagon antagonists can be further modified to improve the biophysical stability and/or aqueous solubility of the compounds while maintaining the antagonist activity of the parent compound.

In accordance with one embodiment a glucagon antagonist is provided comprising a native glucagon peptide that has been modified by the deletion of the first 2-5 amino acids residues from the N-terminus, and a substitution of the aspartic acid at position 9 of the native peptide with an amino acid selected from the group consisting of glutamic acid, homoglutamic acid, β-homoglutamic acid, a sulfonic acid derivative of cysteine, or an alkylcarboxylate derivative of cysteine having the structure of:

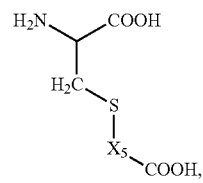

wherein $X_5$ is $C_1$-$C_4$ alkyl, $C_2$-$C_4$ alkenyl, or $C_2$-$C_4$ alkynyl.

In one embodiment, the sulfonic acid derivative of cysteine is cysteic acid or homocysteic acid. In one embodiment the natural carboxylic acid of the C-terminal amino acid is replaced with a charge-neutral group, such as an amide or ester.

In another embodiment a glucagon antagonist is provided (referred to herein as the PLA6 analog) comprising a native glucagon peptide that has been modified by the deletion of the first 5 amino acids residues from the N-terminus, and modification of the remaining N-terminal amino acid (phenylalanine) to replace the native N-terminal amino group with a hydroxyl group (i.e., an N-terminal phenyl-lactic acid (PLA)). The PLA6 analog increases the affinity threefold, and the potency of antagonism, relative to an analog that comprises a deletion of the first five amino acids but retains the N-terminal native phenylalanine. In a further embodiment the aspartic acid residue at position nine of the native protein is constituted with an amino acid selected from the group consisting of aspartic acid, glutamic acid, homoglutamic acid, β-homoglutamic acid, a sulfonic acid derivative of cysteine, or an alkylcarboxylate derivative of cysteine having the structure of:

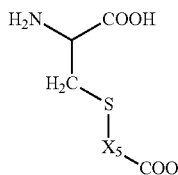

wherein $X_5$ is $C_1$-$C_4$ alkyl, $C_2$-$C_4$ alkenyl, or $C_2$-$C_4$ alkynyl.

In one embodiment the glucagon antagonist comprises a sequence selected from the group consisting of SEQ ID NO: 6, SEQ ID NO: 7, SEQ ID NO: 8, SEQ ID NO: 36, SEQ ID NO: 37 and SEQ ID NO: 38, and in one embodiment the glucagon antagonist comprises the sequence of SEQ ID NO: 7 or 8.

In accordance with one embodiment a glucagon antagonist is provided comprising the sequence of SEQ ID NO: 7 or SEQ ID NO: 37 wherein a polyethylene glycol chain is covalently linked to an amino acid at position 11, 12, 16, 19 or 24, or at the N- or C-terminal amino acid of the peptide. In one embodiment a glucagon antagonist is provided comprising the sequence of SEQ ID NO: 9, SEQ ID NO: 10, SEQ ID NO: 11 or SEQ ID NO: 12, wherein a polyethylene glycol chain is covalently linked to an amino acid at position 11 of SEQ ID NO: 9, position 16 of SEQ ID NO: 10, position 19 of SEQ ID NO: 11 or at both positions 11 and 19 for SEQ ID NO: 12. In one embodiment a single polyethylene glycol chain having a molecular weight selected from the range of about 1,000 to about 5,000 Daltons is covalently bound to the glucagon antagonist peptide. In another embodiment a single polyethylene glycol chain having a molecular weight of at least about 20,000 Daltons is covalently bound to the glucagon antagonist peptide. Alternatively the glucagon antagonist comprises the sequence of SEQ ID NO: 12 and has a polyethylene glycol chain covalently bound to both amino acid position 11 and 19, wherein the combined molecular weight of the two polyethylene chains is either about 1,000 to about 5,000 Daltons or is greater than about 20,000 Daltons.

In one embodiment a glucagon antagonist is provided wherein the carboxy terminal amino acid of the peptide of SEQ ID NO: 7, SEQ ID NO: 8, SEQ ID NO: 36, SEQ ID NO: 39 or SEQ ID NO: 40 is covalently bound to a second peptide comprising the sequence of SEQ ID NO: 19 (GPSSGAPPPS). These compounds may be further modified by the covalent linkage of a PEG group to the glucagon analog at a position selected from 11, 16, 19 for SEQ ID NO: 7, SEQ ID NO: 8, SEQ ID NO: 36, SEQ ID NO: 39 or SEQ ID NO: 40. In one embodiment a glucagon antagonist is provided wherein the carboxy terminal amino acid of the peptide of SEQ ID NO: 7, SEQ ID NO: 8, SEQ ID NO: 36, SEQ ID NO: 39 or SEQ ID NO: 38 is covalently bound to a second peptide comprising the sequence of SEQ ID NO: 53.

In one embodiment, the glucagon antagonist comprises the structure A-B-C as described herein, wherein A is selected from the group consisting of:
  (i) phenyl lactic acid (PLA);
  (ii) an oxy derivative of PLA;
  (iii) a peptide of 2 to 6 amino acids in which two consecutive amino acids of the peptide are linked via an ester or ether bond;

B represents amino acids i to 26 of SEQ ID NO: 1, wherein i is 3, 4, 5, 6, or 7, optionally comprising one or more amino acid modifications, as further described herein;
and C is selected from the group consisting of:
  (x) X;
  (xi) X—Y;
  (xii) X—Y—Z; and
  (xiii) X—Y—Z—R10,
wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid;
wherein R10 is selected from a group consisting of SEQ ID NOs: 19-21 and 53; and
  (xiv) any of (x) to (xiii) in which the C-terminal carboxylate is replaced with an amide.

In another embodiment the solubility of any of the preceding glucagon antagonists which lacks one to five N-terminal amino acids of native glucagon and/or comprises PLA can be improved by modifying the peptide by substitutions and/or additions that introduce a charged amino acid into the C-terminal portion of the peptide, preferably at a position C-terminal to position 22 of the glucagon antagonist. Optionally, one, two or three charged amino acids may be introduced within the C-terminal portion, preferably C-terminal to position 22 (position 27 of native glucagon). In accordance with one embodiment the native amino acid(s) at positions 23 and/or 24 are substituted with a charged amino acid, and/or in a further embodiment one to three charged amino acids are also added to the C-terminus of the peptide. In exemplary embodiments, one, two or all of the charged amino acids are negatively charged. In one embodiment the glucagon antagonist of SEQ ID NO: 7 or SEQ ID NO: 8 is further modified to include an acidic amino acid substitution at position 23 and/or 24. In one embodiment the acidic amino acid is an aspartic acid or glutamic acid residue, and the glucagon antagonist comprises the sequence of SEQ ID NO: 41.

In a further embodiment the stability of the glucagon antagonists which lack amino acids 1-5 of native glucagon and/or comprises PLA at physiological pH can be improved by substituting the aspartic acid residue at position 10 (position 15 of native glucagon) with an amino acid selected from the group consisting of Glu, cysteic acid, homoglutamic acid or homocysteic acid. In accordance with one embodiment such a glucagon antagonist comprises the sequence of SEQ ID NO: 36 or SEQ ID NO: 40.

Any of the glucagon antagonists described herein may be further modified to comprise one or more α,α-disubstituted amino acids at positions that retain the desired activity. In some embodiments, one, two, three, four or more of positions 16, 17, 18, 20, 21, 24 or 29 (according to the amino acid numbering of wild type glucagon) of the glucagon antagonist is substituted with an α,α-disubstituted amino acid. For example, the glucagon antagonist can comprise a substitution of position 16 (according to the amino acid numbering of wild type glucagon) with amino iso-butyric acid (AIB). In some embodiments, one, two, three or more of positions 16, 20, 21 or 24 (according to the amino acid numbering of wild type glucagon) are substituted with AIB. In a specific aspect, the glucagon antagonist comprising one or more α,α-disubstituted amino acids further comprises a C-terminal carboxylate.

Any of the glucagon antagonists described herein may be further modified to comprise an acyl group and/or an alkyl group, which acyl or alkyl group is attached to an amino acid of a spacer or the glucagon antagonist via an ester, ether, thioether, amide, or alkyl amine linkage, as described herein.

Any of the glucagon antagonists described herein may be further modified by truncation or deletion of one or two amino acids of the C-terminus of the glucagon peptide (i.e., position 29 or positions 28 and 29 of the native glucagon peptide).

Additional modifications, e.g. conservative substitutions, may be made to the glucagon antagonist that still allow it to retain its glucagon antagonist activity. Thus, the invention contemplates that any of the glucagon analogs disclosed herein can be further modified to comprise up to 2, 3, 4, 5, 6, 7, 8 or 9 further amino acid modifications, and still retain the desired level of activity of a glucagon antagonist at the glucagon receptor.

Dimers of the glucagon antagonists disclosed herein are also encompassed by the present disclosure. In one embodiment a glucagon antagonist dimer is provided comprising two peptides independently selected form the group consisting of SEQ ID NO: 7, SEQ ID NO: 8, SEQ ID NO: 36, SEQ ID NO: 37, SEQ ID NO: 39 and SEQ ID NO: 40, wherein the two glucagon antagonists are bound to one another through a linker independently bound to position 11 or 19 of the respective peptide chains.

In accordance with one embodiment a pharmaceutical composition is provided comprising the novel glucagon antagonists disclosed herein. In one embodiment the pharmaceutical compositions comprise solutions that are sterilized and contained within various packages. The pharmaceutical compositions can be further packaged as part of a kit that includes a disposable device for administering the composition to a patient.

In accordance with one embodiment a method of rapidly treating hyperglycemia using a pre-formulated aqueous composition is provided. The method comprises the step of administering an effective amount of an aqueous solution comprising a novel modified glucagon antagonist of the present disclosure. In one embodiment the glucagon antagonist is pegylated and the PEG chain has a molecular weight of about 500 to about 5,000 Daltons. In one embodiment the modified glucagon solution is prepackaged in a device that is used to administer the composition to the patient suffering from hyperglycemia.

In accordance with one embodiment an improved method of regulating blood glucose levels in insulin dependent patients is provided. The method comprises the steps of administering insulin in an amount therapeutically effective for the control of diabetes and administering a novel modified glucagon antagonist of the present disclosure, wherein said administering steps are conducted within twelve hours of each other. In one embodiment the glucagon antagonist and the insulin are co-administered as a single composition, wherein the glucagon peptide is pegylated with a PEG chain having a molecular weight selected from the range of about 5,000 to about 40,000 Daltons.

BRIEF DESCRIPTION OF THE DRAWINGS

FIG. 1 is a bar graph representing the stability of Glucagon $Cys^{21}$-maleimidoPEG$_{5K}$ at 37° C. incubated for 24, 48, 72, 96, 144 and 166 hours, respectively.

FIG. 2 represents data generated from HPLC analysis of Glucagon $Cys^{21}$-maleimidoPEG$_{5K}$ at pH 5 incubated at 37° C. for 24, 72 or 144 hours, respectively.

FIG. 3 represents data generated from a binding assay for the listed N-terminally truncated sulfonic acid glucagon antagonist analogs.

FIG. 4 represents data generated measuring glucagon receptor antagonism of the listed peptide antagonists, as measure by cAMP production.

FIGS. 5A & 5B represents data generated measuring glucagon receptor antagonism of the listed glucagon analogs, as measure by cAMP production. More particularly, FIG. 5A compares induction of the glucagon receptor by glucagon analogs [E9]G(2-29) ●, [hC9(SO3H)]G(2-29) ▲, [hC9(SO3H)]G(4-29) ▼, [hC9(SO3H)]G(5-29) ◄ and [hC9(SO3H)]G(6-29) ◂, relative to native glucagon ■. FIG. 5B provides data regarding the inhibitory effect of the same analogs on the induction of the glucagon receptor by 0.2 nM of glucagon. Abbreviations: E9=a substitution of glutamic acid at position 9 relative to native glucagon; G(X-29)=native glucagon N-terminally truncated by X-1 amino acids; hC9(SO3H)=homocysteic acid at position 9, relative to native glucagon.

FIG. 7 represents data comparing the binding affinity and glucagon receptor activity of glucagon antagonists that differ based on modifications to the N-terminal amino acid ("residue 6" of native glucagon).

FIG. 8 represents data generated measuring the inhibitory effect of the listed PLA glucagon analog antagonists on the induction of the glucagon receptor by 0.8 nM of glucagon, as measure by cAMP production. The tested PLA analogs include [PLA6, E9]G(6-29) ●, [Ac-PLA6, E9]G(6-29) ▲, [PLA4, E9]G(4-29) ▼, [PLA5, E9]G(5-29) ◄, compared to the activity of native glucagon ■ alone. Abbreviations: E9=a substitution of glutamic acid at position 9 relative to native glucagon; G(Ac-PLA)=acetylated PLA.

DETAILED DESCRIPTION

Definitions

Figure 5B:
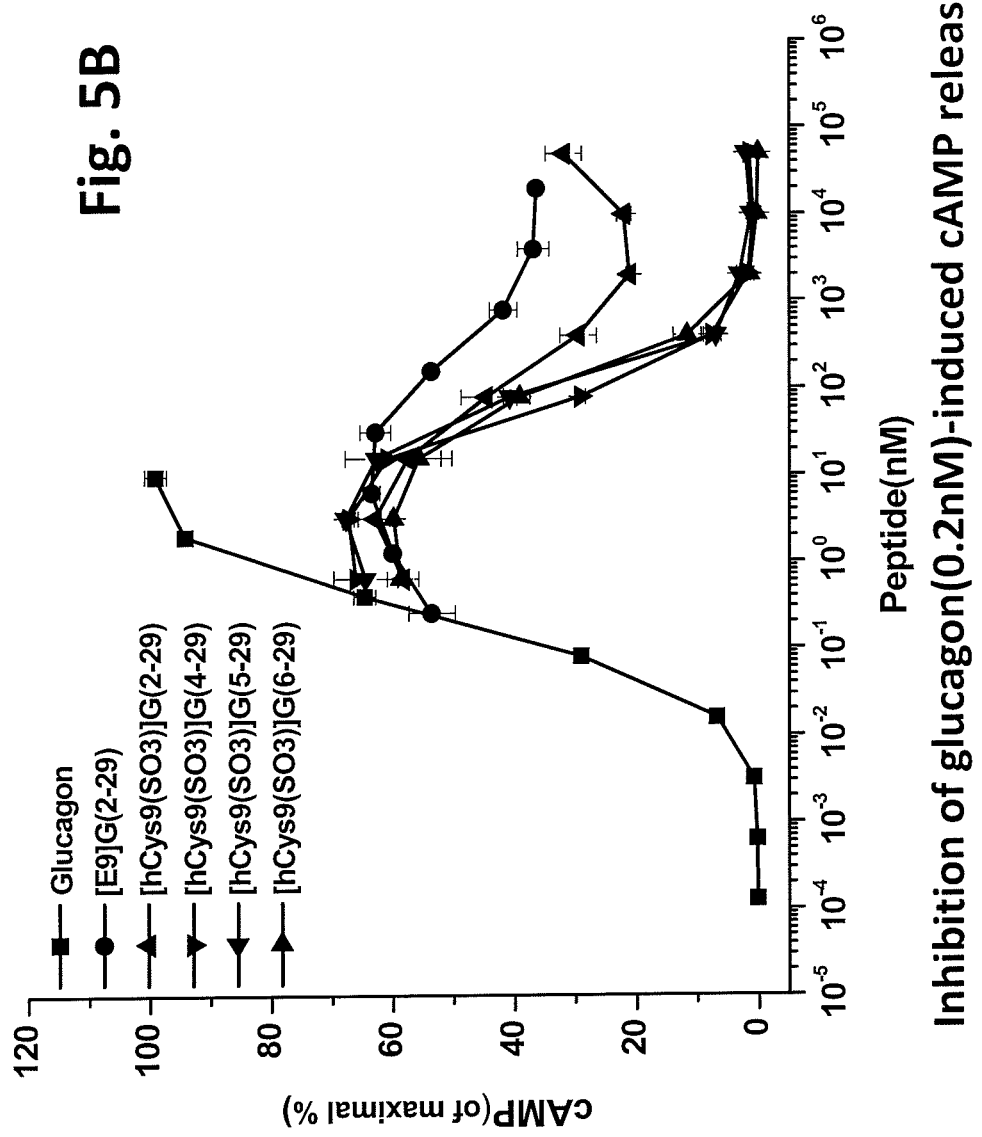
Figure 6:
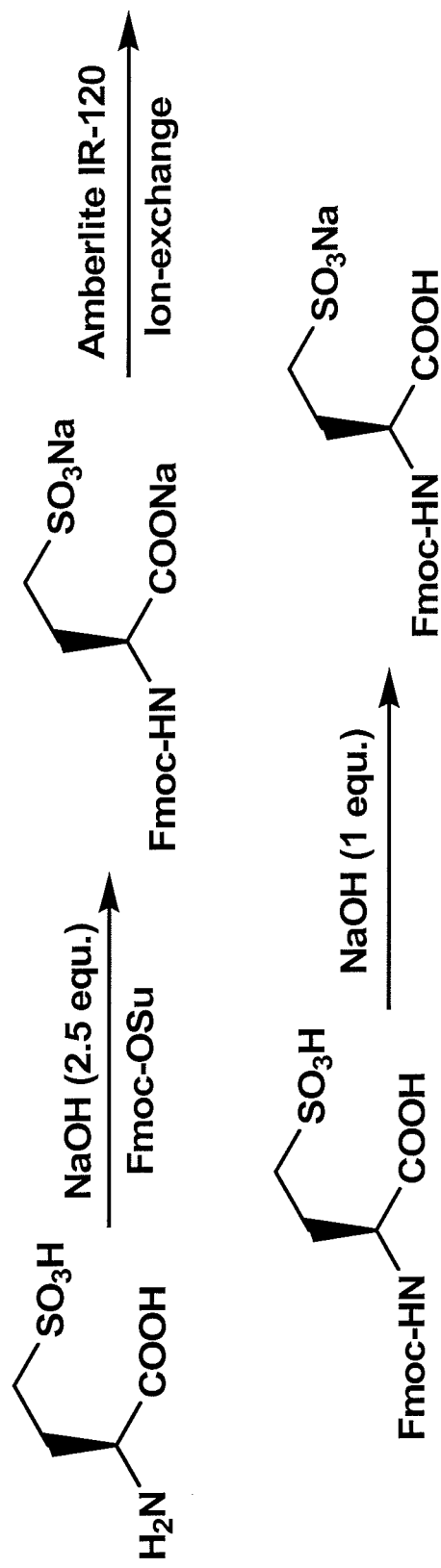
FIG. 6 represents the synthetic scheme for the synthesis of Fmoc-homoCys(SO$_3$Na)—OH. Fmoc-homoCys(SO$_3$Na)—OH dissolves well in DMF or NMP and can be directly incorporated using DIC/HOBT or HBTU/HOBT during the automated peptide synthesis. All hC9(SO$_3$H)-based glucagon antagonist analogs were synthesized by direct incorporation of the sodium form of Fmoc-homoCys(SO$_3$Na)—OH in solid phase peptide synthesis.

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of a glucagon antagonist refers to a non-toxic but sufficient amount of the peptide to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

A "glucagon peptide" as used herein includes any peptide comprising, either the amino acid sequence of SEQ ID NO: 1, or any derivative of the amino acid sequence of SEQ ID NO: 1, including amino acid substitutions, or post translational modifications (e.g. methylation, acylation, ubiquitination and the like) of the peptide, that stimulates glucagon or GLP-1 receptor activity, as measured by cAMP production using the assay described in Example 13.

The term "glucagon antagonist" refers to a compound that counteracts glucagon activity or prevents glucagon function. For example, a glucagon antagonist exhibits at least 60% inhibition (e.g., at least 70% inhibition) and preferably, at least 80% inhibition, of the maximum response achieved by glucagon at the glucagon receptor. In one embodiment, the glucagon antagonist exhibits at least 90% inhibition of the maximum response achieved by glucagon at the glucagon receptor. In a specific embodiment, the glucagon antagonist exhibits 100% inhibition of the maximum response achieved by glucagon at the glucagon receptor. Additionally, a glucagon antagonist at a concentration of about 1 µM exhibits less than about 20% of the maximum agonist activity achieved by glucagon at the glucagon receptor. In one embodiment, the glucagon antagonist exhibits less than about 10% of the maximum agonist activity achieved by glucagon at the glucagon receptor. In a specific embodiment, the glucagon antagonist exhibits less than about 5% of the maximum agonist activity achieved by glucagon at the glucagon receptor. In yet another specific embodiment, the glucagon antagonist exhibits 0% of the maximum agonist activity achieved by glucagon at the glucagon receptor.

A "pure glucagon antagonist" is a glucagon antagonist that does not produce any detected stimulation of glucagon or GLP-1 receptor activity, as measured by cAMP production using a validated in vitro model assay, such as that described in Example 13. For example, a pure glucagon antagonist exhibits less than about 5% (e.g., less than about 4%, less than about 3%, less than about 2%, less than about 1%, about 0%) of the maximum agonist activity achieved by glucagon at the glucagon receptor and exhibits less than about 5% (e.g., less than about 4%, less than about 3%, less than about 2%, less than about 1%, and about 0%) of the maximum agonist activity achieved by GLP-1 at the GLP-1 receptor.

As used herein a "derivative glucagon antagonist" is a peptide that shares greater than 60% amino acid sequence identity with the amino acid of SEQ ID NO: 1, but has been modified to exhibit glucagon antagonist activity. Such modifications include amino acid substitutions or deletions, or post translational modifications (e.g. methylation, amidation, acylation, ubiquitination, pegylation and the like) of the peptide In one example, a derivative glucagon antagonist comprises the glucagon peptide of SEQ ID NO: 1 that has been modified to have the first five amino acid residues deleted from the N-terminus, and has the amino group of the remaining N-terminal amino acid (phenylalanine) substituted with a hydroxyl group.

As used herein an amino acid "modification" refers to a substitution, addition or deletion of an amino acid, and includes substitution with or addition of any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids. As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine As used herein the general term "polyethylene glycol" or "PEG", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 40,000 Daltons. "Polyethylene glycol" or "PEG" is used in combination with a numeric suffix to indicate the approximate average molecular weight thereof. For example, PEG-5,000 refers to polyethylene glycol having a total molecular weight average of about 5,000.

As used herein the term "pegylated" and like terms refers to a compound that has been modified from its native state by linking a polyethylene glycol polymer to the compound. A "pegylated glucagon antagonist" is a glucagon antagonist that has a PEG chain covalently bound to the glucagon antagonist.

As used herein a general reference to a peptide is intended to encompass peptides that have modified amino and carboxy termini. For example, an amino acid chain comprising an amide group in place of the terminal carboxylic acid is intended to be encompassed by an amino acid sequence designating the standard amino acids.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

As used herein the term "charged amino acid" refers to an amino acid that comprises a side chain that is negatively charged (i.e., de-protonated) or positively charged (i.e., protonated) in aqueous solution at physiological pH. For example negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

As used herein a "sulfonic acid derivative of cysteine" refers to compounds of the general structure:

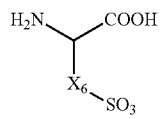

wherein $X_6$ is $C_1$-$C_4$ alkyl, $C_2$-$C_4$ alkene or $C_2$-$C_4$ alkynyl.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl (—CH=CHCH=$CH_2$), 1-butenyl (—CH=CHCH$_2$CH$_3$), hexenyl, pentenyl, and the like.

The term "$C_2$-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "pH stabilized glucagon antagonist" refers to a glucagon analog that exhibits superior stability and solubility, relative to native glucagon, in aqueous buffers in the broadest pH range used for pharmacological purposes.

As used herein the term "acidic amino acid" refers to an amino acid that comprises a second acidic moiety, including for example, a carboxylic acid or sulfonic acid group.

As used herein the term "patient" without further designation is intended to encompass any warm blooded vertebrate domesticated animal (including for example, but not limited to livestock, horses, cats, dogs and other pets) and humans.

As used herein, the term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

EMBODIMENTS

Disclosed herein are glucagon antagonists that are highly specific to glucagon suppression and possess no apparent agonist activity. Such glucagon antagonists are utilized in any setting where the suppression of glucagon's agonism is desired. For example glucagon antagonists can be used in the treatment of diabetes where glucagon antagonism has been demonstrated in pre-clinical models of hyperglycemia to yield a lowering of blood glucose.

Specific analogs of glucagon have been developed wherein the normally occurring aspartic acid at position nine has been substituted with glutamic acid or a cysteic acid-based derivative. More particularly, deletion of the first amino acid (des-His) and substitution of the aspartic acid at position 9 with glutamic acid produces a glucagon antagonist. Glucagon derivatives having sulfonic acid substituents substituted at amino acid position nine of glucagon perform similarly to the carboxylic acid-based amino acids but with a few critical differences in relation to physical properties such as solubility. Homocysteic acid (hCysSO$_3$) when substituted for the isosteric glutamic acid at position nine in the conventional des-His, Glu9 glucagon antagonist retains a partial antagonist and weak agonist.

Surprisingly, applicants have discovered that the removal of additional N-terminal residues, including for example, the removal of the first five amino acids (yielding des(1-5), and substitution of position 9 (according to the numbering of SEQ ID NO: 1) with hCys(SO$_3$), homoglutamic acid, β-homoglutamic acid, or an alkylcarboxylate derivative of cysteine having the structure of:

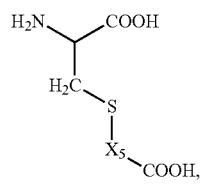

wherein $X_5$ is $C_1$-$C_4$ alkyl, $C_2$-$C_4$ alkenyl, or $C_2$-$C_4$ alkynyl, provides a compound that performs as a hormonal antagonist that is highly specific, potent and without contaminating agonist properties. Accordingly, glucagon derivative peptides that exhibit pure glucagon antagonist activity are disclosed herein. In accordance with one embodiment the glucagon antagonist exhibits activity that reduces glucagon receptor glucagon-induced cAMP production by a maximum of at least 50% when the glucagon receptor is contacted simultaneously with 0.8 nM of glucagon and the glucagon antagonist, as measured by cAMP production in an in vitro assay. In one embodiment, the glucagon antagonist reduces glucagon receptor glucagon-induced cAMP production by a maximum amount of at least 80%.

In accordance with one embodiment a derivative glucagon antagonist is provided that comprises a glucagon peptide modified, relative to the wild type sequence of SEQ ID NO: 1, by the deletion of two to five amino acid residues from the N-terminus and substitution of the aspartic acid residue at position nine of the native protein with a glutamic acid, homoglutamic acid, β-homoglutamic acid, a sulfonic acid derivative of cysteine, or an alkylcarboxylate derivative of cysteine having the structure of:

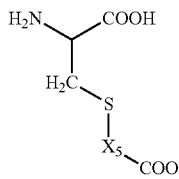

wherein $X_5$ is $C_1$-$C_4$ alkyl, $C_2$-$C_4$ alkenyl, or $C_2$-$C_4$ alkynyl.

In one specific embodiment, the glucagon antagonist comprising the deletion of two to five amino acid residues from the N-terminus and substitution of the Asp at position 9 of the native glucagon, is further modified by up to three amino acid modifications. For example, the glucagon antagonist may comprise one, two, or three conservative amino acid modifications. Alternatively or additionally, the glucagon antagonist may comprise one or more amino acid modifications selected from the group consisting of:

A. substitution of one or two amino acids at positions 10, 20, and 24, (according to the amino acid numbering of SEQ ID NO: 1), or the N- or C-terminal amino acid of the glucagon antagonist with an amino acid covalently attached to an acyl group or alkyl group via an ester, ether, thioether, amide, or alkyl amine linkage;

B. substitution of one or two amino acids at positions 16, 17, 20, 21, and 24 (according to the amino acid numbering of SEQ ID NO: 1), or the N- or C-terminal amino acid of the glucagon antagonist with an amino acid selected from the group consisting of: Cys, Lys, ornithine, homocysteine, and acetyl-phenylalanine (Ac-Phe), wherein the amino acid of the group is covalently bonded to a hydrophilic moiety;

C. addition of an amino acid covalently bonded to a hydrophilic moiety to the N- or C-terminus of the glucagon antagonist;

D. substitution of Asp at position 15 (according to the numbering of SEQ ID NO: 1) with cysteic acid, glutamic acid, homoglutamic acid, and homocysteic acid;

E. substitution of Ser at position 16 (according to the numbering of SEQ ID NO: 1) with cysteic acid, glutamic acid, homoglutamic acid, and homocysteic acid;

F. substitution with AIB at one or more of positions 16, 20, 21, and 24 according to the amino acid numbering of SEQ ID NO: 1;

G. deletion of the amino acid at position 29 or the amino acids at positions 28 and 29, according to the numbering of SEQ ID NO: 1;

H. substitution of each or both of the Asn at position 28 and the Thr at position 29 (according to the amino acid numbering of SEQ ID NO: 1) with charged amino acids; and/or addition of one to two charged amino acids at the C-terminus of SEQ ID NO: 1;

I. substitution of the Met at position 27 (according to the numbering of SEQ ID NO: 1) with Leu or norleucine;

J. addition of a peptide having the amino acid sequence of any of SEQ ID NOs: 19-21 and 53 to the C-terminus of SEQ ID NO: 1; wherein Thr at position 29 (according to the numbering of SEQ ID NO: 1) is Thr or Gly; and K. replacement of the C-terminal carboxylate with an amide or ester.

In a specific embodiment, the glucagon antagonist comprises an amino acid modification of A, B, or C, as described above, or a combination thereof. In yet another specific embodiment, the glucagon antagonist further comprises an amino acid modification of any of D to K as described above, or a combination thereof, in addition to the amino acid modification(s) of A, B, and/or C.

In one embodiment the glucagon antagonist comprises a glucagon peptide, wherein the first 5 amino acids have been removed from the N-terminus, and the remaining N-terminal amino group has been replaced with a hydroxyl group (the "PLA6 analog"), producing the peptide of SEQ ID NO: 39. Applicants have found that substitution of phenyl-lactic acid for phenylalanine in glucagon antagonist analogs that have the first five amino acids deleted and substitution of a glutamic acid at position 9 (relative to native glucagon) further enhances the potency of those glucagon antagonist analogs.

In one embodiment the glucagon antagonist peptide of SEQ ID NO: 39 is further modified by substituting the aspartic acid residue at position four (position 9 of the native glucagon) with an amino acid of the general structure:

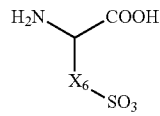

wherein $X_6$ is $C_1$-$C_3$ alkyl, $C_2$-$C_3$ alkene or $C_2$-$C_3$ alkynyl, and in one embodiment X is $C_1$-$C_3$ alkyl, and in another embodiment X is $C_2$ alkyl. In one embodiment the glucagon antagonist comprises a glucagon peptide, wherein the first 5 amino acids have been removed from the N-terminus, and the aspartic acid residue at position four (position 9 of the native glucagon) has been substituted with cysteic acid or homocysteic acid. In one embodiment the glucagon antagonist comprises a glucagon peptide comprising an amino acid sequence selected from the group consisting of SEQ ID NO: 39, SEQ ID NO: 7 and SEQ ID NO: 8. In one embodiment the glucagon antagonist comprises an amino acid sequence selected from the group consisting of SEQ ID NO: 8, wherein the amino acid at position four is homocysteic acid.

In another embodiment, the glucagon antagonist of SEQ ID NO: 39 is further modified by substituting the aspartic acid residue at position four (position 9 of the native glucagon) with glutamic acid, homoglutamic acid, β-homoglutamic acid, or an alkylcarboxylate derivative of cysteine having the structure of:

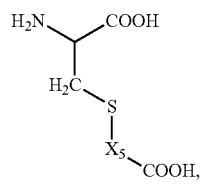

wherein $X_5$ is $C_1$-$C_4$ alkyl, $C_2$-$C_4$ alkenyl, or $C_2$-$C_4$ alkynyl. In a specific embodiment, X is $C_1$ or $C_2$ alkyl.

However, applicants have discovered that with the substitution of the N-terminal phenylalanine with PLA in a des1-5 glucagon analog (i.e., a glucagon analog having the first five amino acids deleted), further substitution of the native aspartic acid residue at position four (position 9 of the native glucagon) is not required to produce an analog that exhibits pure antagonism. This result is surprising in light of the prior art teachings that the native aspartic acid residue at position four must substituted to produce high affinity and potent antagonists of glucagon (2-29) analogs. The use of the PLA substitution improves the relative potency of the Asp9 analog to a point comparable to that of the Glu9 and hCys($SO_3H$)$_9$ analogs. (see Tables 6 and 7 in the Examples).

Substitution of the phenylalanine residue with other phenylalanine analogs, including 3,4-2F-phenylalnine (3,4-2F-Phe), 2-naphthyalanine (2-Nal), N-acyl-phenylalanine (Ac-Phe), alpha-methylhydrocinnamic acid (MCA) and benzylmalonic acid (BMA) did not perform as potently as the PLA substitution (see FIG. 7).

Substituting PLA at sites other than at position six (according to the amino acid numbering of native glucagon), including at positions 4 and 5 reveals that the PLA6 analog is an appreciably more potent antagonist than glucagon analogs having a slightly extended N-terminus (see the results presented in Table 8 and FIG. 8). The results presented in FIG. 8 also demonstrate that acylation of the PLA hydroxy group does not affect PLA6 analog potency. Accordingly, the present invention also includes analogs wherein the N-terminal amino group is substituted with an acylated and alkylated "O-terminal" peptides.

Furthermore, the PLA6 substitution not only increases the potency of the antagonist but also serves a critical role in pegylation. The PLA6 analogs can be selectively pegylated without restoration of glucagon agonism. In the absence of the PLA substitution, pegylation of the analog surprisingly induces glucagon agonism. This glucagon agonism is not seen in the pegylated PLA6 analogs. Several sites for pegylation were investigated including positions 3, 6 and 19 (positions 8, 11 and 19 of native glucagon) and at the N-terminal amino acid residue (see Table 12). In one embodiment the pegylation is at position 19 (position 24 of native glucagon) as that site exhibits the most potent and selective glucagon antagonism.

In one embodiment, the glucagon antagonist comprises the general structure of A-B-C, wherein A is selected from the group consisting of:
(i) phenyl lactic acid (PLA);
(ii) an oxy derivative of PLA;
(iii) a peptide of 2 to 6 amino acids in which two consecutive amino acids of the peptide are linked via an ester or ether bond;

B represents amino acids i to 26 of SEQ ID NO: 1, wherein i is 3, 4, 5, 6, or 7, optionally comprising one or more amino acid modifications selected from the group consisting of:
(iv) Asp at position 9 (according to the amino acid numbering of SEQ ID NO: 1) is substituted with a Glu, a sulfonic acid derivative of Cys, homoglutamic acid, β-homoglutamic acid, or an alkylcarboxylate derivative of cysteine having the structure of:

$$H_2N-CH(COOH)-CH_2-S-X_5-COOH$$

wherein $X_5$ is $C_1$-$C_4$ alkyl, $C_2$-$C_4$ alkenyl, or $C_2$-$C_4$ alkynyl.
(v) substitution of one or two amino acids at positions 10, 20, and 24, (according to the amino acid numbering of SEQ ID NO: 1) with an amino acid covalently attached to an acyl or alkyl group via an ester, ether, thioether, amide, or alkyl amine linkage;
(vi) substitution of one or two amino acids at positions 16, 17, 20, 21, and 24 (according to the amino acid numbering of SEQ ID NO: 1) with an amino acid selected from the group consisting of: Cys, Lys, ornithine, homocysteine, and acetyl-phenylalanine (Ac-Phe), wherein the amino acid of the group is covalently attached to a hydrophilic moiety;
(vii) Asp at position 15 (according to the numbering of SEQ ID NO: 1) is substituted with cysteic acid, glutamic acid, homoglutamic acid, and homocysteic acid;
(viii) Ser at position 16 (according to the numbering of SEQ ID NO: 1) is substituted with cysteic acid, glutamic acid, homoglutamic acid, and homocysteic acid;
(ix) substitution with AIB at one or more of positions 16, 20, 21, and 24 according to the amino acid numbering of SEQ ID NO: 1;

and C is selected from the group consisting of:
(x) X;
(xi) X—Y;
(xii) X—Y—Z; and
(xiii) X—Y—Z—R10, wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid; wherein R10 is selected from a group consisting of SEQ ID NOs: 19-21 and 53; and (xiv) any of (x) to (xiii) in which the C-terminal carboxylate is replaced with an amide.

In a specific aspect, the glucagon antagonist comprises an oxy derivative of PLA. As used herein "oxy derivative of PLA" refers to a compound comprising a modified structure of PLA in which the hydroxyl group has been replaced with O—$R_{11}$, wherein $R_{11}$ is a chemical moiety. In this regard, the oxy derivative of PLA can be, for example, an ester of PLA or an ether of PLA.

Methods of making oxy derivatives of PLA are known in the art. For example, when the oxy derivative is an ester of PLA, the ester may be formed by upon reaction of the hydroxyl of PLA with a carbonyl bearing a nucleophile. The nucleophile can be any suitable nucleophile, including, but not limited to an amine or hydroxyl. Accordingly, the ester of PLA can comprise the structure of Formula IV:

Formula IV wherein R7 is an ester formed upon reaction of the hydroxyl of PLA with a carbonyl bearing a nucleophile.

The carbonyl bearing a nucleophile (which reacts with the hydroxyl of PLA to form an ester) can be, for example, a carboxylic acid, a carboxylic acid derivative, or an activated ester of a carboxylic acid. The carboxylic acid derivative can be, but is not limited to, an acyl chloride, an acid anhydride, an amide, an ester, or a nitrile. The activated ester of a carboxylic acid can be, for example, N-hydroxysuccinimide (NHS), tosylate (Tos), a carbodiimide, or a hexafluorophosphate. In some embodiments, the carbodiimide is 1,3-dicyclohexylcarbodiimide (DCC), 1,1'-carbonyldiimidazole (CDI), 1-ethyl-3-(3-dimethylaminopropyl)carbodiimide hydrochloride (EDC), or 1,3-diisopropylcarbodiimide (DICD). In some embodiments, the hexafluorophosphate is selected from a group consisting of hexafluorophosphate benzotriazol-1-yl-oxy-tris(dimethylamino)phosphonium hexafluorophosphate (BOP), benzotriazol-1-yl-oxytripyrrolidinophosphonium hexafluorophosphate (PyBOP), 2-(1H-7-azabenzotriazol-1-yl)-1,1,3,3-tetramethyl uronium hexafluorophosphate (HATU), and o-benzotriazole-N,N,N',N'-tetramethyl-uronium-hexafluoro-phosphate (HBTU).

Methods of making ethers from reaction with a hydroxyl group (e.g., the hydroxyl of PLA) also are known in the art. For example, the hydroxyl group of PLA may be reacted with a halogenated alkyl or tosylated alkyl alcohol to form an ether bond.

Generally, the chemical moiety of $R_{11}$ is one which does not decrease the activity of the glucagon antagonist. In some embodiments, the chemical moiety enhances the activity, stability, and/or solubility of the glucagon antagonist.

In a specific embodiment, the chemical moiety bound to PLA via an oxygen-containing bond (e.g., via an ester or ether bond) is a polymer (e.g., a polyalkylene glycol), a carbohydrate, an amino acid, a peptide, or a lipid, e.g., a fatty acid or a steroid.

In a specific embodiment, the chemical moiety is an amino acid, which, optionally, is a part of a peptide, such that Formula IV is a depsipeptide. In this regard, PLA may be at a position other than the N-terminal amino acid residue of the glucagon antagonist, such that the glucagon antagonist comprises one or more (e.g., 1, 2, 3, 4, 5, 6, or more) amino acids N-terminal to the PLA residue. For example, the glucagon antagonist can comprise PLA at position n, wherein n is 2, 3, 4, 5, or 6 of the glucagon antagonist.

The amino acids N-terminal to the PLA residue may be synthetic or naturally-occurring. In a specific embodiment, the amino acids which are N-terminal PLA are naturally-occurring amino acids. In one embodiment, the amino acids which are N-terminal to PLA are the N-terminal amino acids of native glucagon. For example, the glucagon antagonist can comprise at the N-terminus the amino acid sequence of any of SEQ ID NOs: 54-58, wherein PLA is linked to threonine via an ester bond:

```
SEQ ID NO: 54    His-Ser-Gln-Gly-Thr-PLA

SEQ ID NO: 55    Ser-Gln-Gly-Thr-PLA

SEQ ID NO: 56    Gln-Gly-Thr-PLA

SEQ ID NO: 57    Gly-Thr-PLA

SEQ ID NO: 58    Thr-PLA
```

In an alternative embodiment, one or more of the N-terminal amino acids may be substituted with an amino acid other than the amino acid of native glucagon. For example, when the glucagon antagonist comprises PLA as the amino acid at position 5 or 6, the amino acid at position 1 and/or position 2 may be an amino acid which reduces susceptibility to cleavage by dipeptidyl peptidase IV. More particularly, in some embodiments, position 1 of the glucagon antagonist is an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. More particularly, in some embodiments, position 2 of the antagonist peptide is an amino acid selected from the group consisting of D-serine, D-alanine, valine, glycine, N-methyl serine, N-methyl alanine, and aminoisobutyric acid (AIB). Also, for example, when the glucagon antagonist comprises PLA as the amino acid at position 4, 5, or 6, the amino acid at position 3 of the glucagon antagonist may be glutamic acid, as opposed to the native glutamine residue of native glucagon. In an exemplary embodiment of the invention, the glucagon antagonist comprises at the N-terminus the amino acid sequence of any of SEQ ID NOs: 59-61.

With respect to the glucagon antagonists comprising a compound of Formula IV, the polymer may be any polymer, provided that it can react with the hydroxyl group of PLA. The polymer may be one that naturally or normally comprises a carbonyl bearing a nucleophile. Alternatively, the polymer may be one which was derivatized to comprise the carbonyl bearing the carbonyl. The polymer may be a derivatized polymer of any of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

The polymer can be a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

The polymer can be a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In one embodiment, the polymer is a water-soluble polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In a specific embodiment, the polymer is a polyalkylene glycol, including, for example, polyethylene glycol (PEG).

The carbohydrate may be any carbohydrate provided that it comprises or is made to comprise a carbonyl with an alpha leaving group. The carbohydrate, for example, may be one which has been derivatized to comprise a carbonyl with an alpha leaving group. In this regard, the carbohydrate may be a derivatized form of a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

With respect to the glucagon antagonists comprising a compound of Formula IV, the lipid may be any lipid comprising a carbonyl with an alpha leaving group. The lipid, for example, may be one which is derivatized to comprise the carbonyl. In this regard, the lipid, may be a derivative of a fatty acid (e.g., a $C_4$-$C_{30}$ fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide. oil, wax, cholesterol, sterol, fat-soluble vitamin, monoglyceride, diglyceride, triglyceride, a phospholipid.

In one embodiment, R7 has a molecular weight of about 100 kDa or less, e.g., about 90 kDa or less, about 80 kDa or less, about 70 kDa or less, about 60 kDa or less, about 50 kDa or less, about 40 kDa or less. Accordingly, R7 can have a molecular weight of about 35 kDa or less, about 30 kDa or less, about 25 kDa or less, about 20 kDa or less, about 15 kDa or less, about 10 kDa or less, about 5 kDa or less, or about 1 kDa.

In an alternative embodiment, the glucagon antagonist comprises as A, a peptide of 2 to 6 amino acids in which two consecutive amino acids of the peptide are linked via an ester or ether bond. The ester or ether bond may be, e.g., between amino acids 2 and 3, 3 and 4, 4 and 5, or 5 and 6. Optionally the peptide may be further modified by covalent linkage to another chemical moiety including linkage to a polymer (e.g. a hydrophilic polymer), alkylation, or acylation.

The peptide may comprise any amino acids, synthetic or naturally occurring, provided that at least two consecutive amino acids of the peptide are linked via an ester or ether bond. In a specific embodiment, the peptide comprises amino acids of native glucagon. For example, the peptide can comprise j to 6 of native glucagon (SEQ ID NO: 1), wherein j is 1, 2, 3, 4, or 5. Alternatively, the peptide can comprise an amino acid sequence based on the N-terminus of SEQ ID NO: 1 with one or more amino acid modifications. The amino acid at position 1 and/or position 2 may be an amino acid which reduces susceptibility to cleavage by dipeptidyl peptidase IV. For instance, the peptide can comprise at position 1 of the glucagon antagonist an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. More particularly, in some embodiments, position 2 of the antagonist peptide is an amino acid selected from the group consisting of D-serine, D-alanine, valine, glycine, N-methyl serine, N-methyl alanine, and aminoisobutyric acid (AIB). Also, for example, the amino acid at position 3 of the glucagon antagonist may be glutamic acid, as opposed to the native glutamine residue of native glucagon. Accordingly, the glucagon antagonist can comprise an amino acid sequence of:

```
Xaa₁-Xaa₂-Xaa₃-Thr-Gly-Phe;     (SEQ ID NO: 68)

Xaa₂-Xaa₃-Thr-Gly-Phe;          (SEQ ID NO: 69)
or

Xaa₃-Thr-Gly-Phe;               (SEQ ID NO: 70)
``` wherein $Xaa_1$ is selected from a group consisting of: His, D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine; $Xaa_2$ is selected from a group consisting of: Ser, D-serine, D-alanine, valine, glycine, N-methyl serine, N-methyl alanine, and aminoisobutyric acid (AIB); and $Xaa_3$ is Gln or Glu.

The present invention also encompasses embodiments wherein the C-terminal amino acid of the glucagon antagonists have an amide group substituting for the carboxylic acid group that is present on the native amino acid.

The glucagon antagonists can be further modified to improve the peptide's solubility in aqueous solutions at physiological pH, while retaining the glucagon antagonist activity. Introduction of hydrophilic groups at positions corresponding to positions 1, 16, 17, 20, 21, 24 and 29 of the native peptide, or at the C-terminus, can improve the solubility of the resulting glucagon antagonist in solutions having a physiological pH, while retaining the parent compounds antagonist activity. Therefore, in one embodiment the presently disclosed glucagon antagonists are further modified to comprise one or more hydrophilic groups covalently linked to the side chains of amino acids corresponding to amino acid positions 1, 16, 17, 20, 21, 24 and 29 of the native glucagon peptide or of the N- or C-terminal amino acid. In a further embodiment the side chains of amino acids corresponding to amino acid positions 16 and 24 of the native glucagon peptide are covalently bound to hydrophilic groups, and in one embodiment the hydrophilic group is polyethylene glycol (PEG).

In some embodiments, wherein the glucagon antagonist is PEGylated, the glucagon antagonist comprises the shortened glucagon peptides, specifically 6-29 where the "N-terminal" amino acid is PLA (phenyl-lactic acid). Such glucagon derivatives exhibit unique virtues. They are more potent peptides than those with the native N-terminal phenylalanine and they suppress any glucagon agonism that results from pegylation, something not seen with the native phenylalanine.

Finally, while the current literature establishes that a substitution of the native aspartic acid at position 9 is required for antagonist activity, applicants have discovered the surprising result that such a substitution is no longer required in the PLA$^6$-(6-29) glucagon analogs.

In one embodiment an amino acid of the glucagon antagonist is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, an amino acid of the glucagon antagonist is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol. In accordance with one embodiment the lysine residue corresponding to position 12 of the native peptide is substituted with arginine and a single lysine substitution is inserted for one of the amino acids corresponding to position 1, 16, 17, 20, 21, 24 or 29 of the native peptide, or a lysine is added to the N- or C-terminus of the glucagon antagonist.

In another embodiment the methionine residue corresponding to position 27 of the native peptide is changed to leucine or norleucine to prevent oxidative degradation of the peptide.

In some embodiments, the glucagon antagonists described herein are further modified by truncation or deletion of one or two amino acids of the C-terminus of the glucagon peptide (i.e., truncation of the amino acid at position 29 or at positions 28 and 29 of native glucagon) without affecting activity and/or potency at the glucagon receptor. In this regard, the glucagon antagonist described herein can, for example, consist essentially of or consist of amino acids 1-27, 1-28, 2-27, 2-28, 3-27, 3-28, 4-27, 4-28, 5-27, 5-28, 6-27, or 6-28 of the native glucagon peptide (SEQ ID NO: 1) with one or more modifications resulting in glucagon antagonistic activity as described herein.

The presently disclosed glucagon antagonists also encompass amino acid substitutions at positions that are known not to be critical to the function of the glucagon peptide. In one embodiment the substitutions are conservative amino acid substitutions at one, two or three positions selected from the group consisting of 2, 5, 6, 7, 8, 9, 12, 13, 14, 15, 16, 19, 22, 23 or 24 of SEQ ID NO: 39. In one embodiment the glucagon antagonist comprises a derivative peptide of SEQ ID NO: 42 wherein the glucagon peptide comprises a further amino acid substitution relative to SEQ ID NO: 42 at one to three amino acid positions selected from positions 2, 5, 6, 8, 9, 12, 13 and 14. In one embodiment the substitutions at positions 2, 5, 6, 8, 9, 12, 13 and 14 of SEQ ID NO: 42 are conservative amino acid substitutions. In one embodiment the amino acids corresponding to positions 16, 17, 20, 21, 24 or 29 of the native peptide, and more particularly at position 21 and/or 24 are substituted with cysteine or lysine, wherein a PEG chain is covalently attached to the substituted cysteine or lysine residue.

In those embodiments wherein the glucagon antagonist comprises a polyethylene glycol chain, the polyethylene chain may be in the form of a straight chain or it may be branched. In accordance with one embodiment the polyethylene glycol chain has an average molecular weight selected from the range of about 500 to about 10,000 Daltons. In one embodiment the polyethylene glycol chain has an average molecular weight selected from the range of about 1,000 to about 5,000 Daltons. In one embodiment the polyethylene glycol chain has an average molecular weight selected from the range of about 1,000 to about 5,000 Daltons. In one embodiment the polyethylene glycol chain has an average molecular weight selected of about 1,000 to about 2,000 Daltons. In one embodiment the polyethylene glycol chain has an average molecular weight of about 1,000 Daltons.

In accordance with one embodiment the modified glucagon antagonist comprises two or more polyethylene chains covalently bound to the peptide wherein the total molecular weight of the glucagon chains is about 1,000 to about 5,000 Daltons. In one embodiment the pegylated glucagon antagonist comprises a peptide selected from the group consisting of SEQ ID NO: 12, and SEQ ID NO: 22, wherein said peptide comprise a polyethylene glycol chain linked to the amino acid at positions 11 and 19 and the combined molecular weight of the two PEG chains is about 1,000 to about 5,000 Daltons.

In accordance with one embodiment a glucagon antagonist is provided comprising a modified glucagon peptide selected from the group consisting of:

R$_1$-Phe-Thr-Ser-Xaa-Tyr-Ser-Xaa-Tyr-Leu-Xaa-Xaa-Arg-Arg-Ala-Gln-Asp-Phe-Val-Gln-Trp-Leu-Xaa-Asn-Thr-R$_2$ (SEQ ID NO: 9),

R$_1$-Phe-Thr-Ser-Xaa-Tyr-Ser-Xaa-Tyr-Leu-Asp-Ser-Arg-Arg-Ala-Gln-Xaa-Phe-Val-Gln-Trp-Leu-Xaa-Asn-Thr-R$_2$ (SEQ ID NO: 10),

R$_1$-Phe-Thr-Ser-Xaa-Tyr-Ser-Xaa-Tyr-Leu-Asp-Ser-Arg-Arg-Ala-Gln-Asp-Phe-Val-Xaa-Trp-Leu-Xaa-Asn-Thr-R$_2$ (SEQ ID NO: 11) and R$_1$-Phe-Thr-Ser-Xaa-Tyr-Ser-Xaa-Tyr-Leu-Asp-Ser-Arg-Arg-Ala-Gln-Xaa-Phe-Val-Xaa-Trp-Leu-Xaa-Asn-Thr-R$_2$ (SEQ ID NO: 12), wherein Xaa at position 4=aspartic acid, glutamic acid, cysteic acid or homocysteic acid, Xaa at position 7=Lys or Arg, Xaa at position 10 is aspartic acid, cysteic acid, glutamic acid, homoglutamic acid and homocysteic acid; Xaa at position 11 is Ser, Lys, Cys, Orn, homocysteine or acetyl phenylalanine, Xaa at position 16 is Asp, Lys, Cys, Orn, homocysteine or acetyl phenylalanine a and Xaa at position 19 is Gln, Lys, Cys, Orn, homocysteine and acetyl phenylalanine, Xaa at position 22=Met, Leu or Nle, R$_1$ is OH or NH$_2$, and R$_2$ is COOH or CONH$_2$, wherein the peptide is pegylated at position 11 for SEQ ID NO: 9, at position 16 for SEQ ID NO: 10, position 19 for SEQ ID NO: 11 and at positions 16 and 19 of SEQ ID NO: 12, with the proviso that when Xaa at position 4=aspartic acid then R$_1$ is OH. In accordance with one embodiment the peptide comprises the sequence of SEQ ID NO: 9, SEQ ID NO: 10 or SEQ ID NO: 11, wherein R$_1$ is OH and R$_2$ is CONH$_2$. In one embodiment the peptide comprises the sequence of SEQ ID NO: 9, SEQ ID NO: 10 or SEQ ID NO: 11, wherein R$_1$ is OH, R$_2$ is CONH$_2$ and the amino acid at position 4 is aspartic acid, and in a further embodiment such peptides comprise a carboxy terminal extension comprising the sequence of SEQ ID NO: 19.

In accordance with one embodiment the peptide comprises a sequence selected from the group consisting of SEQ ID NO: 9, SEQ ID NO: 10, SEQ ID NO: 13, SEQ ID NO: 14, and SEQ ID NO: 16, wherein the peptide is pegylated at position 11 for SEQ ID NO: 9 and SEQ ID NO: 13, pegylated at position 16 for SEQ ID NO: 10, and pegylated at position 19 for SEQ ID NO: 10 and SEQ ID NO: 14. In one embodiment the glucagon agonist comprises the peptide of SEQ ID NO: 13 or SEQ ID NO: 14. In one embodiment the C-terminal amino acid of the glucagon antagonists disclosed herein have an amide group in place of the carboxylic acid group that is present on the native amino acid. In accordance with one embodiment the glucagon antagonist comprises the sequence of SEQ ID NO: 18.

In accordance with one embodiment, a glucagon antagonist is provided wherein a plasma protein has been covalently linked to an amino acid side chain of the peptide to improve the solubility, stability and/or pharmacokinetics of the glucagon peptide. For example, serum albumin can be covalently bound to the glucagon antagonists presented herein. In one embodiment the plasma protein is covalently bound to an amino acid corresponding to position 16, 17, 20, 21, 24 or 29 of the native glucagon peptide. More particularly, in one embodiment the plasmid protein is bound to an amino acid corresponding to position 16 or 24 of the native glucagon peptide, wherein the glucagon antagonist comprises the sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 36 and SEQ ID NO: 39. In one embodiment the glucagon antagonist comprises a peptide selected from the group consisting of SEQ ID NO: 9, SEQ ID NO: 10, SEQ ID NO: 11 and SEQ ID NO: 12.

In accordance with one embodiment, a glucagon antagonist is provided wherein a linear amino acid sequence representing the Fc portion of an immunoglobin molecule has been covalently linked to an amino acid side chain of a glucagon antagonist disclosed herein to improve the solubility, stability and/or pharmacokinetics of the glucagon peptide. For example, the amino acid sequence representing the Fc portion of an immunoglobin molecule can be covalently bound to position 11, 12, 15, 16, 19, 21 or 24 of the glucagon peptide of SEQ ID NO: 7, SEQ ID NO: 39, or a glucagon analog thereof. In one embodiment the Fc peptide is covalently bound to position 11 or 19 of the glucagon antagonist of SEQ ID NO: 6, SEQ ID NO: 7, SEQ ID NO: 8 or SEQ ID NO: 36. The Fc portion is usually isolated from IgG, but the Fc peptide fragment from any immunoglobin should function equivalently. In one embodiment the glucagon peptide is selected from the group consisting of SEQ ID NO: 3, SEQ ID NO: 4, SEQ ID NO: 5, SEQ ID NO: 7 SEQ ID NO: 8, and SEQ ID NO: 39, wherein the Fc portion is linked to the corresponding position of 16, 17, 20, 21, 24 or 29 of the native glucagon peptide. In one embodiment the glucagon analog comprises a glucagon peptide selected from the group consisting of SEQ ID NO: 9, SEQ ID NO: 10, SEQ ID NO: 11 and SEQ ID NO: 12, wherein the Fc peptide is bound to the side chain of the amino acid located at position 11, 16 or 19 of SEQ ID NO: 9, SEQ ID NO: 10, SEQ ID NO: 11, respectively, and at both positions 11 and 19 for SEQ ID NO: 12.

The present disclosure also encompasses other conjugates in which glucagon peptides of the invention are linked, optionally via covalent bonding and optionally via a linker, to a conjugate. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

Exemplary conjugates include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising a glucagon peptide of the present invention and a plasma protein, wherein the plasma protein is selected form the group consisting of albumin, transferin, fibrinogen and glubulins. In one embodiment the plasma protein moiety of the conjugate is albumin or transferin. In some embodiments, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

The Asp-Ser sequence at position 15-16 of native glucagon has been identified as a uniquely unstable dipeptide that leads to premature chemical cleavage of the native hormone in aqueous buffers. For example, when maintained at 0.01N HCl at 37° C. for 2 weeks, more than 50% of the native glucagon may be cleaved into fragments. The two liberated cleavage peptides 1-15 and 16-29 are devoid of glucagon-like biological activity and thus represent a limitation on the aqueous pre-formulation of glucagon and its related analogs. The selective chemical substitution of the Asp at position 15 of the native glucagon peptide with Glu has been observed to virtually eliminate chemical cleavage of the 15-16 peptide bond.

Accordingly, it is expected that the glucagon antagonists of the present invention can be similarly modified to decrease their susceptibility to premature chemical cleavage in aqueous buffers. In accordance with one embodiment the glucagon antagonists described herein can be further modified to enhance their stability in aqueous solutions by replacing the native aspartic amino acid, located at position 15 of the native glucagon peptide, with an amino acid selected from the group consisting of cysteic acid; glutamic acid, homoglutamic acid and homocysteic acid. In accordance with one embodiment the aspartic acid residue at position 10 of the glucagon antagonist of SEQ ID NO: 39 can be substituted with an amino acid selected from the group consisting of cysteic acid, glutamic acid, homoglutamic acid and homocysteic acid, and in one embodiment the native aspartic acid at position 10 of SEQ ID NO: 39 is replaced with glutamic acid. In accordance with one embodiment a glucagon antagonist having improved stability in aqueous solutions is provided wherein the antagonist comprises a sequence selected from the group consisting of SEQ ID NO: 36, SEQ ID NO: 40 and SEQ ID NO: 42. In a further embodiment the glucagon antagonist is amidated.

In accordance with one embodiment, increased stability by way of reduced degradation of the glucagon antagonist described herein may also be achieved by substitution of the serine at position 16 (according to the numbering of native glucagon) with glutamic acid, cysteic acid, homo-glutamic acid, or homo-cysteic acid. In a specific embodiment, the serine at position 16 (according to the native glucagon sequence numbering) is replaced with glutamic acid. In a more specific aspect, the glucagon antagonist comprising such a modification comprises a C-terminal carboxylate and is not amidated.

In accordance with one embodiment, a glucagon antagonist is provided comprising a glucagon peptide selected from the group consisting of SEQ ID NO: 7, SEQ ID NO: 36, SEQ ID NO: 39, SEQ ID NO: 40, SEQ ID NO: 41, SEQ ID NO: 42, SEQ ID NO: 43 and SEQ ID NO: 44, further modified by one or more additional amino acid substitutions at positions corresponding to positions 11, 12, 15, 16, 19 and/or 24 of the native glucagon peptide, wherein the amino acid substitutions comprise a substitution with an amino acid having a side chain suitable for crosslinking with hydrophilic moieties, including for example, PEG. The native glucagon peptide can be substituted with a naturally occurring amino acid or a synthetic (non-naturally occurring) amino acid. Synthetic or non-naturally occurring amino acids refer to amino acids that do not naturally occur in vivo but which, nevertheless, can be incorporated into the peptide structures described herein. In one embodiment a glucagon antagonist is provided wherein the peptide comprises the sequence of SEQ ID NO: 7, SEQ ID NO: 36, SEQ ID NO: 39, SEQ ID NO: 40, SEQ ID NO: 41, SEQ ID NO: 42, SEQ ID NO: 43 and SEQ ID NO: 44, and further comprises a polyethylene chain bound to corresponding position 21 or 24 of the native glucagon peptide. In a further embodiment the C-terminus of the glucagon peptide is modified to replace the carboxylic acid group with an amide group.

Applicants have also discovered that native glucagon can be modified by introducing charge at its carboxy terminus to enhance the solubility of the peptide while retaining the agonist properties of the peptide. The enhanced solubility allows for the preparation and storage of glucagon solutions at near neutral pH. Formulating glucagon solutions at relatively neutral pHs (e.g. pH of about 6.0 to about 8.0) improves the long term stability of the glucagon peptides.

Again, applicants anticipate that the glucagon antagonists disclosed herein can be similarly modified to enhance their solubility in aqueous solutions at relatively neutral pH (e.g. pH of about 6.0 to about 8.0) while retaining the antagonist properties of the parent protein. Accordingly, one embodiment of the present invention is directed to a glucagon antagonist of SEQ ID NO: 39 that has been further modified relative to the native amino acids present at positions 6-29 of the wild type glucagon (SEQ ID NO: 1) to add charge to the peptide by the substitution of native non-charged amino acids with charged amino acids, or the addition of charged amino acids to the carboxy terminus. In accordance with one embodiment, one to three of the non-charged native amino acids of the glucagon antagonist of SEQ ID NO: 39 are replaced with a charged amino acid. In one embodiment the charged amino acid is selected from the group consisting of lysine, arginine, histidine, aspartic acid and glutamic acid. More particularly, applicants have discovered that substituting the normally occurring amino acid at corresponding position 28 and/or 29 relative to native glucagon with charged amino acids, and/or the addition of one to two charged amino acids at the carboxy terminus of the glucagon peptide, enhances the solubility and stability of the glucagon peptides in aqueous solutions at physiologically relevant pHs (i.e., a pH of about 6.5 to about 7.5). Accordingly, such modifications of the glucagon antagonist disclosed herein are anticipated to have a similar effect on the solubility in aqueous solutions, particularly at a pH ranging from about 5.5 to about 8.0, while retaining the parent peptide's biological activity In accordance with one embodiment the glucagon antagonist of SEQ ID NO: 39 is modified by the substitution of the native amino acid at corresponding position 28 and/or 29 relative to native glucagon with a negatively charged amino acid (e.g., aspartic acid or glutamic acid) and optionally the addition of a negatively charged amino acid (e.g., aspartic acid or glutamic acid) to the carboxy terminus of the peptide. In an alternative embodiment the native glucagon peptide of SEQ ID NO: 39 is modified by the substitution of the native amino acid at corresponding position 29 relative to native glucagon with a positively charged amino acid (e.g., lysine, arginine or histidine) and optionally the addition of one or two positively charged amino acid (e.g., lysine, arginine or histidine) on the carboxy terminus of the peptide. In accordance with one embodiment a glucagon analog having improved solubility and stability is provided wherein the analog comprises the amino acid sequence of SEQ ID NO: 41 with the proviso that at least one amino acids at position, 23, or 24 of SEQ ID NO: 41 is substituted with an acidic amino acid, and/or an additional acidic amino acid is added at the carboxy terminus of SEQ ID NO: 41. In one embodiment the acidic amino acids are independently selected from the group consisting of Asp, Glu, cysteic acid and homocysteic acid.

In accordance with one embodiment a glucagon antagonist having improved solubility and stability is provided wherein the antagonist comprises the amino acid sequence of SEQ ID NO: 41, SEQ ID NO: 42, SEQ ID NO: 43 or SEQ ID NO: 44, wherein at least one of the amino acids at positions 23 or 24 is substituted with a non-native amino acid residue (i.e. at least one amino acid present at position 23 or 24 of the analog is an acidic amino acid different from the amino acid present at the corresponding position in SEQ ID NO: 7). In accordance with one embodiment a glucagon agonist is provided comprising the sequence of SEQ ID NO: 41 or 42 with the proviso that when the amino acid at position 23 is asparagine and the amino acid at position 24 is threonine, the peptide further comprises one to two amino acids, independently selected from the group consisting of Lys, Arg, His, Asp or Glu, added to the carboxy terminus of the glucagon antagonist.

The present disclosure also encompasses glucagon antagonist fusion peptides wherein a second peptide has been fused to the c-terminus of the glucagon antagonist. More particularly, the fusion peptide may comprise a glucagon antagonist peptide of SEQ ID NO: 44 that further comprises an amino acid sequence of SEQ ID NO: 19 (GPSSGAPPPS), SEQ ID NO: 20. (Lys Arg Asn Arg Asn Asn Ile Ala) or SEQ ID NO: 21 (Lys Arg Asn Arg) linked to the c-terminal amino acid of the glucagon antagonist. In one embodiment the amino acid sequence of SEQ ID NO: 19 (GPSSGAPPPS) is bound to amino acid 24 of the glucagon antagonist of SEQ ID NO: 42 through a peptide bond. In another embodiment the fusion peptide comprises a glucagon antagonist peptide of SEQ ID NO: 7, SEQ ID NO: 36, SEQ ID NO: 39, SEQ ID NO: 40, SEQ ID NO: 41 or SEQ ID NO: 43 that further comprises an amino acid sequence of SEQ ID NO: 19 (GPSSGAPPPS) linked to amino acid 24 of the glucagon antagonist. In another embodiment the fusion peptide comprises a glucagon antagonist peptide of SEQ ID NO: 7, SEQ ID NO: 36, SEQ ID NO: 37, SEQ ID NO: 38, SEQ ID NO: 39, SEQ ID NO: 41 or SEQ ID NO: 43 that further comprises an amino acid sequence of SEQ ID NO: 20, SEQ ID NO: 21 or SEQ ID NO: 53 linked to amino acid 24 of the glucagon antagonist. In one embodiment the glucagon antagonist fusion peptide comprises a sequence selected from the group consisting of SEQ ID NO: 46 and SEQ ID NO 47. In a further embodiment the C-terminus of the fusion peptide is modified to replace the carboxylic acid group with an amide group.

In one embodiment a glucagon antagonist fusion peptide is provided wherein the glucagon antagonist portion of the fusion peptide is selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 10, SEQ ID NO: 16, SEQ ID NO: 17, SEQ ID NO: 18 and SEQ ID NO: 39 and the sequence of SEQ ID NO: 19 is fused to the carboxy terminus of the glucagon antagonist portion, and wherein the PEG chain, when present, is selected from the range of 500 to 40,000 Daltons. More particularly, in one embodiment the glucagon antagonist segment is selected from the group consisting of SEQ ID NO: 13, SEQ ID NO: 14, SEQ ID NO: 15, SEQ ID NO: 16, SEQ ID NO: 46 and SEQ ID NO: 47 wherein the PEG chain is selected from the range of about 500 to about 5,000 Daltons, and more particularly, in one embodiment the PEG chain is about 1,000 Daltons. In a further embodiment the C-terminus is modified to replace the carboxylic acid group with an amide group.

The glucagon antagonist may further comprise one to two charged amino acids added to the carboxy terminus. In one embodiment, wherein one to two charged amino acids are added to the carboxy terminus of SEQ ID. NO: 44, the amino acids are negatively charged amino acids, including for example glutamic acid and aspartic acid. In one embodiment, the glucagon antagonist comprises the sequence of SEQ ID NO: 42 wherein at least one of corresponding positions 27 and 28 relative to the native glucagon peptide comprises an amino acid selected from the group consisting of aspartic acid and glutamic acid and wherein SEQ ID NO: 42 is optionally modified to include an addition one to two negatively charged amino acids added to the carboxy terminus. In one embodiment the negatively charged amino acids are glutamic acid or aspartic acid.

In another embodiment the solubility of the glucagon antagonist of SEQ ID NO: 42 can be improved by covalently linking a hydrophilic moiety to an amino acid residue at position 11, 12, 15, 16, 19 or 24, and in one embodiment the hydrophilic moiety is linked to an amino acid at position 11, 16 or 19, and in a further embodiment the hydrophilic moiety is linked to amino acid 19. In one embodiment the hydrophilic moiety is a plasma protein or the Fc portion of an immunoglobin, and in an alternative embodiment the hydrophilic moiety is a hydrophilic hydrocarbon chain. In one embodiment the hydrophilic moiety is polyethylene glycol, having a molecular weight selected from the range of about 1,000 to about 5,000 Daltons. In another embodiment the hydrophilic moiety is polyethylene glycol, having a molecular weight of at least about 20,000 Daltons. In one embodiment the polyethylene modified glucagon antagonist comprises the amino acids sequence of SEQ ID NO: 9, SEQ ID NO: 10, SEQ ID NO: 11, SEQ ID NO: 12, SEQ ID NO: 43, SEQ ID NO: 44 or SEQ ID NO: 45.

In one embodiment, the glucagon antagonist comprises the general structure of A-B-C, wherein A is selected from the group consisting of:
(i) phenyl lactic acid (PLA);
(ii) an oxy derivative of PLA;
(iii) a peptide of 2 to 6 amino acids in which two consecutive amino acids of the peptide are linked via an ester or ether bond;

B represents amino acids i to 26 of SEQ ID NO: 1, wherein i is 3, 4, 5, 6, or 7, optionally comprising one or more amino acid modifications selected from the group consisting of:
(iv) Asp at position 9 (according to the amino acid numbering of SEQ ID NO: 1) is substituted with a Glu, a sulfonic acid derivative of Cys, homoglutamic acid, β-homoglutamic acid, or an alkylcarboxylate derivative of cysteine having the structure of:

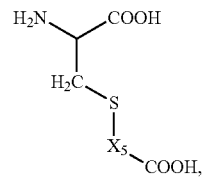

wherein $X_5$ is $C_1$-$C_4$ alkyl, $C_2$-$C_4$ alkenyl, or $C_2$-$C_4$ alkynyl.
(v) substitution of one or two amino acids at positions 10, 20, and 24, (according to the amino acid numbering of SEQ ID NO: 1) with an amino acid covalently attached to an acyl or alkyl group via an ester, ether, thioether, amide, or alkyl amine linkage;
(vi) substitution of one or two amino acids at positions 16, 17, 20, 21, and 24 (according to the amino acid numbering of SEQ ID NO: 1) with an amino acid selected from the group consisting of: Cys, Lys, ornithine, homocysteine, and acetyl-phenylalanine (Ac-Phe), wherein the amino acid of the group is covalently attached to a hydrophilic moiety;
(vii) Asp at position 15 (according to the numbering of SEQ ID NO: 1) is substituted with cysteic acid, glutamic acid, homoglutamic acid, and homocysteic acid;
(viii) Ser at position 16 (according to the numbering of SEQ ID NO: 1) is substituted with cysteic acid, glutamic acid, homoglutamic acid, and homocysteic acid;
(ix) substitution with AIB at one or more of positions 16, 20, 21, and 24 according to the amino acid numbering of SEQ ID NO: 1;
and C is selected from the group consisting of:
(x) X;
(xi) X—Y;
(xii) X—Y—Z; and
(xiii) X—Y—Z—R10,
wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid; wherein R10 is selected from a group consisting of SEQ ID NOs: 19-21 and 53; and
(xiv) any of (x) to (xiii) in which the C-terminal carboxylate is replaced with an amide.

In a specific aspect, the glucagon antagonist comprises an oxy derivative of PLA, e.g., an ester of PLA or an ether of PLA. In one embodiment, the ester of PLA comprises the structure of Formula IV:

Formula IV wherein R7 is an ester formed upon reaction of the hydroxyl of PLA with a carbonyl bearing a nucleophile.
In a specific embodiment, the oxy derivative of PLA comprises a chemical moiety selected from the group consisting of a polymer (e.g., a polyalkylene glycol), a carbohydrate, an amino acid, a peptide, and a lipid, e.g., a fatty acid or a steroid, wherein the chemical moiety is linked to PLA via an oxygen-containing bond (e.g., an ester or ether bond).

In a specific embodiment, the chemical moiety is an amino acid, which, optionally, is a part of a peptide, such that Formula IV is a depsipeptide. In this regard, PLA may be at a position other than the N-terminal amino acid residue of the glucagon antagonist, such that the glucagon antagonist comprises one or more (e.g., 1, 2, 3, 4, 5, 6, or more) amino acids N-terminal to the PLA residue. For example, the glucagon antagonist can comprise PLA at position n, wherein n is 2, 3, 4, 5, or 6 of the glucagon antagonist.

The amino acids N-terminal to the PLA residue may be synthetic or naturally-occurring. In a specific embodiment, the amino acids which are N-terminal to PLA are naturally-occurring amino acids. In one embodiment, the amino acids which are N-terminal to PLA are the N-terminal amino acids of native glucagon. For example, the glucagon antagonist can comprise at the N-terminus the amino acid sequence of any of SEQ ID NOs: 54-58, wherein PLA is linked to threonine via an ester bond:

```
SEQ ID NO: 54    His-Ser-Gln-Gly-Thr-PLA

SEQ ID NO: 55    Ser-Gln-Gly-Thr-PLA

SEQ ID NO: 56    Gln-Gly-Thr-PLA

SEQ ID NO: 57    Gly-Thr-PLA

SEQ ID NO: 58    Thr-PLA
```

In an alternative embodiment, one or more of the N-terminal amino acids may be substituted with an amino acid other than the amino acid of native glucagon. For example, when the glucagon antagonist comprises PLA as the amino acid at position 5 or 6, the amino acid at position 1 and/or position 2 may be an amino acid which reduces susceptibility to cleavage by dipeptidyl peptidase IV. More particularly, in some embodiments, position 1 of the glucagon antagonist is an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. More particularly, in some embodiments, position 2 of the antagonist peptide is an amino acid selected from the group consisting of D-serine, D-alanine, valine, glycine, N-methyl serine, N-methyl alanine, and aminoisobutyric acid (AIB). Also, for example, when the glucagon antagonist comprises PLA as the amino acid at position 4, 5, or 6, the amino acid at position 3 of the glucagon antagonist may be glutamic acid, as opposed to the native glutamine residue of native glucagon. In an exemplary embodiment of the invention, the glucagon antagonist comprises at the N-terminus the amino acid sequence of any of SEQ ID NOs: 59-61.

With respect to the glucagon antagonists comprising a compound of Formula IV, the polymer may be any polymer, provided that it can react with the hydroxyl of PLA. The polymer may be one that naturally or normally comprises a carbonyl with nucleophile, for example. Alternatively, the polymer may be one which was derivatized to comprise the carbonyl bearing a nucleophile. The polymer may be a derivatized polymer of any of: polyamides, polycarbonates, polyalkylenes and derivatives thereof including, polyalkylene glycols, polyalkylene oxides, polyalkylene terepthalates, polymers of acrylic and methacrylic esters, including poly (methyl methacrylate), poly(ethyl methacrylate), poly(butylmethacrylate), poly(isobutyl methacrylate), poly(hexyl-methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly (ethylene glycol), poly(ethylene oxide), and poly(ethylene terephthalate), and polystyrene.

The polymer can be a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly (lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

The polymer can be a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In one embodiment, the polymer is a water-soluble polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In a specific embodiment, the polymer is a polyalkylene glycol, including, for example, polyethylene glycol (PEG).

The carbohydrate may be any carbohydrate provided that it comprises or is made to comprise a carbonyl with an alpha leaving group. The carbohydrate, for example, may be one which has been derivatized to comprise a carbonyl with an alpha leaving group. In this regard, the carbohydrate may be a derivatized form of a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

With respect to the glucagon antagonists comprising a compound of Formula IV, the lipid may be any lipid comprising a carbonyl with an alpha leaving group. The lipid, for example, may be one which is derivatized to comprise the carbonyl. In this regard, the lipid, may be a derivative of a fatty acid (e.g., a $C_4$-$C_{30}$ fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide. oil, wax, cholesterol, sterol, fat-soluble vitamin, monoglyceride, diglyceride, triglyceride, a phospholipid.

In one embodiment, R7 has a molecular weight of about 40 kDa or less. Accordingly, R7 has a molecular weight of about 35 kDa or less, about 30 kDa or less, about 25 kDa or less, about 20 kDa or less, about 15 kDa or less, about 10 kDa or less, about 5 kDa or less, or about 1 kDa.

In an alternative embodiment, the glucagon antagonist comprises as A a peptide of 2 to 6 amino acids in which two consecutive amino acids of the peptide are linked via an ester or ether bond. The peptide may comprise any amino acids, synthetic or naturally occurring, provided that at least two consecutive amino acids of the peptide are linked via an ester or ether bond. In a specific embodiment, the peptide of A comprises amino acids of native glucagon. For example, the peptide can comprise j to 6 of native glucagon (SEQ ID NO: 1), wherein j is 1, 2, 3, 4, or 5. Alternatively, the peptide can comprise an amino acid sequence based on the N-terminus of SEQ ID NO: 1 with one or more amino acid modifications. For instance, the peptide can comprise at position 1 of the glucagon antagonist an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. More particularly, in some embodiments, position 2 of the antagonist peptide is an amino acid selected from the group consisting of D-serine, D-alanine, valine, glycine, N-methyl serine, N-methyl alanine, and aminoisobutyric acid (AIB). Also, for example, the amino acid at position 3 of the glucagon antagonist may be glutamic acid, as opposed to the native glutamine residue of native glucagon. Accordingly, the glucagon antagonist can comprise an amino acid sequence of:

```
Xaa₁-Xaa₂-Xaa₃-Thr-Gly-Phe;    (SEQ ID NO: 68)

Xaa₂-Xaa₃-Thr-Gly-Phe;         (SEQ ID NO: 69)
or

Xaa₃-Thr-Gly-Phe;              (SEQ ID NO: 70)
``` wherein $Xaa_1$ is selected from a group consisting of: His, D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine; $Xaa_2$ is selected from a group consisting of: Ser, D-serine, D-alanine, valine, glycine, N-methyl serine, N-methyl alanine, and aminoisobutyric acid (AIB); and $Xaa_3$ is Gln or Glu.

With regard to the glucagon antagonist comprising the general structure A-B-C, B represents amino acids of native glucagon, e.g., i to 26 of SEQ ID NO: 1, wherein i is 3, 4, 5, 6, or 7, optionally comprising one or more amino acid modifications. In a specific embodiment, B represents amino acids 7 to 26 of SEQ ID NO: 1, optionally further modified.

In one embodiment, B is modified by up to three amino acid modifications. For example, B, which represents native amino acid sequence of SEQ ID NO: 1 is modified by one or more conservative amino acid modifications.

In another embodiment, B comprises one or more amino acid modifications selected from the group consisting of (iv) to (ix), as described herein. In a specific embodiment, B comprises one or both of the amino acid modifications (v) and (vi). In a further specific embodiment, B comprises one or a combination of amino acid modifications selected from the group consisting of (iv), (vii), (viii), and (ix), in addition to (v) and (vi).

In another specific embodiment, the glucagon antagonist comprises one or more charged amino acids at the C-terminus. For example, Y and/or Z can be a charged amino acid, e.g., Lys, Arg, His, Asp, and Glu. In yet another embodiment, the glucagon antagonist comprises one to two charged amino acids (e.g., Lys, Arg, His, Asp, and Glu) C-terminal to Z. In a specific aspect, Z followed by one to two charged amino acids does not comprise R10.

The glucagon antagonist in one embodiment comprises a hydrophilic moiety covalently bound to an amino acid residue of the glucagon antagonist, as described herein. For example, the glucagon antagonist can comprise a hydrophilic moiety covalently attached to an amino acid at position 1, 16, 20, 21, or 24 according to the numbering of SEQ ID NO: 1. In another embodiment, the hydrophilic moiety is attached to the C-terminal amino acid of the glucagon antagonist, which in some cases, is 1 or 11 amino acids C-terminal to Z. In yet another embodiment, the hydrophilic moiety is attached to PLA, when A is PLA, PLA-Phe, or PLA-Thr-Phe, wherein PLA is modified to comprise the hydrophilic moiety. In another embodiment, an amino acid comprising a hydrophilic moiety is added to the N- or C-terminus of the glucagon antagonist.

In another embodiment, the glucagon antagonist comprises an acyl group or alkyl group as described herein. For example, the acylation or alkylation can occur off the side chain of the amino acid at position 10, 20, or 24, according to the numbering of SEQ ID NO: 1. In an alternative embodiment, the acylation or alkylation occurs off the side chain of the C-terminal amino acid of the glucagon antagonist, which in some cases, is 1 or 11 amino acids C-terminal to Z. In yet another embodiment, when A is PLA, PLA-Phe, or PLA-Thr-Phe, the PLA is modified to comprise an acyl or alkyl group.

In certain embodiments of the invention, the glucagon antagonist comprises the amino acid sequence of any of SEQ ID NOs: 62, 64-67, and 71.

The disclosed glucagon antagonists are believed to be suitable for any use that has previously been described for other glucagon antagonists. Accordingly, the modified glucagon peptides described herein can be used to treat hyperglycemia, or treat other metabolic diseases that result from high blood levels of glucagon or high blood glucose levels. In accordance with one embodiment the patient to be treated using the glucagon antagonists disclosed herein is a domesticated animal, and in another embodiment the patient to be treated is a human. Studies suggest that lack of glucagon suppression in diabetic patients contributes to postprandial hyperglycemia in part via accelerated glycogenolysis. Analysis of blood glucose during an Oral Glucose Tolerance Test (OGTT), and in the presence or absence of somatostatin-induced glucagon suppression, has shown a significant increase in glucose in subjects with higher glucagon levels. Accordingly, the glucagon antagonist of the present invention can be used to treat hyperglycemia, and are expected to be useful for treating a variety of types of diabetes including diabetes mellitus type I, diabetes mellitus type II, or gestational diabetes, either insulin-dependent or non-insulin-dependent, and reducing complications of diabetes including nephropathy, retinopathy and vascular disease.

Exendin-4, is a peptide made up of 39 amino acids. It is a powerful stimulator of a receptor known as GLP-1. This peptide has also been reported to suppress appetite and induce weight loss. Applicants have found that the terminal sequence of Exendin-4 when added at the carboxy terminus of glucagon improves the solubility and stability of glucagon without compromising the bioactivity of glucagon. In accordance with one embodiment the glucagon antagonist disclosed herein are administered to patients as a method of reducing appetite or promoting loss of body weight. In accordance with one embodiment the patient is a domesticated animal, and in another embodiment the patient to be treated is a human. In one embodiment the terminal ten amino acids of Exendin-4 (i.e. the sequence of SEQ ID NO: 19 (GPSSGAPPPS)) are linked to the carboxy terminus of a glucagon antagonists disclosed herein. These fusion proteins are anticipated to have pharmacological activity for suppressing appetite and inducing weight loss/weight maintenance. In accordance with one embodiment the glucagon antagonists disclosed herein can be further modified to include the amino acid sequence of SEQ ID NO: 19 (GPSSGAPPPS) linked to amino acid 24 of the glucagon antagonist of SEQ ID NO: 42 and administered to individuals to induce weight loss or assist in weight maintenance. More particularly, the glucagon peptide comprises a sequence selected from the group consisting of SEQ ID NO: 2; SEQ ID NO: 3, SEQ ID NO: 4 SEQ ID NO: 5, SEQ ID NO: 6, SEQ ID NO: 7, SEQ ID NO: 8, SEQ ID NO: 36, SEQ ID NO: 39, SEQ ID NO: 40 SEQ ID NO: 41, SEQ ID NO: 42, SEQ ID NO: 43 and SEQ ID NO: 44 and further comprising the amino acid sequence of SEQ ID NO: 19 (GPSSGAPPPS) linked to amino acid 24 of the glucagon antagonist is used to suppress appetite and inducing weight loss/weight maintenance. In one embodiment the administered glucagon antagonist comprises the sequence of SEQ ID NO: 46 or SEQ ID NO: 47.

Such methods for reducing appetite or promoting loss of body weight are expected to be useful in reducing body weight, preventing weight gain, or treating obesity of various causes, including drug-induced obesity, and reducing complications associated with obesity including vascular disease (coronary artery disease, stroke, peripheral vascular disease, ischemia reperfusion, etc.), hypertension, onset of diabetes type II, hyperlipidemia and musculoskeletal diseases.

The glucagon peptides of the invention may be administered alone or in combination with other anti-diabetic or anti-obesity agents. Anti-diabetic agents known in the art or under investigation include insulin, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to xenical (Orlistat) or Cetilistat (also known as ATL-962), or GT 389-255.

The glucagon antagonists of the present invention can also be administered to patients suffering from catabolic wasting. It is estimated that over half of cancer patients experience catabolic wasting which is characterized by unintended and progressive weight loss, weakness, and low body fat and muscle. The syndrome is equally common in AIDS patients and can also bepresent in bacterial and parasitic diseases, rheumatoid arthritis, and chronic diseases of the bowel, liver, lungs, and heart. It is usually associated with anorexia and can manifest as a condition in aging or as a result of physical trauma. Catabolic wasting is a symptom that diminishes the quality of life, worsens the underlying condition, and is a major cause of death. Applicants anticipate that the glucagon antagonists disclosed herein can be administered to patients to treat catabolic wasting.

Pharmaceutical compositions comprising the glucagon antagonists disclosed herein can be formulated and administered to patients to using standard pharmaeuctically acceptable carriers and routes of administration known to those skilled in the art. Accordingly the present disclosure also encompasses pharmaceutical compositions comprising one or more of the glucagon antagonists disclosed herein in combination with a pharmaceutically acceptable carrier. The pharmaceutical compositions may comprise the glucagon antagonists as the sole pharmaceutically active component, or the glucagon antagonists can be combined with one or more additional active agents. In accordance with one embodiment a composition is provided comprising a glucagon antagonist of the present invention and a compound that activates the GLP-1 receptor (such as GLP-1, a GLP-1 analog, an exendin-4 analog, or derivatives thereof). In accordance with one embodiment a composition is provided comprising a glucagon antagonist of the present invention and insulin or an insulin analog. Alternatively, a composition provided for inducing weight loss or preventing weight gain can be provided that comprises the sequence of SEQ ID NO: 42 further comprising the amino acid sequence of SEQ ID NO: 19 (GPSSGAPPPS) linked to amino acid 24 of SEQ ID NO: 42, and an anti-obesity peptide. Suitable anti-obesity peptides include those disclosed in U.S. Pat. Nos. 5,691,309, 6,436, 435 or US Patent application 20050176643, and including, but limited to GLP-1, GIP (Gastric Inhibitory Polypeptide), MP1, PYY, MC-4, Leptin.

In accordance with one embodiment a pharmaceutical composition is provided comprising any of the novel glucagon peptides disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain a glucagon peptide at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various containers. The compounds of the present invention can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

All therapeutic methods, pharmaceutical compositions, kits and other similar embodiments described herein contemplate that the use of the term glucagon antagonist includes all pharmaceutically acceptable salts thereof.

Pegylating glucagon antagonists can improve the aqueous solubility of the antagonists. However, increasing the length of the PEG chain, or attaching multiple PEG chains to the peptide, such that the total molecular weight of the linked PEG is greater than 5,000 Daltons, begins to delay the time action of the modified glucagon antagonist. In accordance with one embodiment, a glucagon antagonist is provided wherein the peptide comprises one or more polyethylene glycol chains, wherein the total molecular weight of the linked PEG is greater than 5,000 Daltons, and in one embodiment is greater than 10,000 Daltons. Such modified glucagon antagonists have a delayed time of activity but without loss of bioactivity. Accordingly, such compounds can be administered prophylactically to extend the effect of the administered glucagon antagonist.

In one embodiment the pegylated glucagon antagonist comprises a peptide selected from, the group consisting of SEQ ID NO: 8, SEQ ID NO: 9, SEQ ID NO: 10, SEQ ID NO: 11, SEQ ID NO: 12, SEQ ID NO: 43, SEQ ID NO: 44 and SEQ ID NO: 45, wherein the side chain of an amino acid residue at position 11, 16 or 19 of the peptide is covalently bound to one or more polyethylene glycol chains, wherein the total molecular weight of the PEG chain(s) is greater than about 10,000 Daltons. In one embodiment the molecular weight of the PEG chain(s) is greater than 10,000 and less than or equal to 40,000 Daltons. In one embodiment, the pegylated glucagon antagonist comprises the peptide of SEQ ID NO: 9 or SEQ ID NO: 43, wherein an amino acid residue at position 11 of the peptide is covalently linked to a polyethylene glycol chain having a molecular weight selected from the range of about 10,000 to about 40,000 Daltons. In one embodiment, the pegylated glucagon antagonist comprises the peptide of SEQ ID NO: 10 or SEQ ID NO: 44, wherein an amino acid residue at position 16 of the peptide is covalently linked to a polyethylene glycol chain having a molecular weight selected from the range of about 10,000 to about 40,000 Daltons. In one embodiment, the pegylated glucagon antagonist comprises the peptide of SEQ ID NO: 11 or SEQ ID NO: 45, wherein an amino acid residue at position 19 of the peptide is covalently linked to a polyethylene glycol chain having a molecular weight selected from the range of about 10,000 to about 40,000 Daltons. In another embodiment the pegylated glucagon antagonist comprises the peptide of SEQ ID NO: 13, SEQ ID NO. 14, SEQ ID NO: 15 or SEQ ID NO: 16 wherein the covalently linked PEG chain has a molecular weight of at least about 10,000 Daltons, and in one embodiment the molecular weight of the PEG is selected from the range of about 20,000 to about 40,000 Daltons. In another embodiment the pegylated glucagon agonist comprises the peptide of SEQ ID NO: 12, SEQ ID NO: 17 or SEQ ID NO: 22, wherein a PEG chain is covalently linked to the amino acid residue at position 11 and at position 19, wherein the combined molecular weight of the two PEG chains is at least about 10,000 Daltons.

The glucagon antagonists disclosed herein can be combined with other active agents, including for example, insulin, to treat diseases or conditions that are characterized by excessive glucagon activity. In one embodiment, glucagon antagonists that have been modified to be covalently bound to a PEG chain having a molecular weight of greater than 10,000 Daltons can be administered in conjunction with insulin to help to maintain stable blood glucose levels in diabetics. The glucagon antagonists of the present disclosure can be co-administered with insulin as a single composition, simultaneously administered as separate solutions, or alternatively, the insulin and the glucagon antagonist can be administered at different times relative to one another. In one embodiment the composition comprising insulin and the composition comprising the glucagon antagonist are administered within 12 hours of one another. The exact ratio of the glucagon antagonist relative to the administered insulin will be dependent in part on determining the glucagon levels of the patient, and can be determined through routine experimentation.

The present disclosure also encompasses multimers of the modified glucagon antagonists disclosed herein. Two or more of the modified glucagon peptides can be linked together using standard linking agents and procedures known to those skilled in the art. For example, dimers can be formed between two modified glucagon antagonists through the use of bifunctional thiol crosslinkers and bi-functional amine crosslinkers, particularly for glucagon antagonists that have been substituted (at positions 11, 16 or 19, for example) with cysteine, lysine ornithine, homocysteine or acetyl phenylalanine residues (e.g. SEQ ID NO: 9, SEQ ID NO: 10, SEQ ID NO: 11 and SEQ ID NO: 12). The dimer can be a homodimer or alternatively can be a heterodimer. In one embodiment the dimer is formed between two glucagon antagonists independently selected from the group consisting of SEQ ID NO: 8, SEQ ID NO: 9, SEQ ID NO: 10, SEQ ID NO: 11, SEQ ID NO: 12, SEQ ID NO: 45, SEQ ID NO: 46, or SEQ ID NO: 47, wherein the two peptides are linked to one another via a linker attached to position 11 of each peptide, 16 of each peptide, or position 19 of each peptide or any combination thereof. In one embodiment the linkage is a disulfide linkage between a Cys11 to Cys11 or a Cys19 to Cys19 or a Cys11 to Cys19 residue of the respective glucagon antagonist peptides.

Similarly, a dimer can be formed between two glucagon antagonist peptides independently selected form the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 36, SEQ ID NO: 37, SEQ ID NO: 38, SEQ ID NO: 39 and SEQ ID NO: 42 wherein the linkage is formed between amino acid positions independently selected from positions 16, 21 and 24 with respect to the native glucagon peptide.

In accordance with one embodiment a glucagon antagonist dimer is provided comprising two glucagon antagonists, each comprising the sequence of SEQ ID NO: 46, wherein the two antagonists are linked to one another by a disulfide bond through amino acid position 25. In another embodiment a glucagon antagonist dimer is provided comprising two glucagon antagonists, each comprising the sequence of SEQ ID NO: 47, wherein the two antagonists are linked to one another by a disulfide bond through amino acid position 35. In one embodiment the dimer is formed from glucagon antagonists of SEQ ID NO: 46 and SEQ ID NO: 47 wherein the amino acid at position 10 is glutamic acid.

In one embodiment the dimer comprises a homodimer of a glucagon antagonist fusion peptide selected from the group consisting of SEQ ID NO: 7, SEQ ID NO: 8, SEQ ID NO: 36, SEQ ID NO: 37, SEQ ID NO: 40, SEQ ID NO: 39, SEQ ID NO: 40, SEQ ID NO: 41, SEQ ID NO: 42 and pharmaceutically acceptable salts of said glucagon antagonists. In accordance with one embodiment a dimer is provided comprising a first glucagon antagonist bound to a second glucagon antagonist via a linker, wherein the first and second glucagon peptides of the dimer are independently selected from the group consisting of SEQ ID NO: 7, SEQ ID NO: 8, SEQ ID NO: 36, SEQ ID NO: 37, SEQ ID NO: 39, SEQ ID NO: 40, SEQ ID NO: 41, and SEQ ID NO: 42, and pharmaceutically acceptable salts of said glucagon polypeptides. In another embodiment the first and second glucagon peptides of the dimer are independently selected from the group consisting of SEQ ID NO: 7, SEQ ID NO: 8, SEQ ID NO: 36 and SEQ ID NO: 39.

In another embodiment the dimer comprises a homodimer of a glucagon antagonist selected from the group consisting of SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31. In another embodiment, a glucagon antagonist dimer is provided wherein the first and second glucagon peptides of the dimer comprise an amino acid sequence independently selected from the group consisting of SEQ ID NO: 23, SEQ ID NO: 24, SEQ ID NO: 25, SEQ ID NO: 26, SEQ ID NO: 27 and SEQ ID NO: 28. In another embodiment the dimer comprises a homodimer of a glucagon antagonist selected from the group consisting of SEQ ID NO: 9, SEQ ID NO: 11 and SEQ ID NO: 12, wherein the glucagon peptide further comprises a polyethylene glycol chain covalently bound to position 11 or 19 of the glucagon peptide.

The modified glucagon peptides of the present invention can be provided in accordance with one embodiment as part of a kit. In one embodiment a kit for administering a glucagon agonist to a patient in need thereof is provided wherein the kit comprises a modified glucagon antagonist selected from the group consisting of 1) a glucagon antagonist comprising an amino acid sequence selected from the group consisting of SEQ ID NO: 7, SEQ ID NO: 8, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43 and SEQ ID NO: 44.

2) a pegylated glucagon antagonist, wherein the PEG chain is covalently bound to position 11, 12, 15, 16, 19, 24 or 35 of a glucagon antagonist comprising an amino acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 46 and SEQ ID NO: 47, wherein the PEG chain has a molecular weight of about 500 to about 40,000 Daltons;

3) a fusion peptide comprising a glucagon antagonist selected from the group consisting of SEQ ID NO: 7, SEQ ID NO: 8, SEQ ID NO: 36, SEQ ID NO: 39, SEQ ID NO: 40, SEQ ID NO: 41, SEQ ID NO: 42, SEQ ID NO: 43 and SEQ ID NO: 44, and the peptide of SEQ ID NO: 19 fused to the terminal amino acid of said glucagon antagonist; and 4) a pegylated glucagon antagonist, further comprising an amino acid sequence of SEQ ID NO: 19 (GPSSGAPPPS) linked to the carboxy terminus of the glucagon antagonist, wherein the covalently bound PEG chain has a molecular weight of about 500 to about 40,000 Daltons.

In one embodiment the kit is provided with a device for administering the glucagon antagonist composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the glucagon antagonist composition is prepackaged within the syringe.

Incorporation of Alpha, Alpha Di-Substituted Amino Acids

In accordance with one embodiment, a glucagon antagonist is provided comprising (either by amino acid substitution or insertion) one or more α,α-disubstituted amino acids at the C-terminal portion of the glucagon peptide (around amino acids 12-29 according to the amino acid numbering of wild type glucagon). In a specific embodiment, the α,α-disubstituted amino acid is one of amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). In some embodiments, one, two, three, four or more of positions 16, 17, 18, 20, 21, 24 or 29 (according to the amino acid numbering of wild type glucagon) is substituted with an α,α-disubstituted amino acid. In a specific embodiment, one, two, three or all of positions 16, 20, 21, and 24 (according to the amino acid numbering of wild type glucagon) are substituted with AIB. In a specific aspect, wherein the glucagon antagonist comprises one or more α,α-disubstituted amino acids, e.g., AIB, the glucagon antagonist comprises a C-terminal carboxylate and is not amidated at the C-terminus.

Linkage of Hydrophilic Moieties

In one embodiment, the solubility of the glucagon antagonists disclosed herein are enhanced by the covalent linkage of a hydrophilic moiety to the peptide. Hydrophilic moieties can be attached to the glucagon antagonists under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulthydryl, thiol, triflate, tresylate, azidirine, oxirane and 5-pyridyl. If attached to the antagonist peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10)alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly(.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with some embodiments has a molecular weight selected from the range of about 500 to about 40,000 Daltons. In one embodiment the hydrophilic moiety, e.g. PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiments the hydrophilic moiety, e.g., PEG, has a molecular weight of about 20,000 to about 40,000 Daltons.

In one embodiment dextrans are used as the hydrophilic moiety. Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD.

Linear or branched polymers are contemplated. Resulting preparations of conjugates may be essentially monodisperse or polydisperse, and may have about 0.5, 0.7, 1, 1.2, 1.5 or 2 polymer moieties per antagonist peptide.

In one embodiment the hydrophilic moiety is a polyethylene glycol (PEG) chain, optionally linked to the antagonist at one or more of positions 1, 1.6, 17, 21, 24, 29 (according to the amino acid numbering of wild type glucagon), a position within a C-terminal extension, e.g., 30, or at the N- or C-terminal amino acid. In some embodiments, the native amino acid at that position is substituted with an amino acid having a side chain suitable for crosslinking with hydrophilic moieties, to facilitate linkage of the hydrophilic moiety to the antagonist. In exemplary embodiments, the native amino acid at that position is substituted with Lys, Cys, Orn, homocysteine, or acetyl-phenylalanine residue. In other embodiments, an amino acid modified to comprise a hydrophilic group is added to the peptide at the N- or C-terminus.

Conjugates and Fusions

The present disclosure also encompasses other conjugates in which glucagon antagonists of the invention are linked, optionally via covalent bonding and optionally via a linker, to a conjugate moiety. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The antagonist can be linked to conjugate moieties via direct covalent linkage by reacting targeted amino acid residues of the antagonist with an organic derivatizing agent that is capable of reacting with selected side chains or the N- or C-terminal residues of these targeted amino acids. Reactive groups on the antagonist or conjugate include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the antagonist indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-β-(5-imidozoyepropionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagines or glutamine, acetylation of the N-terminal amine, and/or amidation or esterification of the C-terminal carboxylic acid group.

Another type of covalent modification involves chemically or enzymatically coupling glycosides to the antagonist. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Exemplary conjugate moieties that can be linked to any of the glucagon antagonists described herein include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising a glucagon antagonist of the present invention and a plasma protein, wherein the plasma protein is selected form the group consisting of albumin, transferin, fibrinogen and globulins.

In some embodiments, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

As noted above, in some embodiments, the glucagon antagonists are conjugated, e.g., fused to an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol. Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

The present disclosure also encompasses glucagon fusion peptides or proteins wherein a second peptide or polypeptide has been fused to a terminus, e.g., the carboxy terminus of the glucagon antagonist. In some embodiments the second peptide added to the carboxy terminus of the glucagon antagonist is GPSSGAPPPS, KRNRNNIA or KRNR linked to amino acid 29 of the glucagon antagonist (according to the amino acid numbering of wild type glucagon). In other embodiments, the second peptide is XGPSSGAPPPS, wherein X is selected from one of the 20 common amino acids, e.g., glutamic acid, aspartic acid or glycine. In one embodiment X represents an amino acid, for example Cys, that further comprises a hydrophilic moiety covalently linked to the side chain of that amino acid. Such C-terminal extensions improve solubility and also can improve glucagon or GLP-1 activity. In some embodiments wherein the glucagon antagonist further comprises a carboxy terminal extension, the carboxy terminal amino acid of the extension ends in an amide group or an ester group rather than a carboxylic acid.

In some embodiments, e.g., in glucagon antagonists which comprise the C-terminal extension, the threonine at position 29 (according to the amino acid numbering of wild type glucagon) is replaced with a glycine. For example, a glucagon antagonist having a glycine substitution for threonine at position 29 and comprising the C-terminal extension of GPSS-GAPPPS is four times as potent at the GLP-1 receptor as native glucagon modified to comprise the same C-terminal extension. This T29G substitution can be used in conjunction with other modifications disclosed herein to enhance the affinity of the glucagon antagonists for the GLP-1 receptor.

In some embodiments an amino acid is added to the C-terminus, and the additional amino acid is selected from the group consisting of glutamic acid, aspartic acid and glycine.

The present disclosure also encompasses multimers of the modified glucagon antagonists disclosed herein. Two or more of the modified glucagon antagonists can be linked together using standard linking agents and procedures known to those skilled in the art. For example, dimers can be formed between two modified glucagon antagonists through the use of bifunctional thiol crosslinkers and bi-functional amine crosslinkers, particularly for the glucagon antagonists that have been substituted with cysteine, lysine ornithine, homocysteine or acetyl phenylalanine residues.

Acylation and Alkylation

In accordance with some embodiments, the glucagon antagonists disclosed herein are modified to comprise an acyl group or alkyl group. Acylation or alkylation can increase the half-life of the glucagon antagonists in circulation. Acylation or alkylation can advantageously delay the onset of action and/or extend the duration of action at the glucagon and/or GLP-1 receptors and/or improve resistance to proteases such as DPP-IV and/or improve solubility. In some embodiments, the potency of the acylated glucagon antagonists is comparable to the unacylated versions of the glucagon antagonists. Glucagon antagonists may be acylated or alkylated at the same amino acid position where a hydrophilic moiety is linked, or at a different amino acid position.

In some embodiments, the invention provides a glucagon antagonist modified to comprise an acyl group or alkyl group covalently linked to the amino acid at position 10 of the glucagon antagonist (according to the amino acid numbering of wild type glucagon). The glucagon antagonist may further comprise a spacer between the amino acid at position 10 of the glucagon antagonist and the acyl group or alkyl group. In some embodiments, the acyl group is a fatty acid or bile acid, or salt thereof, e.g. a C4 to C30 fatty acid, a C8 to C24 fatty acid, cholic acid, a C4 to C30 alkyl, a C8 to C24 alkyl, or an alkyl comprising a steroid moiety of a bile acid. The spacer is any moiety with suitable reactive groups for attaching acyl or alkyl groups. In exemplary embodiments, the spacer comprises an amino acid, a dipeptide, or a tripeptide, or a hydrophilic bifunctional spacer. In some embodiments, the spacer is selected from the group consisting of: Trp, Glu, Asp, Cys and a spacer comprising $NH_2(CH_2CH_2O)n(CH_2)mCOOH$, wherein m is any integer from 1 to 6 and n is any integer from 2 to 12. Such acylated or alkylated glucagon antagonists may also further comprise a hydrophilic moiety, optionally a polyethylene glycol. Any of the foregoing glucagon antagonists may comprise two acyl groups or two alkyl groups, or a combination thereof.

Acylation can be carried out at any positions within the glucagon antagonist, including any of positions 1-29, a position within a C-terminal extension, or the C-terminal amino acid, provided that glucagon antagonist activity (and optionally GLP-1 activity) is retained. Nonlimiting examples include positions 5, 10, 11, 12, 13, 14, 16, 17, 18, 19, 20, 21, 24, 27, 28, or 29 (according to the amino acid numbering of wild type glucagon). The acyl group can be covalently linked directly to an amino acid of the glucagon antagonist, or indirectly to an amino acid of the glucagon antagonist via a spacer, wherein the spacer is positioned between the amino acid of the glucagon antagonist and the acyl group. Glucagon antagonists may be acylated at the same amino acid position where a hydrophilic moiety is linked, or at a different amino acid position. Nonlimiting examples include acylation at position 10 (according to the amino acid numbering of wild type glucagon) and pegylation at one or more positions in the C-terminal portion of the glucagon antagonist, e.g., position 24, 28 or 29 (according to the amino acid numbering of wild type glucagon), within a C-terminal extension, or at the C-terminus (e.g., through adding a C-terminal Cys).

In a specific aspect of the invention, the glucagon antagonist is modified to comprise an acyl group by direct acylation of an amine, hydroxyl, or thiol of a side chain of an amino acid of the glucagon antagonist. In some embodiments, the glucagon antagonist is directly acylated through the side chain amine, hydroxyl, or thiol of an amino acid. In some embodiments, acylation is at position 10, 20, 24, or 29 (according to the amino acid numbering of wild type glucagon). In this regard, the acylated glucagon antagonist can comprise the amino acid sequence of SEQ ID NO: 2, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or thiol. In some specific embodiments of the invention, the direct acylation of glucagon antagonist occurs through the side chain amine, hydroxyl, or thiol. of the amino acid at position 10 (according to the amino acid numbering of wild type glucagon).

In some embodiments, the amino acid comprising a side chain amine is an amino acid of Formula I:

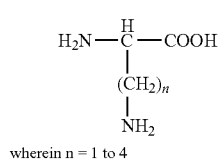

[Formula I]

wherein n = 1 to 4

In some exemplary embodiments, the amino acid of Formula I, is the amino acid wherein n is 4 (Lys) or n is 3 (Orn).

In other embodiments, the amino acid comprising a side chain hydroxyl is an amino acid of Formula II:

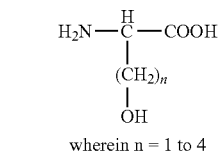

[Formula II]

wherein n = 1 to 4

In some exemplary embodiments, the amino acid of Formula II is the amino acid wherein n is 1 (Ser).

In yet other embodiments, the amino acid comprising a side chain thiol is an amino

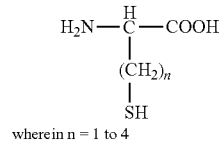
[Formula III]

wherein n = 1 to 4

In some exemplary embodiments, the amino acid of Formula II is the amino acid wherein n is 1 (Cys).

In one embodiment of the invention, the acylated glucagon antagonist comprises a spacer between the antagonist and the acyl group. In some embodiments, the glucagon antagonist is covalently bound to the spacer, which is covalently bound to the acyl group. In some exemplary embodiments, the glucagon antagonist is modified to comprise an acyl group by acylation of an amine, hydroxyl, or thiol of a spacer, which spacer is attached to a side chain of an amino acid at position 10, 20, 24, or 29 (according to the amino acid numbering of wild type glucagon), or at the C-terminal amino acid of the glucagon antagonist. The amino acid to which the spacer is attached can be any amino acid comprising a moiety which permits linkage to the spacer. For example, an amino acid comprising a side chain NH$_2$, —OH, or —COOH (e.g., Lys, Orn, Ser, Asp, or Glu) is suitable. In this respect, the acylated glucagon antagonist can comprise the amino acid sequence of SEQ ID NO: 1, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer the acylation can occur through the alpha amine of the amino acid or a side chain amine. In the instance in which the alpha amine is acylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In the instance in which the side chain amine of the spacer amino acid is acylated, the spacer amino acid is an amino acid comprising a side chain amine, e.g., an amino acid of Formula I (e.g., Lys or Orn). In this instance, it is possible for both the alpha amine and the side chain amine of the spacer amino acid to be acylated, such that the glucagon antagonist is diacylated. Embodiments of the invention include such diacylated molecules.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In one embodiment, the spacer comprises a hydrophilic bifunctional spacer. In a specific embodiment, the spacer comprises an amino poly(alkyloxy)carboxylate. In this regard, the spacer can comprise, for example, NH$_2$(CH$_2$CH$_2$O)$_n$(CH$_2$)$_m$COOH, wherein m is any integer from 1 to 6 and n is any integer from 2 to 12, such as, e.g., 8-amino-3,6-dioxaoctanoic acid, which is commercially available from Peptides International, Inc. (Louisville, Ky.).

Suitable methods of peptide acylation via amines, hydroxyls, and thiols are known in the art. See, for example, Example 19 (for methods of acylating through an amine), Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); *Bioconjugate Chem*. "Chemical Modifications of Proteins: History and Applications" pages 1, 2-12 (1990); Hashimoto et al., *Pharmacuetical Res*. "Synthesis of Palmitoyl Derivatives of Insulin and their Biological Activity" Vol. 6, No: 2 pp. 171-176 (1989).

The acyl group of the acylated glucagon antagonist can be of any size, e.g., any length carbon chain, and can be linear or branched. In some specific embodiments of the invention, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

The acylated glucagon antagonists described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the acylated glucagon antagonist can comprise SEQ ID NO: 1, including any of the modifications described herein, in which (a) at least one of the amino acids at position 10, 20, 24, and 29 (according to the amino acid numbering of wild type glucagon) comprise an acyl group and (b) at least one of the amino acids at position 16, 17, 21, 24, or 29 (according to the amino acid numbering of wild type glucagon), a position within a C-terminal extension, or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the acyl group is attached to position 10 (according to the amino acid numbering of wild type glucagon), optionally via a spacer comprising Cys, Lys, Orn, homo-Cys, or Ac-Phe, and the hydrophilic moiety is incorporated at a Cys residue at position 24 (according to the amino acid numbering of wild type glucagon).

Alternatively, the acylated glucagon antagonist can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In accordance with one embodiment, the glucagon antagonist is modified to comprise an alkyl group which is attached to the glucagon antagonist via an ester, ether, thioether, amide, or alkyl amine linkage for purposes of prolonging half-life in circulation and/or delaying the onset of and/or extending the duration of action and/or improving resistance to proteases such as DPP-IV.

Alkylation can be carried out at any positions within the glucagon antagonist, including any of positions 1-29, a position within a C-terminal extension, or the C-terminal amino acid, provided that the glucagon antagonist activity (and optionally GLP-1 activity) is retained. Nonlimiting examples include positions 5, 10, 11, 12, 13, 14, 16, 17, 18, 19, 20, 21, 24, 27, 28, or 29 (according to the amino acid numbering of wild type glucagon). The alkyl group can be covalently linked directly to an amino acid of the glucagon antagonist, or indirectly to an amino acid of the glucagon antagonist via a spacer, wherein the spacer is positioned between the amino acid of the glucagon antagonist and the alkyl group. Glucagon antagonists may be alkylated at the same amino acid position where a hydrophilic moiety is linked, or at a different amino acid position. Nonlimiting examples include alkylation at position 10 (according to the amino acid numbering of wild type glucagon) and pegylation at one or more positions in the C-terminal portion of the glucagon antagonist, e.g., position 24, 28 or 29 (according to the amino acid numbering of wild type glucagon), within a C-terminal extension, or at the C-terminus (e.g., through adding a C-terminal Cys).

In a specific aspect of the invention, the glucagon antagonist is modified to comprise an alkyl group by direct alkylation of an amine, hydroxyl, or thiol of a side chain of an amino acid of the glucagon antagonist. In some embodiments, the glucagon antagonist is directly alkylated through the side chain amine, hydroxyl, or thiol of an amino acid. In some embodiments, alkylation is at position 10, 20, 24, or 29 (according to the amino acid numbering of wild type glucagon). In this regard, the alkylated glucagon antagonist can comprise the amino acid sequence of SEQ ID NO: 2, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or thiol. In some specific embodiments of the invention, the direct alkylation of the glucagon antagonist occurs through the side chain amine, hydroxyl, or thiol of the amino acid at position 10 (according to the amino acid numbering of wild type glucagon).

In some embodiments, the amino acid comprising a side chain amine is an amino acid of Formula I. In some exemplary embodiments, the amino acid of Formula I, is the amino acid wherein n is 4 (Lys) or n is 3 (Orn).

In other embodiments, the amino acid comprising a side chain hydroxyl is an amino acid of Formula II. In some exemplary embodiments, the amino acid of Formula II is the amino acid wherein n is 1 (Ser).

In yet other embodiments, the amino acid comprising a side chain thiol is an amino acid of Formula III. In some exemplary embodiments, the amino acid of Formula II is the amino acid wherein n is 1 (Cys).

In one embodiment of the invention, the alkylated glucagon antagonist comprises a spacer between the antagonist and the alkyl group. In some embodiments, the glucagon antagonist is covalently bound to the spacer, which is covalently bound to the alkyl group. In some exemplary embodiments, the glucagon antagonist is modified to comprise an alkyl group by alkylation of an amine, hydroxyl, or thiol of a spacer, which spacer is attached to a side chain of an amino acid at position 10, 20, 24, or 29 of the glucagon antagonist (according to the amino acid numbering of wild type glucagon). The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In this respect, the alkylated glucagon antagonist can comprise the amino acid sequence of SEQ ID NO: 1, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or carboxylate.

In some embodiments, the spacer is an amino acid comprising a side chain amine, hydroxyl, or thiol or a dipeptide or tripeptide comprising an amino acid comprising a side chain amine, hydroxyl, or thiol.

When alkylation occurs through an amine group of a spacer the alkylation can occur through the alpha amine of the amino acid or a side chain amine. In the instance in which the alpha amine is alkylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In the instance in which the side chain amine of the spacer amino acid is alkylated, the spacer amino acid is an amino acid comprising a side chain amine, e.g., an amino acid of Formula I (e.g., Lys or Orn). In this instance, it is possible for both the alpha amine and the side chain amine of the spacer amino acid to be alkylated, such that the glucagon antagonist is dialkylated. Embodiments of the invention include such dialkylated molecules.

When alkylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of spacer, the amino acid or one of the amino acids of the dipeptide or tripeptide can be an amino acid of Formula III. In a specific exemplary embodiment, the amino acid is Cys.

In one embodiment, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

Suitable methods of peptide alkylation via amines, hydroxyls, and thiols are known in the art. For example, a Williamson ether synthesis can be used to form an ether linkage between the glucagon antagonist and the alkyl group. Also, a nucleophilic substitution reaction of the peptide with an alkyl halide can result in any of an ester, ether, thioether, amide, or alkyl amine linkage.

The alkyl group of the alkylated glucagon antagonist can be of any size, e.g., any length carbon chain, and can be linear or branched. In some embodiments of the invention, the alkyl group is a $C_1$ to $C_{30}$ alkyl. For example, the alkyl group can be any of a C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

The alkylated glucagon antagonists described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the alkylated glucagon antagonist can comprise SEQ ID NO: 1, or a modified amino acid sequence thereof comprising one or more of the amino acid modifications described herein, in which (a) at least one of the amino acids at position 10, 20, 24, and 29 (according to the amino acid numbering of wild type glucagon) comprise an alkyl group and (b) at least one of the amino acids at position 16, 17, 21, 24, and 29 (according to the amino acid numbering of wild type glucagon), a position within a C-terminal extension or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the alkyl group is attached to position 10 (according to the amino acid numbering of wild type glucagon), optionally via a spacer comprising Cys, Lys, Orn, homo-Cys, or Ac-Phe, and the hydrophilic moiety is incorporated at a Cys residue at position 24 (according to the amino acid numbering of wild type glucagon).

Alternatively, the alkylated glucagon antagonist can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

EXAMPLES

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

General Synthesis Protocol:

Glucagon analogs were synthesized using HBTU-activated "Fast Boc" single coupling starting from 0.2 mmole of Boc Thr(OBzl)Pam resin on a modified Applied Biosystem 430 A peptide synthesizer. Boc amino acids and HBTU were obtained from Midwest Biotech (Fishers, Ind.). Side chain protecting groups used were: Arg(Tos), Asn(Xan), Asp(OcHex), Cys(pMeBzl), His(Bom), Lys(2Cl—Z), Ser(OBzl), Thr(OBzl), Tyr(2Br—Z), and Trp(CHO). The side-chain protecting group on the N-terminal His was Boc.

Each completed peptidyl resin was treated with a solution of 20% piperidine in dimethylformamide to remove the formyl group from the tryptophan. Liquid hydrogen fluoride cleavages were performed in the presence of p-cresol and dimethyl sulfide. The cleavage was run for 1 hour in an ice bath using an HF apparatus (Penninsula Labs). After evaporation of the HF, the residue was suspended in diethyl ether and the solid materials were filtered. Each peptide was extracted into 30-70 ml aqueous acetic acid and a diluted aliquot was analyzed by HPLC [Beckman System Gold, 0.46×5 cm Zorbax C8, 1 ml/min, 45 C, 214 nm, A buffer=0.1% TFA, B=0.1% TFA/90% acetonitrile, gradient of 10% to 80% B over 10 min].

Purification was done on a FPLC over a 2.2×25 cm Kromasil C18 column while monitoring the UV at 214 nm and collecting 5 minute fractions. The homogeneous fractions were combined and lyophilized to give a product purity of >95%. The correct molecular mass and purity were confirmed using MALDI-mass spectral analysis.

General Pegylation Protocol: (Cys-Maleimido)

Typically, the glucagon Cys analog is dissolved in phosphate buffered saline (5-10 mg/ml) and 0.01 M ethylenediamine tetraacetic acid is added (10-15% of total volume). Excess (2-fold) maleimido methoxyPEG reagent (Nektar) is added and the reaction stirred at room temp while monitoring reaction progress by HPLC. After 8-24 hrs, the reaction mixture, is acidified and loaded onto a preparative reverse phase column for purification using 0.1% TFA/acetonitrile gradient. The appropriate fractions were combined and lyophilized to give the desired pegylated derivatives.

Example 1

Synthesis of Glucagon $Cys^{17}$(1-29) and Similar MonoCys Analogs 0.2 mmole Boc Thr(OBzl) Pam resin (SynChem Inc) in a 60 ml reaction vessel and the following sequence was entered and run on a modified Applied Biosystems 430A Peptide Synthesizer using FastBoc HBTU-activated single couplings.

HSQGTFTSDYSKYLDSCRAQDFVQWLMNT (SEQ ID NO: 32)

The following side chain protecting groups were used: Arg (Tos), Asp(OcHex), Asn(Xan), Cys(pMeBzl), Glu(OcHex), His(Boc), Lys(2Cl—Z), Ser(Bzl), Thr(Bzl), Trp(CHO), and Tyr(Br—Z). The completed peptidyl resin was treated with 20% piperidine/dimethylformamide to remove the Trp formyl protection then transferred to an HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and approx. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] with a small sample of the cleavage extract. The remaining extract was loaded onto a 2.2×25 cm Kromasil C18 preparative reverse phase column and an acetonitrile gradient was run using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min.

The fractions containing the purest product (48-52) were combined frozen, and lyophilized to give 30.1 mg. An HPLC analysis of the product demonstrated a purity of >90% and MALDI mass spectral analysis demonstrated the desired mass of 3429.7. Glucagon $Cys^{21}$, Glucagon $Cys^{24}$, and Glucagon $Cys^{29}$ were similarly prepared.

Example 2

Synthesis of Glucagon-Cex and Other C-Terminal Extended Analogs 285 mg (0.2 mmole) methoxybenzhydrylamine resin (Midwest Biotech) was placed in a 60 ml reaction vessel and the following sequence was entered and run on a modified Applied Biosystems 430A peptide synthesizer using FastBoc HBTU-activated single couplings.

(SEQ ID NO: 33)
HSQGTFTSDYSKYLDSRRAQDFVQWLMNTGPSSGAPPPS

The following side chain protecting groups were used: Arg (Tos), Asp(OcHex), Asn(Xan), Cys(pMeBzl), Glu(OcHex), His(Boc), Lys(2Cl—Z), Ser(Bzl), Thr(Bzl), Trp(CHO), and Tyr(Br—Z). The completed peptidyl resin was treated with 20% piperidine/dimethylformamide to remove the Trp formyl protection then transferred to HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and approx. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] on an aliquot of the cleavage extract. The extract was loaded onto a 2.2×25 cm Kromasil C18 preparative reverse phase column and an acetonitrile gradient was run for elution using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min. Fractions 58-65 were combined, frozen and lyophilized to give 198.1 mg.

HPLC analysis of the product showed a purity of greater than 95%. MALDI mass spectral analysis showed the presence of the desired theoretical mass of 4316.7 with the product as a C-terminal amide. Oxyntomodulin and oxyntomodulin-KRNR were similarly prepared as the C-terminal carboxylic acids starting with the appropriately loaded PAM-resin.

Example 3

Glucagon Cys$^{17}$ Mal-PEG-5K 15.1 mg of Glucagon Cys$^{17}$(1-29) and 27.3 mg methoxy polyethyleneglycol) maleimide avg. M.W.5000 (mPEG-Mal-5000, Nektar Therapeutics) were dissolved in 3.5 ml phosphate buffered saline (PBS) and 0.5 ml 0.01 M ethylenediamine tetraacetic acid (EDTA) was added. The reaction was stirred at room temperature and the progress of the reaction was monitored by HPLC analysis [0.46×5 cm Zorbax C8, 1 ml/min, 45 C, 214 nm (0.5 A), A=0.1% TFA, B=0.1% TFA/90% ACN, gradient=10% B to 80% B over 10 min.]. After 5 hours, the reaction mixture was loaded onto 2.2×25 cm Kromasil C18 preparative reverse phase column. An acetonitrile gradient was run on a Pharmacia FPLC while monitoring the UV wavelength at 214 nm and collecting 5 min fractions. A=0.1% TFA, B=0.1% TFA/50% acetonitrile, gradient=30% B to 100% B over 450 min. The fractions corresponding to the product were combined, frozen and lyophilized to give 25.9 mg. This product was analyzed on HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] which showed a purity of approx. 90%. MALDI (matrix assisted laser desorption ionization) mass spectral analysis showed a broad mass range (typical of PEG derivatives) of 8700 to 9500. This shows an addition to the mass of the starting glucagon peptide (3429) of approximately 5,000 a.m.u.

Example 4

Glucagon Cys$^{21}$ Mal-PEG-5K 21.6 mg of Glucagon Cys$^{21}$(1-29) and 24 mg mPEG-MAL-5000 (Nektar Therapeutics) were dissolved in 3.5 ml phosphate buffered saline (PBS) and 0.5 ml 0.01 M ethylene diamine tetraacetic acid (EDTA) was added. The reaction was stirred at room temp. After 2 hrs, another 12.7 mg of mPEG-MAL-5000 was added. After 8 hrs, the reaction mixture was loaded onto a 2.2×25 cm Vydac C18 preparative reverse phase column and an acetonitrile gradient was run on a Pharmacia FPLC at 4 ml/min while collecting 5 min fractions. A=0.1% TFA, B=0.1% TFA/50% ACN. Gradient=20% to 80% B over 450 min.

The fractions corresponding to the appearance of product were combined frozen and lyophilized to give 34 mg. Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a homogeneous product that was different than starting glucagon peptide. MALDI (matrix assisted laser desorption ionization) mass spectral analysis showed a broad mass range (typical of PEG derivatives) of 8700 to 9700. This shows an addition to the mass of the starting glucagon peptide (3470) of approximately 5,000 a.m.u.

Example 5

Glucagon Cys$^{24}$ Mal-PEG-5K 20.1 mg Glucagon C$^{24}$(1-29) and 39.5 mg mPEG-Mal-5000 (Nektar Therapeutics) were dissolved in 3.5 ml PBS with stirring and 0.5 ml 0.01 M EDTA was added. The reaction was stirred at room temp for 7 hrs, then another 40 mg of mPEG-Mal-5000 was added. After approximately 15 hr, the reaction mixture was loaded onto a 2.2×25 cm Vydac C18 preparative reverse phase column and an acetonitrile gradient was run using a Pharmacia FPLC. 5 min. fractions were collected while monitoring the UV at 214 nm (2.0 A). A buffer=0.1% TFA, B buffer=0.1% TFA/50% ACN, gradient=30% B to 100% B over 450 min. The fractions corresponding to product were combined, frozen and lyophilized to give 45.8 mg. MALDI mass spectral analysis showed a typical PEG broad signal with a maximum at 9175.2 which is approximately 5,000 a.m.u. more than Glucagon C$^{24}$ (3457.8).

Example 6

Glucagon Cys$^{24}$ Mal-PEG-20K 25.7 mg of Glucagon Cys$^{24}$(1-29) and 40.7 mg mPEG-Mal-20K (Nektar Therapeutics) were dissolved in 3.5 ml PBS with stirring at room temp. and 0.5 ml 0.01 M EDTA was added. After 6 hrs, the ratio of starting material to product was approx. 60:40 as determined by HPLC. Another 25.1 mg of mPEG-Mal-20K was added and the reaction allowed to stir another 16 hrs. The product ratio had not significantly improved, so the reaction mixture was loaded onto a 2.2×25 cm Kromasil C18 preparative reverse phase column and purified on a Pharmacia FPLC using a gradient of 30% B to 100% B over 450 min. A buffer=0.1% TFA, B buffer=0.1% TFA/50% ACN, flow=4 ml/min, and 5 min fractions were collected while monitoring the UV at 214 nm (2.0 A). The fractions containing homogeneous product were combined, frozen and lyophilized to give 25.7 mg. Purity as determined by analytical HPLC was ~90%. A MALDI mass spectral analysis showed a broad peak from 23,000 to 27,000 which is approximately 20,000 a.m.u. more than starting Glucagon $C^{24}$ (3457.8).

Example 7

Glucagon $Cys^{29}$ Mal-PEG-5K 20.0 mg of Glucagon $Cys^{29}$(1-29) and 24.7 mg mPEG-Mal-5000 (Nektar Therapeutics) were dissolved in 3.5 ml PBS with stirring at room temperature and 0.5 ml 0.01 M EDTA was added. After 4 hr, another 15.6 mg of mPEG-Mal-5000 was added to drive the reaction to completion. After 8 hrs, the reaction mixture was loaded onto a 2.2×25 cm Vydac C18 preparative reverse phase column and an acetonitrile gradient was run on a Pharmacia FPLC system. 5 min fractions were collected while monitoring the UV at 214 nm (2.0 A). A=0.1% TFA, B=0.1% TFA/50% ACN. Fractions 75-97 were combined frozen and lyophilized to give 40.0 mg of product that is different than recovered starting material on HPLC (fractions 58-63). Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a purity greater than 95%. MALDI mass spectral analysis showed the presence of a PEG component with a mass range of 8,000 to 10,000 (maximum at 9025.3) which is 5,540 a.m.u. greater than starting material (3484.8).

Example 8

Glucagon $Cys^{24}$ (2-Butyrolactone)

To 24.7 mg of Glucagon $Cys^{24}$(1-29) was added 4 ml 0.05 M ammonium bicarbonate/50% acetonitrile and 5.5 ul of a solution of 2-bromo-4-hydroxybutyric acid-γ-lactone (100 ul in 900 ul acetonitrile). After 3 hrs of stirring at room temperature, another 105 ul of lactone solution was added to the reaction mixture which was stirred another 15 hrs. The reaction mixture was diluted to 10 ml with 10% aqueous acetic acid and was loaded onto a 2.2×25 cm Kromasil C18 preparative reverse phase column. An acetonitrile gradient (20% B to 80% B over 450 min) was run on a Pharmacia FPLC while collecting 5 min fractions and monitoring the UV at 214 nm (2.0 A). Flow=4 ml/min, A=0.1% TFA, B=0.1% TFA/50% ACN. Fractions 74-77 were combined frozen and lyophilized to give 7.5 mg. HPLC analysis showed a purity of 95% and MALDI mass spect analysis showed a mass of 3540.7 or 84 mass units more than starting material. This result consistent with the addition of a single butyrolactone moiety.

SEQ ID NO: 34

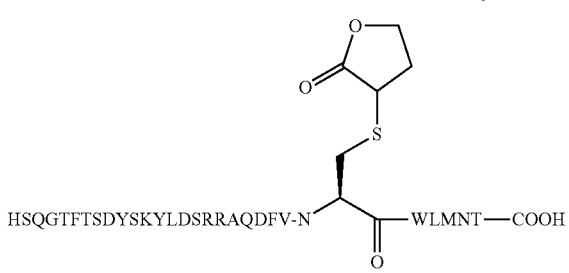

Molecular Weight = 3541.91
Exact Mass = 3538
Molecular Formula = C155H226N42O50S2

Example 9

Glucagon $Cys^{24}$(S-Carboxymethyl)

18.1 mg of Glucagon $Cys^{24}$(1-29) was dissolved in 9.4 ml 0.1 M sodium phosphate buffer (pH=9.2) and 0.6 ml bromoacetic acid solution (1.3 mg/ml in acetonitrile) was added. The reaction was stirred at room temperature and the reaction progress was followed by analytical HPLC. After 1 hr another 0.1 ml bromoacetic acid solution was added. The reaction was stirred another 60 min. then acidified with aqueous acetic acid and was loaded onto a 2.2×25 cm Kromasil C18 preparative reverse phase column for purification. An acetonitrile gradient was run on a Pharmacia FPLC (flow=4 ml/min) while collecting 5 min fractions and monitoring the UV at 214 nm (2.0 A). A=0.1% TFA, B=0.1% TFA/50% ACN. Fractions 26-29 were combined frozen and lyophilized to give several mg of product. Analytical HPLC showed a purity of 90% and MALDI mass spectral analysis confirmed a mass of 3515 for the desired product.

Example 10

Glucagon $Cys^{24}$ Maleimido, PEG-3.4K-Dimer 16 mg Glucagon $Cys^{24}$ and 1.02 mg Mal-PEG-Mal-3400, poly(ethyleneglycol)-bis-maleimide avg. M.W. 3400, (Nektar Therpeutics) were dissolved in 3.5 phosphate buffered saline and 0.5 ml 0.01 M EDTA and the reaction was stirred at room temperature. After 16 hrs, another 16 mg of Glucagon $Cys^{24}$ was added and the stirring continued. After approximately 40 hrs, the reaction mixture was loaded onto a Pharmcia PepRPC 16/10 column and an acetonitrile gradient was run on a Pharmacia FPLC while collecting 2 min fractions and monitoring the UV at 214 nm (2.0 A). Flow=2 ml/min, A=0.1% TFA, B=0.1% TFAJ50% ACN. Fractions 69-74 were combined frozen and lyophilized to give 10.4 mg. Analytical HPLC showed a purity of 90% and MALDI mass spectral analysis shows a component in the 9500-11,000 range which is consistent with the desired dimer.

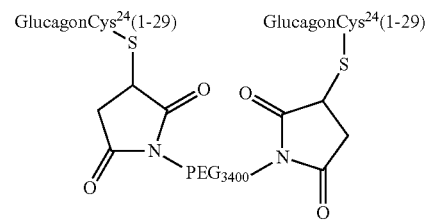

3457.80
3457.80
3572.00
10487.60

Example 11

Glucagon Solubility Assays

A solution (1 mg/ml or 3 mg/ml) of glucagon (or an analog) is prepared in 0.01N HCl. 100 ul of stock solution is diluted to 1 ml with 0.01N HCl and the UV absorbance (276 nm) is determined. The pH of the remaining stock solution is adjusted to pH7 using 200-250 ul 0.1 M $Na_2HPO_4$ (pH9.2). The solution is allowed to stand overnight at 4° C. then centrifuged. 100 ul of supernatant is then diluted to 1 ml with 0.01N HCl, and the UV absorbance is determined (in duplicate).

The initial absorbance reading is compensated for the increase in volume and the following calculation is used to establish percent solubility:

$$\frac{\text{Final Absorbance}}{\text{Initial Absorbance}} \times 100 = \text{percent soluble}$$

Results are shown in Table 1 wherein Glucagon-Cex represents wild type glucagon (SEQ ID NO: 1) plus a carboxy terminal addition of SEQ ID NO: 19 and Glucagon-Cex $R^{12}$ represents SEQ ID NO: 48.

TABLE 1

Solubility date for glucagon analogs

| Analog | Percent Soluble |
|---|---|
| Glucagon | 16 |
| Glucagon-Cex, R12 | 104 |
| Glucagon-Cex | 87 |
| Oxyntomodulin | 104 |
| Glucagon, Cys17PEG5K | 94 |
| Glucagon, Cys21PEG5K | 105 |
| Glucagon, Cys24PEG5K | 133 |

Example 12

Glucagon Receptor Binding Assay

The affinity of peptides to the glucagon receptor was measured in a competition binding assay utilizing scintillation proximity assay technology. Serial 3-fold dilutions of the peptides made in scintillation proximity assay buffer (0.05 M Tris-HCl, pH 7.5, 0.15 M NaCl, 0.1% w/v bovine serum albumin) were mixed in 96 well white/clear bottom plate (Corning Inc., Acton, Mass.) with 0.05 nM (3-[$^{125}$I]-iodotyrosyl) Tyr10 glucagon (Amersham Biosciences, Piscataway, N.J.), 1-6 micrograms per well, plasma membrane fragments prepared from cells over-expressing human glucagon receptor, and 1 mg/well polyethyleneimine-treated wheat germ agglutinin type A scintillation proximity assay beads (Amersham Biosciences, Piscataway, N.J.). Upon 5 min shaking at 800 rpm on a rotary shaker, the plate was incubated 12 h at room temperature and then read on MicroBeta1450 liquid scintillation counter (Perkin-Elmer, Wellesley, Mass.). Non-specifically bound (NSB) radioactivity was measured in the wells with 4 times greater concentration of "cold" native ligand than the highest concentration in test samples and total bound radioactivity was detected in the wells with no competitor. Percent specific binding was calculated as following: % Specific Binding=((Bound−NSB)/(Total bound−NSB))× 100. $IC_{50}$ values were determined by using Origin software (OriginLab, Northampton, Mass.).

Example 13

Functional Assay—cAMP Synthesis

The ability of glucagon analogs to induce cAMP was measured in a firefly luciferase-based reporter assay. HEK293 cells co-transfected with either glucagon- or GLP-1 receptor and luciferase gene linked to cAMP responsive element were serum deprived by culturing 16 h in DMEM (Invitrogen, Carlsbad, Calif.) supplemented with 0.25% Bovine Growth Serum (HyClone, Logan, Utah) and then incubated with serial dilutions of either glucagon, GLP-1 or novel glucagon analogs for 5 h at 37° C., 5% $CO_2$ in 96 well poly-D-Lysine-coated "Biocoat" plates (BD Biosciences, San Jose, Calif.). At the end of the incubation 100 microliters of LucLite luminescence substrate reagent (Perkin-Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). Effective 50% concentrations were calculated by using Origin software (OriginLab, Northampton, Mass. Results are shown in FIG. 3 and in Tables 2 and 3.

TABLE 2 cAMP Induction by Glucagon Analogs with C-Terminus Extension

| | cAMP Induction | | | |
|---|---|---|---|---|
| | Glucagon Receptor | | GLP-1 Receptor | |
| Peptide | $EC_{50}$, nM | N* | $EC_{50}$, nM | N* |
| Glucagon | 0.22 ± 0.09 | 14 | 3.85 ± 1.64 | 10 |
| GLP-1 | 2214.00 ± 182.43 | 2 | 0.04 ± 0.01 | 14 |
| Glucagon Cex | 0.25 ± 0.15 | 6 | 2.75 ± 2.03 | 7 |
| Oxyntomodulin | 3.25 ± 1.65 | 5 | 2.53 ± 1.74 | 5 |
| Oxyntomodulin KRNR | 2.77 ± 1.74 | 4 | 3.21 ± 0.49 | 2 |
| Glucagon R12 | 0.41 ± 0.17 | 6 | 0.48 ± 0.11 | 5 |
| Glucagon R12 Cex | 0.35 ± 0.23 | 10 | 1.25 ± 0.63 | 10 |
| Glucagon R12 K20 | 0.84 ± 0.40 | 5 | 0.82 ± 0.49 | 5 |
| Glucagon R12 K24 | 1.00 ± 0.39 | 4 | 1.25 ± 0.97 | 5 |
| Glucagon R12 K29 | 0.81 ± 0.49 | 5 | 0.41 ± 0.24 | 6 |
| Glucagon Amide | 0.26 ± 0.15 | 3 | 1.90 ± 0.35 | 2 |
| Oxyntomodulin C24 | 2.54 ± 0.63 | 2 | 5.27 ± 0.26 | 2 |
| Oxyntomodulin C24 PEG 20 K | 0.97 ± 0.04 | 1 | 1.29 ± 0.11 | 1 |

*- number of experiments

TABLE 3 cAMP Induction by Pegylated Glucagon Analogs

| | cAMP Induction | | | |
|---|---|---|---|---|
| | Glucagon Receptor | | GLP-1 Receptor | |
| Peptide | $EC_{50}$, nM | N* | $EC_{50}$, nM | N* |
| Glucagon | 0.33 ± 0.23 | 18 | 12.71 ± 3.74 | 2 |
| Glucagon C17 PEG 5 K | 0.82 ± 0.15 | 4 | 55.86 ± 1.13 | 2 |
| Glucagon C21 PEG 5 K | 0.37 ± 0.16 | 6 | 11.52 ± 3.68 | 2 |
| Glucagon C24 PEG 5 K | 0.22 ± 0.10 | 12 | 13.65 ± 2.95 | 4 |
| Glucagon C29 PEG 5 K | 0.96 ± 0.07 | 2 | 12.71 ± 3.74 | 2 |
| Glucagon C24 PEG 20 K | 0.08 ± 0.05 | 3 | Not determined | |
| Glucagon C24 Dimer | 0.10 ± 0.05 | 3 | Not determined | |
| GLP-1 | >1000 | | 0.05 ± 0.02 | 4 |

*- number of experiments

Example 14

Stability Assay for Glucagon Cys-Maleimido PEG Analogs

Each glucagon analog was dissolved in water or PBS and an initial HPLC analysis was conducted. After adjusting the pH (4, 5, 6, 7), the samples were incubated over a specified time period at 37° C. and re-analyzed by HPLC to determine the integrity of the peptide. The concentration of the specific peptide of interest was determined and the percent remaining intact was calculated relative to the initial analysis. Results for Glucagon $Cys^{21}$-maleimidoPEG$_{5K}$ are shown in FIGS. 1 and 2.

Example 15

Glucagon Antagonists

The glucagon antagonists were synthesized using the following general strategies:

General Peptide Synthesis Protocol with Boc-Chemistry Strategy:

Glucagon analogs were synthesized using HBTU-activated "Fast Boc" single coupling starting from 0.2 mmole of MBHA resin or first amino acid attached Pam resin on a modified Applied Biosystem 430A peptide synthesizer. Boc amino acids and HBTU were obtained from Midwest Biotech (Fishers, Ind.). Side chain protecting groups used were: Arg (Tos), Asn(Xan), Asp(OcHex), Cys(pMeBzl), His(Bom), Lys (2Cl—Z), Ser(OBzl), Thr(OBzl), Tyr(2Br—Z), and Trp (CHO). The N-terminal 3-phenyllacetic acid (PLA) (Aldrich, Milwaukee, Wis.) was coupled manually by BEPBT (3-(Diethoxy-phosphoryloxy)-3H-benzo[d][1,2,3]triazin-4-one, Synchem Inc., Aurora, Ohio) after the automated solid phase synthesis.

After peptide solid phase synthesis, each completed peptidyl resin was treated with 20% piperidine/DMF to remove the formyl group from the tryptophan. Liquid hydrogen fluoride cleavages were performed in the presence of p-cresol and dimethyl sulfide. The cleavage was run for 1 hour in an ice bath using an HF apparatus (Penninsula Labs). After evaporation of the HF, the residue was suspended in diethyl ether and the solid materials were filtered. Each peptide was extracted into 30-70 ml aqueous acetic acid and diluted with water and lyophilized. Crude peptide was analyzed by analytical HPLC and Peptide molecule weight was checked by ESI or MALDI-TOF mass spectrometry. Peptide was purified by the general HPLC purification procedure.

General Peptide Synthesis Protocol with Fmoc-Chemistry Strategy:

Peptides were synthesized on an ABI 433A automated peptide synthesizer using standard Fmoc chemistry with Rink MBHA amide resin or first amino acid attached Wang resin (Novabiochem, San Diego, Calif.) using DIC/HOBT as coupling reagent. 3-phenyllacetic acid (PLA) was coupled manually by BEPBT after the automated peptide synthesis. The side chain protecting groups of N-Fmoc [N-(9-fluorenyemethoxycarbonyl]amino acids were as follows: Arg, Pmc; Asp, OtBu; Cys, Trt; Gln, Trt; His, Trt; Lys, Boc; Ser, tBu, Tyr, tBu; and Trp, Boc (Pmc=2,2,5,7,8-pentamethylchroman-6-sulfonyl, OtBu=tert-butyl ester, Trt=trityl, Boc=tert-butyloxycarbonyl, and tBu=tert-butyl ester). Fmoc-Cys(SO3Na)—OH and Fmoc-homoCys(SO3Na)—OH were used for the synthesis of the cysteic acid and homocysteic acid containing peptides. Peptides were cleaved from the resin with cleavage cocktail containing 85% TFA, 5% phenol, 5% water and 5% thioanisole (2.5% EDT was added when peptide contains Cysteine). Crude peptides were precipitated in ether, centrifuged, and lyophilized. Peptide was analyzed by analytical HPLC and checked by ESI or MALDI-TOF mass spectrometry. Peptide was purified by the general HPLC purification procedure.

General Analytical HPLC Procedure:

Analytical HPLC was performed on a Beckman System Gold HPLC system with a ZORBAX SB-C8 column (0.46×5 cm, 5 µm, Agilent) with a gradient elution at a flow rate of 1.0 mL/min and monitored at 214 nm. The gradients were set up as 10% B to 80% B over 10 min and then 10% B for 5 min. Buffer A=0.1% TFA and B=0.1% TFA/90% acetonitrile.

General Preparative HPLC Purification Procedure:

The peptides were typically purified on a Waters 600E connected 486 monitor systems with semi-prepare HPLC column (ZORBAX SB-C8, 21.2×250 mm, 7 µm, Agilent) monitored at 214 nm or 230 nM. Buffer A=0.1% TFA/10% acetonitrile and B=0.1% TFA/90% acetonitrile. The gradients used for the purification were 0-30% B over 40 min, then 30-50% B over 30 min at a flow rate of 12 ml/min if not specifically noted. Fractions were analyzed by analytical HPLC and checked by mass spectrometry. The fractions over 90% pure were collected, lyophilized and stored. The fractions with purity between 60-90% were combined, lyophilized and purified again.

Pegylated glucagon analog deriviatives were prepared in accordance with the following general Cys-maleimido procedure. Typically, the glucagon Cys analog is dissolved in phosphate buffered saline (5-10 mg/ml) and 0.01 M ethylenediamine tetraacetic acid is added (10-15% of total volume). Excess (1.5~2-fold) maleimido methoxyPEG reagent (Nektar, Huntsville, Ala.) is added and the reaction stirred at room temp while monitoring reaction progress by HPLC. After 2-24 hrs, the reaction mixture, is acidified and loaded onto a preparative reverse phase column for purification using 0.1% TFA/acetonitrile gradients. The appropriate fractions were combined and lyophilized to give the desired pegylated derivatives. For peptides that exhibit low solubility in PBS, the peptides were dissolved in 25% acetonitrile water or 4-6 M urea buffer with 0.1 M Tris (adjust pH 8.0-8.5) and reacted with PEG reagents.

Specific examples of compounds synthesized by the methods described above are provided as follows:

Preparation of Fmoc-homoCys(SO$_3$Na)—OH

L-Homocysteic acid 0.92 g (5 mmole) (Sigma, St. Louis, Mo.) and 0.5 g (12.5 mmole) NaOH were dissolved in 50 ml water cooled in ice bath. A solution of 9-Fluorenylmethyl succinimidyl carbonate (Fmoc-OSu) (1.86 g, 5.5 mmole) in 50 ml dioxane was added in one portion. The mixture was stirred at room temperature for over 4 h. The mixture was evaporated under reduced pressure and 100 ml water was added. The aqueous solution was washed with ether and then passed through an ion exchange column (Amberlite IR-120B, H+form; GFS Chemicals, Columbus, Ohio)). The aqueous eluate was lyophilized to yield a viscous amorphous Fmoc-homoCys(SO$_3$H)—OH (1.6 g, 3.95 mmole, yield 79.2%). The above free acid was then added 50 ml water containing 0.16 g (4 mmole) NaOH in ice bath and lyophilized to get quantitative Fmoc-homoCys(SO$_3$Na)—OH which can be used directly in SPPS without further purification. The amorphous lyophilized Fmoc-homoCys(SO$_3$Na)—OH is recrystallined in ethanol/acetate ester(2:1) to yield a crystalline solid product with m.p. of 215-218° C. and ESI-MS 404.2 [(M−H)$^+$, acid form]

Synthesis of [PLA6, E9]Glucagon(6-29) Amide

A peptide sequence TSEYSKYLDSRRAQD-FVQWLMNT (SEQ ID NO: 51; [E3]glucagon(7-29)) was first solid phase synthesized on ABI 433A automated peptide synthesizer using 0.1 mmole Fmoc/HOBT/DCC chemistry program with 0.1 mmole Rink MBHA amide resin using DIC/HOBT as coupling reagent. The following Fmoc amino acid were used: Ala, Arg(Pmc), Asp(OtBu), Asn(Trt), Glu (OtBu), Gln(Trt), Leu, Lys(Boc), Met, PLA, Ser(tBu), Thr (tBu), Trp(Boc), Tyr(tBu), and Val. After the automated synthesis, the peptidyl resin was coupled manually with 3-phenyllacetic acid (83 mg, 0.5 mmole) and DEPBT (150 mg, 0.5 mmole) in 4 ml 5% DIEA/DMF for about 2 h to obtain the peptidyl resin with the following sequence: HO-PLA-Thr-Ser-Glu-Tyr-Ser-Lys-Tyr-Leu-Asp-Ser-Arg-Arg-Ala-Gln-Asp-Phe-Val-Gln-Trp-Leu-Met-Asn-Thr-NH$_2$ (SEQ ID NO: 50).

Peptidyl resin was treated with 8.5 ml TFA with addition of 0.5 g phenol, 0.5 ml water and 0.5 ml thioanisole at room temperature for about 2 hs. The peptide dissolved in TFA was filtered and 40 ml ether was added to precipitate the peptide. The crude peptide were centrifuged, dissolved in aqueous acetic acid and lyophilized. Crude peptide yield was 200~250 mg and after purification the yield was 25~40 mg (10~15% yield totally) peptide with 95% purity. The peptide was analyzed in general analytical HPLC showing retention time as 7.66 min and ESI-MS analysis demonstrated the desired mass of 2986.0 corresponding with the peptide molecular weight 2986.3.

Similar procedure were used to synthesize the peptide [PLA6, D9]glucagon(6-29) amide with analytical HPLC 7.25 min and ESI-MS 2973.5 corresponding to the calculated MW 2973.3; [PLA6, D9, D28]glucagon(6-29) amide with analytical HPLC 7.46 min and ESI-MS 2973.0 corresponding the calculated MW 2973.3; [PLA6, C8, E9]glucagon(6-29) amide with analytical HPLC 7.20 min and ESI-MS 3002.0 corresponding the calculated MW 3002.3; [PLA6, E9, C16]glucagon(6-29) amide with analytical HPLC 7.38 min and ESI-MS 3002.0 corresponding the calculated MW 3002.3; [PLA6, E9, C24]glucagon(6-29) amide with analytical HPLC 7.33 min and ESI-MS 2961.0 corresponding the calculated MW 2961.3; [PLA6, D9, C24]glucagon(6-29) amide with analytical HPLC 7.43 min and ESI-MS 2947.0 corresponding the calculated MW 2947.3; [PLA6, E9, C40]glucagon(6-40) amide with analytical HPLC 7.28 min and MALDI-MS 3925.5 corresponding the calculated MW 3924.3.

Synthesis of [hCys(SO3H)9]Glucagon (6-29) Amide

A peptide sequence YSKYLDSRRAQDFVQWLMNT (SEQ ID NO: 51; glucagon(10-29)) was first solid phase synthesized on ABI 433A automated peptide synthesizer using 0.1 mmole Fmoc/HOBT/DCC chemistry program with 0.1 mmole Rink MBHA amide resin using DIC/HOBT as coupling reagent. After the automated synthesis, the peptidyl resin was coupled manually with Fmoc-homoCys(SO3Na)—OH (130 mg; 0.3 mmole), HOBT (45.2 mg, 0.33 mole) and DIC (52.0 ul, 0.33 mole) in 4 ml DMF for about 2 h. After the ninhydrin test, half portion of the peptidyl resin (0.05 mmole) was further assembled automatically with the remain 3 amino acid Ser, Thr and Phe to obtain the peptidyl resin with the following sequence: $H_2$N-Phe-Thr-Ser-homoCys(SO3H)-Tyr-Ser-Lys-Tyr-Leu-Asp-Ser-Arg-Arg-Ala-Gln-Asp-Phe-Val-Gln-Trp-Leu-Met-Asn-Thr-NH2 (SEQ ID NO: 52).

The following Fmoc amino acid were used: Ala, Arg(Pmc), Asp(OtBu), Asn(Trt), Gln(Trt), homoCys(SO3Na), Leu, Lys (Boc), Met, Phe, Ser(tBu), Thr(tBu), Trp(Boc), Tyr(tBu), and Val.

Peptidyl resin was treated with 8.5 ml TFA with addition of 0.5 g phenol, 0.5 ml water and 0.5 ml thioanisole at room temperature for about 2 hs. The peptide dissolved in TFA was filtered and 40 ml ether was added to precipitate the peptide. The crude peptides were centrifuged, dissolved in aqueous acetic acid and lyophilized. Crude peptide yield was 100~130 mg, and after purification 15~20 mg (10~15% yield totally) peptide was obtained with 95% purity. The peptide was analyzed in general analytical HPLC shown retention time as 6.73 min and ESI-MS analysis demonstrated the desired mass of 3021.0 corresponding with the peptide molecular weight 3021.3.

Similar procedure to synthesize the [hCys(SO3H)9]glucagon (5-29) amide with analytical HPLC retention time 6.82 min and ESI-MS 3122.5 corresponding the calculated MW 3122.4; [hCys(SO3H)9]glucagon (4-29) amide with analytical HPLC retention time 6.83 min and ESI-MS 3178.5 corresponding the calculated MW 3179.3; [hCys(SO3H)9]glucagon (2-29) amide with analytical HPLC retention time 6.79 min and ESI-MS 3394.5 corresponding the calculated MW 3394.7; [PLA6, hCys(SO3H)9]glucagon (6-29) amide with analytical HPLC retention time 7.17 min and ESI-MS 3022.0 corresponding the calculated MW 3022.3.

Synthesis of [PLA6, E9, C24(1.2K)]Glucagon (6-29) Amide 20 mg (0.00675 mmole) [PLA6, E9, C24]glucagon (6-29) amide and 12.5 mg (0.01 mmole) m-dPEGTM24-MAL(MW 1239, Quanta biodesign Ltd. Powell, Ohio) were dissolved in 9 ml 25% acetonitrile water and 1 ml 1 M Tris base buffer (adjust pH to 8.0~8.5). The reaction was stirred at room temperature and the progress of the reaction was monitored by analytical HPLC. After no initial product was detected on HPLC (about after 2 hrs), the reaction mixture was directly purified by preparative HPLC.

After lyophilized, about 10~12 mg [PLA6, E9, C24(1.2K)] glucagon (6-29) amide was obtained which analytical HPLC analysis shown retention time as 7.48 min and ESI-MS 4218.5 corresponding the calculated [M+H2O] 4218.0.

A similar procedure was used to synthesize the [C5(1.2K), E9]glucagon (5-29) amide which analytical HPLC analysis shown retention time as 7.25 min and ESI-MS 4327.5 corresponding the calculated MW 4327.8; [C8(1.2K), E9]glucagon (6-29) amide which analytical HPLC analysis shown retention time as 7.25 min and ESI-MS 4260.0 corresponding the calculated [M+$H_2$O] 4259.0

Synthesis of [PLA6, E9, C24(20K)]Glucagon (6-29) Amide 15 mg (0.005 mmole) [PLA6, E9, C24]glucagon (6-29) amide and 140 mg (0.006 mmole) 20K mPEG-MAL(MW ~22 k, Nektar, Huntsville, Ala.) were dissolved in 9 ml 25% acetonitrile water and 1 ml 1 M Tris base buffer (adjust pH to 8.0-8.5). The reaction was stirred at room temperature and the progress of the reaction was monitored by analytical HPLC. After no initial product was detected on HPLC (about after 6 hrs), the reaction mixture was directly purified by preparative HPLC. The fractions were checked by analytical HPLC at 214 nm and also measured by UV at 280 nm. The fractions with 90% HPLC purity and also with high absorption (A280 nm=1.0~2.0) in UV measurement were combined and lyophilized. About 60~80 mg [PLA6, E9, C24(20K)]glucagon (6-29) amide can be obtained which analytical HPLC analysis shown retention time as 8.5~8.6 min and MALDI-MS shown broad mass spectrometry at 24K~26K.

A similar procedure was used to synthesize [PLA6, C8(20K), E9]glucagon (6-29) amide, [PLA6, E9, C16(20K)] glucagon (6-29) amide, [PLA6, E9, C40(20K)]glucagon (6-40) amide, [PLA6, D9, C16(20K)]glucagon (6-29) amide and [PLA6, D9, C24(20K)]glucagon (6-29) amide.

Synthesis of [PLA6, E9, C24(40K)]Glucagon (6-29) Amide 15 mg (0.005 mmole) [PLA6, E9, C24]glucagon (6-29) amide and 240 mg (0.006 mmole) 40K mPEG-MAL(MW ~40 k, Chirotech Technology Ltd., Cambs CB4 OWG, German) were dissolved in 18 ml 25% acetonitrile water and 2 ml 1 M Tris base buffer (adjust pH to 8.0-8.5). The reaction was stirred at room temperature and the progress of the reaction was monitored by analytical HPLC. After no initial product was detected on HPLC (about after 6 hrs), the reaction mixture was directly purified by preparative HPLC. The fractions were checked by analytical HPLC at 214 nm and also measured by UV at 280 nm. The fractions with 90% HPLC purity and also with high absorption (A280 nm=1.0-2.0) in UV measurement were combined and lyophilized. About 100-120 mg [PLA6, E9, C24(40K)]glucagon (6-29) amide can be obtained which analytical HPLC analysis shown retention time as 8.60~8.8 min.

A similar procedure was used to synthesize [PLA6, C8(40K), E9]glucagon (6-29) amide, [PLA6, E9, C16(40K)] glucagon (6-29) amide and [PLA6, E9, C40(40K)]glucagon (6-40) amide, [PLA6, D9, C16(40K)]glucagon (6-29) amide and [PLA6, D9, C24(40K)]glucagon (6-29) amide.

Synthesis of Dimer[PLA6, E9, C24]Glucagon (6-29) Amide 20 mg (0.00675 mmole) [PLA6, E9, C24]glucagon (6-29) amide was dissolved in 6 ml PBS buffer, 1 ml 1 M Tris base (adjust pH 8.0-8.5) and 3 ml DMSO. The reaction mixture was stirred in an open air container and monitored by analytical HPLC every 2 hr. After the initial product (HPLC RT 7.4 min) was gone and the dimer product (HPLC RT 7.9 min) was the dominate product (after 12 hr), the mixture was diluted with 0.1% TFA10% acetonitrile water and directly purified by preparative HPLC. After lyophilized about 6-8 mg Dimer [PLA6, E9, C24]glucagon (6-29) amide was obtained with ESI-MS 5920.0 corresponding the calculated MW 5920.6.

A similar procedure was used to synthesize the Dimer[C9] glucagon(6-29) amide with ESI-MS 5916.0 corresponding the calculated MW 5916.6 and Dimer[C5, E9]glucagon(5-29) amide with ESI-MS 6174.0 corresponding the calculated MW 6174.8.

Example 16

Antagonist Activities of the Glucagon Analogs

The receptor binding, cAMP induction and cAMP inhibition of glucagon and various glucagon derivative inhibitors were compared. The assays for measuring receptor binding and cAMP induction and cAMP inhibition were conducted using the assay system essentially as disclosed in Examples 12 and 13, respectively.

Specific glucagon analogs have been prepared that exhibit glucagon antagonist activity. Such compounds differ from native glucagon in that they do not possess the native N-terminal residues and have a glutamic acid substitution at position 9 relative to native glucagon. Table 4 provides glucagon receptor affinity and antagonist activity for several specific glucagon analog antagonists.

TABLE 4

Glutamic acid modified N-truncated glucagon analogs and their glucagon antagonism activities

| Peptide | Receptor Binding IC$_{50}$ (nM) | cAMP Inhibition IC$_{50}$ (nM) |
|---|---|---|
| Glucagon | 1-2.5 | N/A |
| [Glu$^9$]Glucagon(aa2-29)-NH$_2$ | 14 | partial antagonist |
| [Glu$^9$]Glucagon(aa4-29)-NH$_2$ | 136 | 128 |
| [Glu$^9$]Glucagon(aa5-29)-NH$_2$ | 37 | 74 |
| [Glu$^9$]Glucagon(aa6-29)-NH$_2$ | 36 | 97 |

Glu$^9$ is glutamic acid at position 9 according to the numbering of native glucagon As the data in Table 5 indicates, a set of hCys9-based antagonists do not perform as potently or selectively as the previously reported Glu9-based antagonists. Compounds 5B and 6B demonstrate some level of antagonism but only at concentrations that are threefold higher than their effective dose as an agonist. However, when N-terminal amino acids (in addition to the amino acid at position 1 of native glucagon) are removed, the potency of the hCys9-based glucagon antagonists is enhanced (See Table 8).

TABLE 5

Receptor Binding and cAMP Inhibition by Glucagon Antagonist Analogs

| Cmpd. # | Peptide | Receptor Binding IC$_{50}$ (nM) | cAMP Induction EC$_{50}$ (nM) | cAMP Inhibition IC$_{50}$ (nM) |
|---|---|---|---|---|
|  | Glucagon | 1.75-0.31 | 0.21 ± 0.11 | N/A |
|  | [desHis$^1$, Glu$^9$]Glucagon-NH$_2$ | 36.90 ± 0.32 | 65 ± 37 | 1862 ± 1234 |
|  | [desHis$^1$, Glu$^9$, Phe$^{25}$, Leu$^{27}$]Glucagon-NH$_2$ | 12.59 ± 0.41 | 81 ± 23 | N/A* |
| 5 | [desHis$^1$, desPhe$^6$] Glucagon-NH$_2$ | 129.55 ± 44.9 | 1178 ± 105 | N/A* |
| 6 | [desHis$^1$, Leu$^4$, Glu$^9$] Glucagon-NH$_2$ | 36.88 ± 0.03 | 318 ± 112 | 102 ± 52 |
| 4B | [desHis$^1$, hCys$^9$(SO$_3$-), Phe$^{25}$, Leu$^{27}$] Glucagon-NH$_2$ | 13.90 ± 0.37 | 430 ± 45 | N/A* |
| 5B | [desHis$^1$, desPhe$^6$, hCys$^9$(SO$_3$-), Phe$^{25}$, Leu$^{27}$] Glucagon-NH$_2$ | 53.32 ± 9.97 | 3212 ± 368 | 9217 ± 3176 |
| 6B | [desHis$^1$, Leu$^4$, hCys$^9$(SO$_3$-), Phe$^{25}$, Leu$^{27}$] Glucagon-NH$_2$ |  | 1614 ± 1132 | 4456 ± 1469 |

*not an antagonist
amino acid positions according to the numbering of native glucagon indicated by superscripted numbers Glucagon receptor binding affinity of glucagon and glucagon peptides modified by truncation of the first amino acid and by substitution at position 9 (according to the amino acid numbering of native glucagon) was analyzed as essentially described in Example 12, The results are shown in Table 6.

TABLE 6

| peptide no. | peptide | residue 9 | IC$_{50}$ (nM)$^a$ |
|---|---|---|---|
|  | Glucagon | 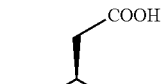 Asp | 1.50 (1.0 ~ 2.5)* |

TABLE 6-continued

| peptide no. | peptide | residue 9 | IC$_{50}$ (nM)$^a$ |
|---|---|---|---|
| 1 | [desHis$^1$, Glu$^9$]glucagon-NH$_2$ | 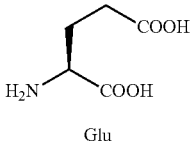 Glu | 14.08 ± 0.34 |
| 2 | [hGlu$^9$]Glucagon(aa2-29)-NH$_2$ | 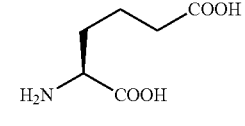 hGlu | 8.10 ± 0.40 |
| 3 | [(CSA-1)$^9$]Glucagon(aa2-29)-NH$_2$ | 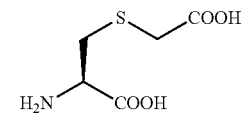 CSA-1 | 12.66 ± 0.13 |
| 4 | [(CSA-2)$^9$]Glucagon(aa2-29)-NH$_2$ | 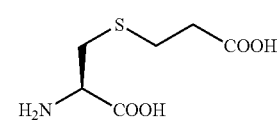 CSA-2 | 13.28 ± 0.78 |
| 5 | [β-hGlu$^9$]Glucagon(aa2-29)-NH$_2$ | 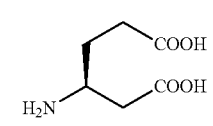 β-hGlu | 37.10 ± 0.34 |
| 6 | [(NSG-1)$^9$]Glucagon(aa2-29)-NH$_2$ | 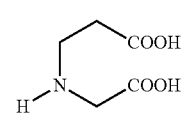 NSG-1 | 983 ± 82 |
| 7 | [(NSG-2)$^9$]Glucagon(aa2-29)-NH$_2$ | 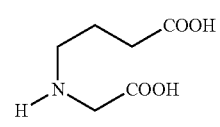 NSG-2 | 2348 ± 382 |

*EC50 (nM)
hGlu = homoglutamic acid;
amino acid positions according to the numbering of native glucagon indicated by superscripted numbers Several of the modified glucagon based peptides tested, including the peptides modified at position 9 with Glu, hGlu, CSA-1, CSA-2, and β-hGlu, exhibited potent glucagon antagonist activity.

Glucagon peptides comprising a modified amino acid at position 9 and having different extents of N-terminal truncation were analyzed for glucagon antagonist activity. The results of the peptides tested are shown in Table 7.

TABLE 7

| peptide no. | peptide | residue 9 | IC$_{50}$ (nM)$^a$ | cAMP pA$_2$$^b$ | (I/A)$_{50}$$^c$ |
|---|---|---|---|---|---|
| 8 | [Glu$^9$]Glucagon(aa4-29)-NH$_2$ | Glu | 136.0 ± 17.84 | 7.05 ± 1.01 | 1375 |
| 9 | [Leu$^4$, Glu$^9$]Glucagon(aa4-29)-NH$_2$ | Glu | 36.38 ± 8.69 | NA$^d$ | NA |
| 10 | [Glu$^9$]Glucagon(aa5-29)-NH$_2$ | Glu | 37.38 ± 3.41 | 6.94 ± 0.34 | 390 |
| 11 | [Glu$^9$]Glucagon(aa6-29)-NH$_2$ | Glu | 36.35 ± 5.23 | 7.16 ± 0.27 | 486 |
| 12 | [hGlu$^9$]Glucagon(aa6-29)-NH$_2$ | hGlu | 162.9 ± 70.8 | 6.27 ± 0.11 | 2361 |
| 13 | [(CSA-1)$^9$]Glucagon(aa6-29)-NH$_2$ | CSA-1 | 107.3 ± 5.37 | 6.68 ± 1.05 | 506 |
| 14 | [(CSA-2)$^9$]Glucagon(aa6-29)-NH$_2$ | CSA-2 | 146.4 ± 36.9 | 6.64 ± 0.29 | 580 |
| 15 | Glucagon(aa6-29)-NH$_2$ | Asp | 1894 ± 383 | 6.94 ± 0.63 | 1730 |
| 16 | [Lys$^9$]Glucagon(aa6-29)-NH$_2$ | Lys | 5779 ± 1382 | 6.58 ± 0.60 | 1990 |
| 17 | [Glu$^9$]Glucagon(aa7-29)-NH$_2$ | Glu | >10000 | ND$^e$ | ND | amino acid positions according to the numbering of native glucagon indicated by superscripted numbers
$^a$Data are average ± STD for at least three independent experiments.
$^b$pA$_2$, the negative logarithm of the concentration of the antagonist that reduce the response to 1 unit of the agonist to the response obtained from 0.5 unit of agonist. Data are average ± STD for at least two duplicate experiments.
$^c$(I/A)$_{50}$, the inhibition index, the ratio of inhibitor IC$_{50}$ to the added constant glucagon (0.1-0.2 nM). Data are average of at least three independent experiments and normalized by the EC$_{50}$
$^d$NA, not full antagonist.
$^e$ND, not detected.

FIG. 3 presents data measuring the binding affinity of glucagon antagonists, where the N-terminus was further shortened with removal of one, three or five amino acids. More particularly, the binding affinity of hCys9-based glucagon antagonists was investigated by measured based on their ability to compete with I$^{125}$ labeled glucagon in binding to the glucagon receptor. The results demonstrate that the removal of the first residue reduces affinity but further removal changes the affinity only slightly still yielding a ligand of nanomolar affinity. FIG. 4 presents data demonstrating the ability of select antagonists to suppress glucagon action in a cAMP bioassay. Surprisingly, the 5-29 hCys9-based glucagon antagonist was found to be more potent and effective than the literature standards of Glu9 2-29, or the Leu4, Glu9 4-29. Furthermore, the 5-29 or 6-29 hCys9 analogs have exhibited pure potent antagonism, without any measurable agonist activity.

Table 8 provides glucagon receptor affinity and antagonist activity for several homocysteic acid modified truncated glucagon fragment analogs. The desHis1-based hCys(SO$_3$H)$^9$-based antagonist performs as potently as the previously reported Glu$^9$-based antagonist [desHis$^1$, Glu9]glucagon peptides. The further shortened hCys(SO$_3$H)$^9$-based glucagon antagonists with removal of three, four or five amino acids were studied. The receptor binding results demonstrate that the removal of the first residue reduces affinity of the compound for the glucagon receptor, but further removal changes the affinity only slightly, and still yields a ligand of nanomolar affinity.

TABLE 8

Homocysteic acid modified truncated glucagon fragment analogs and their glucagon antagonism activities

| Peptide | IC$_{50}$ (nM) | cAMP pA$_2$ | IC$_{50}$ (nM) |
|---|---|---|---|
| Glucagon | 1.0~2.5 (EC50) | | |
| [desHis$^1$, Glu$^9$]glucagon-NH$_2$ | 14.08 ± 0.34 | NA | 1089 (partial antagonist) |
| [hCys$^9$(SO$_3$H)]Glucagon (aa2-29)-NH$_2$ | 13.16 ± 1.0 | NA | 146.6 (partial antagonist) |
| [hCys$^9$(SO$_3$H)]Glucagon (aa4-29)-NH$_2$ | 41.55 ± 4.79 | 7.22 ± 1.09 | 68.4 |
| [hCys$^9$(SO$_3$H)]Glucagon (aa5-29)-NH$_2$ | 33.85 ± 9.38 | 6.77 ± 0.33 | 98.3 |
| [hCys$^9$(SO$_3$H)]Glucagon (aa6-29)-NH$_2$ | 59.11 ± 18.10 | 7.16 ± 0.51 | 133.4 | amino acid positions according to the numbering of native glucagon indicated by superscripted numbers As shown in the data presented in FIGS. 5A and 5B, the 4-29, 5-29 and 6-29 hCys(SO$_3$H)$^9$-based peptides are surprisingly all full antagonists of glucagon action, while the 2-29 peptides were far less effective in fully suppressing glucagon activity. FIG. 5A demonstrates that the inability of the 2-29 peptides to fully suppress glucagon action is a function of the residual glucagon agonism that each of these two peptides maintains.

Specific analogs of glucagon have also been developed where the normally occurring phenylalanine at position six has been substituted with phenyl-lactic acid (PLA), on a 6-29 shortened glucagon amide backbone. PLA is isoelectronic with phenylalanine (Phe) but has no titratable hydrogen. The data presented in Tables 9 & 10 demonstrate that with the PLA6 substitution, the native Asp9 analog exhibits pure antagonism but the potency is reduced relative to that of the Glu9 and hCys(SO$_3$H)$^9$ analogs. The literature has previously, indicated that the native Asp9 residue has to be changed to Glu9 or hCys(SO$_3$H)$^9$ for high affinity and potent antagonism of glucagon (2-29) analogs. Accordingly, it is surprising that substitution of Phe with PLA on a 6-29 shortened glucagon amide backbone improves the relative antagonist potency of the analog to a point comparable to that of the Glu9 and hCys(S03H)9 analogs. More specifically, the PLA6 analog increases the affinity of the analog for the glucagon receptor threefold as well as the potency of antagonism relative to the native Phe6 analog.

TABLE 9

Residue 9 substituted glucagon (6-29) analogs and their glucagon antagonism activities

| Peptide | Residue 9 | IC$_{50}$ (nM) receptor binding | cAMP pA$_2$ | IC$_{50}$ (nM) |
|---|---|---|---|---|
| Glucagon | Asp | 1.0~2.5 | | 0.05~0.15 (EC$_{50}$) |
| [E$^9$]Glucagon(aa6-29)-NH$_2$ | Glu | 36.35 ± 5.23 | 7.16 ± 0.27 | 97.2 |
| [hCys(SO$_3$)9]Glucagon(aa6-29)-NH$_2$ | hCys(SO$_3$) | 59.11 ± 18.10 | 7.16 ± 0.51 | 133.4 |
| [hE$^9$]Glucagon(aa6-29)-NH$_2$ | hGlu | 162.9 ± 70.8 | 6.27 ± 0.11 | 472.2 |
| [C$^9$(SCH$_2$COOH)]Glucagon(aa6-29)-NH$_2$ | CSA-1 | 107.3 ± 5.37 | 6.68 ± 1.05 | 101.2 |
| [C$^9$(SCH$_2$CH$_2$COOH)]Glucagon(aa6-29)-NH$_2$ | CSA-2 | 146.4 ± 36.9 | 6.64 ± 0.29 | 116 |
| Glucagon(aa6-29)-NH2 | Asp | 1670 ± -- | 6.94 ± 0.63 | 346 |
| [K$^9$]Glucagon(aa6-29)-NH$_2$ | Lys | 3236 ± -- | 6.58 ± 0.60 | 398 | amino acid positions according to the numbering of native glucagon indicated by superscripted numbers

TABLE 10

Residue 9 substituted [PLA6]glucagon (6-29) analogs and their glucagon antagonism activities

| Peptide | IC50 (nM) (Receptor binding) | IC50 (nM) (cAMP, inhibit Glucagon) 0.1 nM or 0.2 nM | Solubility (%, pH 6-8) |
|---|---|---|---|
| Glucagon | 1.96 ± 0.61 | 0.09 (EC50) | |
| [PLA6, D9]Glucagon(aa6-29)-NH2 | 13.85 ± 3.22 | 6.90 | 11 |
| [PLA6, D9]Glucagon(aa6-29)-COOH | 15.51 ± 3.86 | 13.20 | 96 |
| [PLA6, E9]Glucagon(aa6-29)-NH2 | 12.33 ± 2.24 | 2.39 | 42.40 11 |
| [PLA6, hCys(SO3)9]Glucagon(aa6-29)-NH2 | 14.20 ± 0.45 | | 40.20 |
| [PLA6, D9, D28]Glucagon(aa6-29)-NH2 | 9.0 ± 1.24 | 1.32 | 100 |
| [PLA6, E9]Glucagon(aa6-29+CEX)-NH2 | 40.28 ± 11.29 | 24.75 | 16 | amino acid positions according to the numbering of native glucagon indicated by superscripted numbers The effect of the PLA substitution at different positions of glucagon analog, including at positions 4 and 5 was also investigated. The data presented in Table 11 and in FIG. 8 demonstrate that the PLA6 analog is an appreciably more potent antagonist than the slightly lengthened peptides. The results presented in FIG. 8 also demonstrate that acylation of the hydroxyl group does not affect the PLA6 analog potency.

TABLE 11

Analogs with PLA substitution at position 4, 5 and 6 and their glucagon antagonism activities

| Peptide | IC$_{50}$ (nM) (Receptor binding) | IC$_{50}$ (nM) (cAMP, inhibit 0.8 mM Glucagon) |
|---|---|---|
| Glucagon | 1.0-2.5 | 1.44 (EC$_{50+}$) |
| [PLA$^6$, E$^9$]Glucagon(aa6-29)-NH2 | 12.34 ± 0.13 | 64.8 ± 3.4 |
| [Ac-PLA$^6$, E$^9$]Glucagon(aa6-29)-NH2 | ND | 38.1 ± 9.2 |
| [PLA$^5$, E$^9$]Glucagon(aa5-29)-NH2 | ND | 328 ± 25 |
| [PLA$^4$, E$^9$]Glucagon(aa4-29)-NH$_2$ | ND | 84.4 ± 19.5 (partial agonist) |

ND: not detected.

amino acid positions according to the numbering of native glucagon indicated by superscripted numbers The data presented in Table 12 demonstrates that the PLA6 substitution not only increases the peptide potency but also serves a critical role in pegylation. The PLA6 analogs can be selectively pegylated without restoration of glucagon agonism. The native Phe6 analogs surprisingly demonstrate a restoration of agonism when pegylated. However this restoration of agonism is not observed in the Pla6 peptide analogs. Several specific pegylation sites were examined, including amino acid positions 8, 11 and 24 (relative to the native glucagon peptide). Pegylation at position 24 of the Pla6 analog exhibits the most potent and selective glucagon antagonism.

TABLE 12

PEGylated N-terminal truncated glucagon analogs and their glucagon antagonism activities

| Peptide | IC50 (nM) (Receptor binding) | IC50 (nM) (cAMP, inhibit 0.2 mM Glucagon) |
|---|---|---|
| [C8(20kDaPEG), E9]Glucagon(aa6-29)-NH2 | >1000 | no antagonism |
| [PLA6, C8(20kDaPEG), E9]Glucagon(aa6-29)-NH2 | 303 ± 14 | 236 |
| [E9, C11(20kDaPEG)]Glucagon(aa6-29)-NH2 | >1000 | no antagonism |
| [PLA6, E9, C11(20kDaPEG)]Glucagon(aa6-29)-NH2 | 776 ± 161 | 664 |
| [E9, C24(20kDaPEG)]Glucagon(aa6-29)-NH2 | >1000 | no antagonism |
| [PLA6, E9, C24(20kDaPEG)]Glucagon(aa6-29)-NH2 | 90 ± 7 | 126 |
| [MCA6, E9, C24(20kDaPEG)]Glucagon(aa6-29)-NH2 | 208 ± 57 | no antagonism |
| [C5(1.2kDaPEG), E9]Glucagon(aa5-29)-NH2 | 1081 ± 268 | 2281 |
| [C5(5kDaPEG), E9]Glucagon(aa5-29)-NH2 | 634 ± 174 | 1608 |
| [C5(20kDaPEG), E9]Glucagon(aa5-29)-NH2 | 331 ± 74 | 976 |
| [d-Cys5(20kDaPEG), E9]Glucagon(aa5-29)-NH2 | >10000 | 14764 |
| [K5(CH2CH2S-20kDaPEG), E9]Glucagon(aa5-29)-NH2 | >10000 | no antagonism |
| 3.4kDaPEG-dimer[C5, E9]Glucagon(aa5-29)-NH2 | 435 ± 256 | 1343 |
| [PLA6, C8(1.2kDaPEG), E9]Glucagon(aa6-29)-NH2 | 220 ± 36 | no antagonism |
| [PLA6, C8(5kDaPEG), E9]Glucagon(aa6-29)-NH2 | 948 ± 297 | 216 |
| [PLA6, C8(20kDaPEG), E9]Glucagon(aa6-29)-NH2 | 303 ± 14 | 92 |
| [PLA6, E9, C24(1.2 kDaPEG)]Glucagon(aa6-29)-NH2 | 4.7 ± 0.4 | 18 |
| [PLA6, E9, C24(20kDaPEG)]Glucagon(aa6-29)-NH2 | 90 ± 7 | 126 |
| [MCA6, E9, C24(20kDaPEG)]Glucagon(aa6-29)-NH2 | 208 ± 57 | no antagonism |
| [Phe6, E9, C24(20kDaPEG)]Glucagon(aa6-29)-NH2 | >10000 | no antagonism |

Example 17

The glucagon antagonists described herein are acylated as follows:

Acylated and/or PEGylated peptides are prepared as follows. Peptides are synthesized on a solid support resin using either a CS Bio 4886 Peptide Synthesizer or Applied Biosystems 430A Peptide Synthesizer. In situ neutralization chemistry is used as described by Schnolzer et al., *Int. J. Peptide Protein Res.* 40: 180-193 (1992). For acylated peptides, the target amino acid residue to be acylated (e.g., position ten) is substituted with an Nε-FMOC lysine residue. Treatment of the completed N-terminally BOC protected peptide with 20% piperidine in DMF for 30 minutes removes FMOC/formyl groups. Coupling to the free ε-amino Lys residue is achieved by coupling a ten-fold molar excess of either an FMOC-protected spacer amino acid (ex. FMOC-(N-BOC)-Tryptophan-OH) or acyl chain (ex. C17-COOH) and PyBOP or DEPBT coupling reagent in DMF/DIEA. Subsequent removal of the spacer amino acid's FMOC group is followed by repetition of coupling with an acyl chain. Final treatment with 100% TFA results in removal of any side chain protecting groups and the N-terminal BOC group. Peptide resins are neutralized with 5% DIEA/DMF, dried, and then cleaved from the support using HF/p-cresol, 95:5, at 0° C. for one hour. Following ether extraction, a 5% HOAc solution is used to solvate the crude peptide. A sample of the solution is then verified to contain the correct molecular weight peptide by ESI-MS. Correct peptides are purified by RP-HPLC using a linear gradient of 10% CH3CN/0.1% TFA to 0.1% TFA in 100% CH3CN. A Vydac C18 22 mm×250 mm protein column is used for the purification. Acylated peptide analogs generally complete elution by a buffer ratio of 20:80. Portions are pooled together and checked for purity on an analytical RP-HPLC. Pure fractions are lyophilized yielding white, solid peptides.

For peptide pegylation, 40 kDa methoxy poly(ethylene glycol) maleimido-propionamide (Chirotech Technology Ltd.) is reacted with a molar equivalent of peptide in 7 M Urea, 50 mM Tris-HCl buffer using the minimal amount of solvent needed to dissolve both peptide and PEG into a clear solution (generally less than 2 mL for a reaction using 2-3 mg peptide). Vigorous stirring at room temperature is commenced for 4-6 hours and the reaction is analyzed by analytical RP-HPLC. PEGylated products appear distinct from the starting material with decreased retention times. Purification is performed on a Vydac C4 column with conditions similar to those used for the initial peptide purification. Elution occurs around buffer ratios of 50:50. Fractions of pure PEGylated peptide are found and lyophilized.

Example 18

The synthesis of glucagon-based depsipeptides [Thr5-O-PLA6, E9]glucagon (2-29) amide and [Thr5-O-PLA6, E9]glucagon (1-29) amide were carried out as follows:

A peptide sequence HO-PLA-TSEYSKYLDSRRAQD-FVQWLMNT [PLA6, E9]glucagon(6-29) (SEQ ID NO: 71) was synthesized by solid-phase Boc-chemistry using an ABI 430A automated peptide synthesizer with 0.2 mmole MBHA amide resin and DEPBT as coupling reagent. The following Boc amino acids were used: Ala, Arg(Tos), Asp(OcHx), Asn (Xan), Glu(OcHx), Gln(Xan), Leu, Lys(2-Cl—Z), Met, PLA, Ser(OBzl), Thr(OBzl), Trp(HOC), Tyr(2.6-di-Cl-Bzl), and Val. To this peptide was formed a depsi-petide (ester bond) on the resin through manual coupling with a pre-activated symmetrical anhydride solution composed of Boc-Thr(OBzl)-OH (2 mmole)/DIC (1 mmole)/DMAP (0.2 mmole) in DCM for about 16 h. The remaining amino acids were coupled by standard Boc-chemistry to obtain the depsipeptidyl resin of the following sequence: Ser-Gln-Gly-Thr-O-PLA-Thr-Ser-Glu-Tyr-Ser-Lys-Tyr-Leu-Asp-Ser-Arg-Arg-Ala-Gln-Asp-Phe-Val-Gln-Trp-Leu-Met-Asn-Thr-NH$_2$ (SEQ ID NO: 64).

The peptidyl resin was treated with liquid hydrogen fluoride to cleave the crude peptide from the solid support and remove all protecting groups. The depsipeptide was purified by preparative HPLC, and analyzed by MS and analytical HPLC. The purified peptide demonstrated a single peak in analytical chromatography and the ESI-MS analysis yielded the desired mass of 3359.0 which corresponds with the calculated molecular weight of 3359.6 daltons.

A similar procedure was used to synthesize the depsipeptide [Thr5-O-PLA6, E9]glucagon (1-29) amide (SEQ ID NO: 65) with a single addition coupling of an N-terminal histidine residue. The purified peptide demonstrated a single peak in analytical chromatography and the ESI-MS analysis yielded the desired mass of 3495.9 which corresponds with the calculated molecular weight of 3496.8 daltons.

Example 19

The following peptides were synthesized as generally described above and subsequently tested for the ability to stimulate the GLP-1 receptor by assaying cAMP release from cells expressing the human GLP-1 receptor and for the ability to stimulate the glucagon receptor by assaying cAMP release from cells expressing the human glucagon receptor and stimulated with 0.5 nM glucagon, as generally described in Example 13. The results of the assays are shown in Table 13.

TABLE 13

| Peptide | Glucagon antagonism IC50(nM, inhibit 0.5 nM G) | GLP-1 agonism EC50(nM) |
| --- | --- | --- |
| Glucagon | 0.005 ± 0.008 | |
| GLP-1 | | 0.005 ± 0.002 |
| [PLA6, E9]Glucagon(6-29)<br>*PLA* TSEYSKYLDSRRAQDFVQWLMNT-NH$_2$<br>(SEQ ID NO: 71) | 23.75 ± 4.16 | No agonism |
| [PLA6, D9, D28]Glucagon(6-29)<br>*PLA* TSDYSKYLDSRRAQDFVQWLMDT-NH$_2$<br>(SEQ ID NO: 62) | 9.03 ± 1.54 | 746.0 ± 225.7 |
| [E9]Glucagon (2-29)<br>SQGTFTSEYSKYLDSRRAQDFVQWLMNT-NH$_2$<br>(SEQ ID NO: 63) | 340.0 ± 149.0 | 2719.8 ± 2136.4 |
| [Thr5-O-PLA6, E9]Glucagon(2-29)<br>SQGT(O*)FTSEYSKYLDSRRAQDFVQWLMNT-NH$_2$<br>(SEQ ID NO: 64) | 6.49 ± 2.17 | 1305.6 ± 241.5 |
| [Thr5-O-PLA6, E9]Glucagon(1-29)<br>HSQGT(O*)FTSEYSKYLDSRRAQDFVQWLMNT-NH$_2$<br>(SEQ ID NO: 65) | 14.19 ± 7.89 | 721.0 ± 35.5 |

(O*) represents a depsipeptide bond.

---

The invention claimed is:

1. A glucagon antagonist comprising the sequence of SEQ ID NO: 42, or an oxy derivative thereof.

2. The glucagon antagonist of claim 1, further comprising a hydrophilic moiety covalently bound to an amino acid residue at position 11, 16 or 19 of SEQ ID NO: 42, or at the N- or C-terminal amino acid of the glucagon antagonist, and pharmaceutically acceptable salts of said glucagon antagonist.

3. A glucagon antagonist comprising the amino acid sequence of native glucagon (SEQ ID NO: 1) modified by (i) deletion of two to five consecutive amino acid residues from the N-terminus of SEQ ID NO: 1, (ii) substitution of the aspartic acid residue at position nine of SEQ ID NO: 1 with homoglutamic acid, β-homoglutamic acid, or an alkylcarboxylate derivative of cysteine having the structure of:

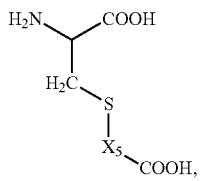

wherein $X_5$ is $C_1$-$C_4$ alkyl, $C_2$-$C_4$ alkenyl, or $C_2$-$C_4$ alkynyl;

and (iii) zero, one, two, or three further amino acid modifications relative to native glucagon (SEQ ID NO: 1).

4. The glucagon antagonist of claim 3, wherein the amino acid sequence of native glucagon is further modified by up to three amino acid modifications selected from the group consisting of:

A. substitution of one or two amino acids at positions 10, 20, and 24, according to the amino acid numbering of SEQ ID NO: 1, or the N- or C-terminal amino acid of the glucagon antagonist with an amino acid comprising an acyl or alkyl group;

B. substitution of one or two amino acids at positions 16, 17, 20, 21, and 24, according to the amino acid numbering of SEQ ID NO: 1, or the N- or C-terminal amino acid of the glucagon antagonist with an amino acid selected from the group consisting of: Cys, Lys, ornithine, homocysteine, and acetyl-phenylalanine (Ac-Phe), wherein the amino acid of the group is covalently bonded to a hydrophilic moiety;

C. addition of an amino acid covalently bonded to a hydrophilic moiety to the N- or C-terminus of the glucagon antagonist;

D. substitution of Asp at position 15, according to the numbering of SEQ ID NO: 1, with cysteic acid, glutamic acid, homoglutamic acid, and homocysteic acid;

E. substitution of Ser at position 16, according to the numbering of SEQ ID NO: 1, with cysteic acid, glutamic acid, homoglutamic acid, and homocysteic acid;
F. substitution with AIB at one or more of positions 16, 20, 21, and 24 according to the amino acid numbering of SEQ ID NO: 1;
G. deletion of the amino acid at position 29 or the amino acids at positions 28 and 29, according to the numbering of SEQ ID NO: 1;
H. substitution of each or both of the Asn at position 28 and the Thr at position 29, according to the amino acid numbering of SEQ ID NO: 1, with charged amino acids; and/or addition of one to two charged amino acids at the C-terminus of SEQ ID NO: 1;
I. substitution of the Met at position 27, according to the numbering of SEQ ID NO: 1, with Leu or norleucine;
J. addition of a peptide having the amino acid sequence of any of SEQ ID NOs: 19-21 and 53 to the C-terminus of SEQ ID NO: 1; wherein Thr at position 29, according to the numbering of SEQ ID NO: 1, is Thr or Gly; and
K. replacement of the C-terminal carboxylate with an amide or ester.

5. A glucagon antagonist comprising the general structure of A-B-C, wherein A is:
(i) phenyl lactic acid (PLA); or
(ii) an oxy derivative of PLA;
B represents amino acids i to 26 of SEQ ID NO: 1, wherein i is 3, 4, 5, 6, or 7, optionally comprising one or more amino acid modifications selected from the group consisting of:
(iv) Asp at position 9, according to the amino acid numbering of SEQ ID NO: 1, is substituted with a Glu, a sulfonic acid derivative of Cys, homoglutamic acid, β-homoglutamic acid, or an alkylcarboxylate derivative of cysteine having the structure of:

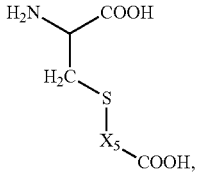

wherein $X_5$ is $C_1$-$C_4$ alkyl, $C_2$-$C_4$ alkenyl, or $C_2$-$C_4$ alkynyl;
(v) substitution of one or two amino acids at positions 10, 20, and 24, according to the amino acid numbering of SEQ ID NO: 1, with an amino acid covalently attached to an acyl or alkyl group via an ester, ether, thioether, amide, or alkyl amine linkage;
(vi) substitution of one or two amino acids at positions 16, 17, 20, 21, and 24, according to the amino acid numbering of SEQ ID NO: 1, with an amino acid selected from the group consisting of: Cys, Lys, ornithine, homocysteine, and acetyl-phenylalanine (Ac-Phe), wherein the amino acid of the group is covalently attached to a hydrophilic moiety;
(vii) Asp at position 15, according to the numbering of SEQ ID NO: 1, is substituted with cysteic acid, glutamic acid, homoglutamic acid, and homocysteic acid;
(viii) Ser at position 16, according to the numbering of SEQ ID NO: 1, is substituted with cysteic acid, glutamic acid, homoglutamic acid, and homocysteic acid; and
(ix) substitution with AIB at one or more of positions 16, 20, 21, and 24, according to the amino acid numbering of SEQ ID NO: 1;
and C is selected from the group consisting of:
(x) X;
(xi) X-Y;
(xii) X-Y-Z; and
(xiii) X-Y-Z-R10,
wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid; wherein R10 is selected from a group consisting of SEQ ID NOs: 19-21 and 53; and
(xiv) any of (x) to (xiii) in which the C-terminal carboxylate is replaced with an amide.

6. The glucagon antagonist of claim 5, wherein the oxy derivative of PLA is PLA linked to an amino acid, peptide, hydrophilic polymer, acyl group, or alkyl group via an ester bond or ether bond.

7. The glucagon antagonist of claim 5, wherein the amino acid is $Xaa_3$, or wherein the peptide comprises $Xaa_2$-$Xaa_3$ or $Xaa_1$-$Xaa_2$-$Xaa_3$, wherein $Xaa_3$ is Gln or Glu, $Xaa_2$ is selected from a group consisting of: Ser, D-serine, D-alanine, valine, glycine, N-methyl serine, N-methyl alanine, and aminoisobutyric acid (AIB); and $Xaa_1$ is selected from a group consisting of: His, D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine.

8. The glucagon antagonist of claim 5, wherein the peptide of (iii) comprises amino acids j to 6 of SEQ ID NO: 1, wherein j is 1, 2, 3, 4, or 5.

9. The glucagon antagonist of claim 5, wherein B represents amino acids 7 to 26 of SEQ ID NO: 1.

10. The glucagon antagonist of claim 5, comprising
a hydrophilic moiety covalently bound to an amino acid residue at position 16, 21, or 24, according to the numbering of SEQ ID NO: 1, or the N- or C-terminal residue of the glucagon antagonist,
an amino acid covalently attached to an acyl group or alkyl group via an ester, ether, thioether, amide, or alkyl amine linkage, wherein the amino acid is at position 10, 20, or 24, according to the amino acid numbering of SEQ ID NO: 1, or is the N- or C-terminal residue of the glucagon antagonist, or
a combination thereof.

11. The glucagon antagonist of claim 5, comprising the amino acid sequence selected from the group consisting of: SEQ ID NOs: 62, 64-67, 71, [PLA6, D9]Glucagon(aa6-29)-NH2 (SEQ ID NO: 72), [PLA6, D9]Glucagon(aa6-29)-COOH (SEQ ID NO: 73), [PLA6, E9]Glucagon(aa6-29)-NH2 (SEQ ID NO: 74), [PLA6, hCys(SO3)9]Glucagon(aa6-29)-NH2 (SEQ ID NO: 75), [PLA6, D9, D28] Glucagon(aa6-29)-NH2 (SEQ ID NO: 76), [PLA6, E9]Glucagon (aa6-29+CEX)-NH2 (SEQ ID NO: 77), [Ac-PLA$^6$, E$^9$]Glucagon(aa6-29)-NH$_2$ (SEQ ID NO: 78), [PLA$^5$ E$^9$]Glucagon(aa5-29)-NH$_2$ (SEQ ID NO: 79), [PLA$^4$, E$^9$]Glucagon(aa-4-29)-NH$_2$ (SEQ ID NO: 80), [PLA6, C8(20 kDaPEG), E9]Glucagon (aa6-29)-NH2 (SEQ ID NO: 81), [PLA6, E9, C11(20 kDaPEG)]Glucagon(aa6-29)-NH2 (SEQ ID NO: 82), [PLA6, E9, C24(20 kDaPEG)]Glucagon(aa6-29)-NH2 (SEQ ID NO: 83), [PLA6, C8(1.2 kDaPEG), E9]Glucagon(aa6-29)-NH2 (SEQ ID NO: 84), [PLA6, C8(5 kDaPEG), E9]Glucagon(aa6-29)-NH2 (SEQ ID NO: 85), [PLA6, C8(20 kDaPEG), E9]Glucagon(aa6-29)-NH2 (SEQ ID NO: 86), [PLA6, E9, C24(1.2 kDaPEG)]Glucagon(aa6-29)-NH2

(SEQ ID NO: 87), and [PLA6, E9, C24(20 kDaPEG)]Glucagon(aa6-29)-NH2 (SEQ ID NO: 88).

12. The glucagon antagonist of claim 5, comprising a Glu at position 9, according to the amino acid numbering of SEQ ID NO: 1.

13. The glucagon antagonist of claim 5, wherein C is X-Y-Z, wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid.

14. The glucagon antagonist of claim 13, wherein X is Met, Y is Asn, and Z is Thr.

15. The glucagon antagonist of claim 13, wherein X is Met, Y is a charged amino acid, and Z is Thr.

16. The glucagon antagonist of claim 15, wherein Y is Asp.

17. A peptide comprising the amino acid sequence of SEQ ID NO: 72.

18. A peptide comprising the amino acid sequence of SEQ ID NO: 73.

19. A peptide comprising the amino acid sequence of SEQ ID NO: 76.

20. A dimer or multimer comprising two or more glucagon antagonists of claim 5.

21. A conjugate comprising a glucagon antagonist of claim 5 and a heterologous peptide or polypeptide.

22. A pharmaceutical composition comprising a glucagon antagonist of claim 5 and a pharmaceutically acceptable carrier.

23. A method comprising administering to a patient an effective amount of a pharmaceutical composition of claim 22.

* * * * *

SEQUENCE LISTING

<160> NUMBER OF SEQ ID NOS: 88

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (8)..(8)
<223> OTHER INFORMATION: Xaa is aspartic acid, glutamic acid, cysteic
      acid or homocysteic acid

<400> SEQUENCE: 2

Ser Gln Gly Thr Phe Thr Ser Xaa Tyr Ser Lys Tyr Leu Asp Ser Arg
1               5                   10                  15

Arg Ala Gln Asp Phe Val Gln Trp Leu Met Asn Thr
            20                  25

```
<210> SEQ ID NO 3
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (7)..(7)
<223> OTHER INFORMATION: Xaa is aspartic acid, glutamic acid, cysteic
      acid or homocysteic acid

<400> SEQUENCE: 3

Gln Gly Thr Phe Thr Ser Xaa Tyr Ser Lys Tyr Leu Asp Ser Arg
1               5                   10                  15

Ala Gln Asp Phe Val Gln Trp Leu Met Asn Thr
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (6)..(6)
<223> OTHER INFORMATION: Xaa is aspartic acid, glutamic acid, cysteic
      acid or homocysteic acid

<400> SEQUENCE: 4

Gly Thr Phe Thr Ser Xaa Tyr Ser Lys Tyr Leu Asp Ser Arg Arg Ala
1               5                   10                  15

Gln Asp Phe Val Gln Trp Leu Met Asn Thr
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (5)..(5)
<223> OTHER INFORMATION: Xaa is aspartic acid, glutamic acid, cysteic
      acid or homocysteic acid

<400> SEQUENCE: 5

Thr Phe Thr Ser Xaa Tyr Ser Lys Tyr Leu Asp Ser Arg Arg Ala Gln
1               5                   10                  15

Asp Phe Val Gln Trp Leu Met Asn Thr
            20                  25

<210> SEQ ID NO 6
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
```

-continued

```
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is glutamic acid, cysteic acid or
      homocysteic acid
<220> FEATURE:
<221> NAME/KEY: MISC_FEATURE
<222> LOCATION: (22)..(22)
<223> OTHER INFORMATION: Xaa at position 22 is Met, Leu or Nle

<400> SEQUENCE: 6

Phe Thr Ser Xaa Tyr Ser Lys Tyr Leu Asp Ser Arg Arg Ala Gln Asp
1               5                   10                  15

Phe Val Gln Trp Leu Xaa Asn Thr
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 7

Phe Thr Ser Xaa Tyr Ser Lys Tyr Leu Asp Ser Arg Arg Ala Gln Asp
1               5                   10                  15

Phe Val Gln Trp Leu Xaa Asn Thr
            20

<210> SEQ ID NO 8
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (22)..(22)
<223> OTHER INFORMATION: Xaa is  Met, Leu or Nle
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 8

Phe Thr Ser Asp Tyr Ser Arg Tyr Leu Asp Ser Arg Arg Ala Gln Asp
1               5                   10                  15

Phe Val Gln Trp Leu Xaa Asn Thr
            20
```

```
<210> SEQ ID NO 9
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (11)..(11)
<223> OTHER INFORMATION: Xaa is Lys, Cys, Orn, homocysteine or acetyl
      phenyalanine
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 9

Phe Thr Ser Xaa Tyr Ser Xaa Tyr Leu Asp Xaa Arg Arg Ala Gln Asp
1               5                   10                  15

Phe Val Gln Trp Leu Xaa Asn Thr
            20

<210> SEQ ID NO 10
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is is Lys or Arg
<220> FEATURE:
<221> NAME/KEY: MISC_FEATURE
<222> LOCATION: (16)..(16)
<223> OTHER INFORMATION: Xaa is Lys, Cys, Orn, homocysteine or acetyl
      phenyalanine
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 10
```

-continued

Phe Thr Ser Xaa Tyr Ser Xaa Tyr Leu Asp Ser Arg Arg Ala Gln Xaa
1               5                   10                  15

Phe Val Gln Trp Leu Xaa Asn Thr
            20

<210> SEQ ID NO 11
<211> LENGTH: 24
<212> TYPE: PRT
<213> ORGANISM: Artificial Sequence
<220> FEATURE:
<223> OTHER INFORMATION: Synthetic Polypetide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (19)..(19)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 11

Phe Thr Ser Xaa Tyr Ser Xaa Tyr Leu Asp Ser Arg Arg Ala Gln Asp
1               5                   10                  15

Phe Val Xaa Trp Leu Xaa Asn Thr
            20

<210> SEQ ID NO 12
<211> LENGTH: 24
<212> TYPE: PRT
<213> ORGANISM: Artificial Sequence
<220> FEATURE:
<223> OTHER INFORMATION: Synthetic Polypetide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (11)..(11)
<223> OTHER INFORMATION: Xaa is Lys, Cys, Orn, homocysteine or acetyl
      phenylalanine
<220> FEATURE:
<221> NAME/KEY: MISC_FEATURE

```
<222> LOCATION: (19)..(19)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 12

Phe Thr Ser Xaa Tyr Ser Xaa Tyr Leu Asp Xaa Arg Arg Ala Gln Asp
1               5                   10                  15

Phe Val Xaa Trp Leu Xaa Asn Thr
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (11)..(11)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 13

Phe Thr Ser Xaa Tyr Ser Lys Tyr Leu Asp Cys Arg Arg Ala Gln Asp
1               5                   10                  15

Phe Val Gln Trp Leu Xaa Asn Thr
            20

<210> SEQ ID NO 14
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (19)..(19)
<223> OTHER INFORMATION: Pegylated
<220> FEATURE:
<221> NAME/KEY: MISC_FEATURE
```

```
<222> LOCATION: (22)..(22)
<223> OTHER INFORMATION: Xaa is Met, Leu or Nle

<400> SEQUENCE: 14

Phe Thr Ser Xaa Tyr Ser Lys Tyr Leu Asp Ser Arg Arg Ala Gln Asp
1               5                   10                  15

Phe Val Cys Trp Leu Xaa Asn Thr
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (24)..(24)
<223> OTHER INFORMATION: Pegylated

<400> SEQUENCE: 15

Phe Thr Ser Xaa Tyr Ser Lys Tyr Leu Asp Ser Arg Arg Ala Gln Asp
1               5                   10                  15

Phe Val Gln Trp Leu Xaa Asn Cys
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (19)..(19)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 16
```

```
Phe Thr Ser Xaa Tyr Ser Arg Tyr Leu Asp Ser Arg Arg Ala Gln Asp
1               5                   10                  15

Phe Val Lys Trp Leu Xaa Asn Thr
            20
```

```
<210> SEQ ID NO 17
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (11)..(11)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 17

Phe Thr Ser Xaa Tyr Ser Lys Tyr Leu Asp Cys Arg Arg Ala Gln Asp
1               5                   10                  15

Phe Val Cys Trp Leu Xaa Asn Thr
            20
```

```
<210> SEQ ID NO 18
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 18

Phe Thr Ser Xaa Tyr Ser Lys Tyr Leu Glu Cys Arg Arg Ala Gln Asp
1               5                   10                  15

Phe Val Gln Trp Leu Xaa Asn Thr
```

```
<210> SEQ ID NO 19
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy
      terminal 10 amino acids of Exendin-4

<400> SEQUENCE: 19

Gly Pro Ser Ser Gly Ala Pro Pro Pro Ser
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy
      terminal 8 amino acids of oxyntomodulin

<400> SEQUENCE: 20

Lys Arg Asn Arg Asn Asn Ile Ala
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy 4
      amino acids of oxyntomodulin carboxy terminus

<400> SEQUENCE: 21

Lys Arg Asn Arg
1

<210> SEQ ID NO 22
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (11)..(11)
<223> OTHER INFORMATION: Xaa is Lys, Cys, Orn, homocycstein or acetyl
      phenylalanine
<220> FEATURE:
<221> NAME/KEY: MISC_FEATURE
<222> LOCATION: (19)..(19)
<223> OTHER INFORMATION: Xaa is Lys, Cys, Orn, homocycstein or acetyl
      phenylalanine

<400> SEQUENCE: 22
```

-continued

Phe Thr Ser Arg Tyr Ser Xaa Tyr Leu Asp Xaa Arg Arg Ala Gln Asp
1               5                   10                  15

Phe Val Xaa Trp Leu Met Asn Thr
            20

<210> SEQ ID NO 23
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (16)..(16)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 23

Phe Thr Ser Xaa Tyr Ser Xaa Tyr Leu Asp Ser Arg Arg Ala Gln Xaa
1               5                   10                  15

Phe Val Gln Trp Leu Xaa Asn Thr Gly Pro Ser Ser Gly Ala Pro Pro
            20                  25                  30

Pro Ser

<210> SEQ ID NO 24
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (19)..(19)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (19)..(19)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle -continued

```
<400> SEQUENCE: 24

Phe Thr Ser Xaa Tyr Ser Xaa Tyr Leu Asp Ser Arg Arg Ala Gln Asp
1               5                   10                  15

Phe Val Xaa Trp Leu Xaa Asn Thr Lys Arg Asn Arg Asn Asn Ile Ala
            20                  25                  30

<210> SEQ ID NO 25
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (19)..(19)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (19)..(19)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 25

Phe Thr Ser Xaa Tyr Ser Xaa Tyr Leu Asp Ser Arg Arg Ala Gln Asp
1               5                   10                  15

Phe Val Xaa Trp Leu Xaa Asn Thr Gly Pro Ser Ser Gly Ala Pro Pro
            20                  25                  30

Pro Ser

<210> SEQ ID NO 26
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (16)..(16)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (16)..(16)
<223> OTHER INFORMATION: Pegylation
```

```
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 26

Phe Thr Ser Xaa Tyr Ser Xaa Tyr Leu Asp Ser Arg Arg Ala Gln Xaa
1               5                   10                  15

Phe Val Gln Trp Leu Xaa Asn Thr Lys Arg Asn Arg Asn Asn Ile Ala
            20                  25                  30

<210> SEQ ID NO 27
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (16)..(16)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (16)..(16)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 27

Phe Thr Ser Xaa Tyr Ser Xaa Tyr Leu Asp Ser Arg Arg Ala Gln Xaa
1               5                   10                  15

Phe Val Gln Trp Leu Xaa Asn Thr Lys Arg Asn Arg
            20                  25

<210> SEQ ID NO 28
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (19)..(19)
<223> OTHER INFORMATION: Xaa is Lys, Cys, Orn, homocysteine or acetyl
      phenylalanine
<220> FEATURE:
```

```
<221> NAME/KEY: MISC_FEATURE
<222> LOCATION: (19)..(19)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 28

Phe Thr Ser Xaa Tyr Ser Xaa Tyr Leu Asp Ser Arg Arg Ala Gln Asp
1               5                   10                  15

Phe Val Xaa Trp Leu Xaa Asn Thr Lys Arg Asn Arg
            20                  25

<210> SEQ ID NO 29
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 29

Phe Thr Ser Xaa Tyr Ser Lys Tyr Leu Asp Ser Arg Arg Ala Gln Asp
1               5                   10                  15

Phe Val Gln Trp Leu Xaa Asn Thr Gly Pro Ser Ser Gly Ala Pro Pro
            20                  25                  30

Pro Ser

<210> SEQ ID NO 30
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 30

Phe Thr Ser Xaa Tyr Ser Lys Tyr Leu Asp Ser Arg Arg Ala Gln Asp
```

```
1               5                   10                  15
Phe Val Gln Trp Leu Xaa Asn Thr Lys Arg Asn Arg Asn Asn Ile Ala
            20                  25                  30

<210> SEQ ID NO 31
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 31

Phe Thr Ser Xaa Tyr Ser Lys Tyr Leu Asp Ser Arg Arg Ala Gln Cys
1               5                   10                  15

Phe Val Gln Trp Leu Xaa Asn Thr Lys Arg Asn Arg
            20                  25

<210> SEQ ID NO 32
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 32

His Ser Gln Gly Thr Phe Thr Ser Asp Tyr Ser Lys Tyr Leu Asp Ser
1               5                   10                  15

Cys Arg Ala Gln Asp Phe Val Gln Trp Leu Met Asn Thr
            20                  25

<210> SEQ ID NO 33
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 33

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Ser
            35
```

<210> SEQ ID NO 34
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (24)..(24)
<223> OTHER INFORMATION: 2-butyrolactone bound through thiol group of Cysteine

<400> SEQUENCE: 34

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Asn Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon Analogue
<220> FEATURE:
<221> NAME/KEY: MISC_FEATURE
<222> LOCATION: (24)..(24)
<223> OTHER INFORMATION: Carboxymethyl group bound through thiol group of Cysteine

<400> SEQUENCE: 35

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Asn Thr
            20                  25

<210> SEQ ID NO 36
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy group
<220> FEATURE:
<221> NAME/KEY: MISC_FEATURE
<222> LOCATION: (4)..(4)
<223> OTHER INFORMATION: Xaa is aspartic acid, glutamic acid, cysteic acid or homocysteic acid
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 36

Phe Thr Ser Xaa Tyr Ser Lys Tyr Leu Glu Ser Arg Arg Ala Gln Asp
1               5                   10                  15

Phe Val Gln Trp Leu Xaa Asn Thr

```
                                    20

<210> SEQ ID NO 37
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 37

Phe Thr Ser Asp Tyr Ser Lys Tyr Leu Asp Ser Arg Arg Ala Gln Asp
1               5                   10                  15

Phe Val Gln Trp Leu Xaa Asn Thr
            20

<210> SEQ ID NO 38
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 38

Phe Thr Ser Asp Tyr Ser Lys Tyr Leu Glu Ser Arg Arg Ala Gln Asp
1               5                   10                  15

Phe Val Gln Trp Leu Xaa Asn Thr
            20

<210> SEQ ID NO 39
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
```

```
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Asp, Glu, cysteic acid or
      homocysteic acid
<220> FEATURE:
<221> NAME/KEY: MISC_FEATURE
<222> LOCATION: (24)..(24)
<223> OTHER INFORMATION: Xaa is Thr, Asp, Glu, cysteic acid or
      homocysteic acid

<400> SEQUENCE: 39

Phe Thr Ser Xaa Tyr Ser Lys Tyr Leu Asp Ser Arg Arg Ala Gln Asp
1               5                   10                  15

Phe Val Gln Trp Leu Xaa Xaa Xaa
            20

<210> SEQ ID NO 40
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Glu, cysteic acid, homoglutamic acid or
      homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn or an acidic amino acid
<220> FEATURE:
<221> NAME/KEY: MISC_FEATURE
<222> LOCATION: (24)..(24)
<223> OTHER INFORMATION: Xaa is Thr or an acidic amino acid

<400> SEQUENCE: 40

Phe Thr Ser Xaa Tyr Ser Lys Tyr Leu Xaa Ser Arg Arg Ala Gln Asp
1               5                   10                  15

Phe Val Gln Trp Leu Xaa Xaa Xaa
            20

<210> SEQ ID NO 41
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
```

```
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Glu, cysteic acid, homoglutamic acid or
      homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Asp or Glu
<220> FEATURE:
<221> NAME/KEY: MISC_FEATURE
<222> LOCATION: (24)..(24)
<223> OTHER INFORMATION: Xaa is Thr, glu or Asp

<400> SEQUENCE: 41

Phe Thr Ser Xaa Tyr Ser Lys Tyr Leu Xaa Ser Arg Arg Ala Gln Asp
1               5                   10                  15

Phe Val Gln Trp Leu Xaa Xaa Xaa
            20

<210> SEQ ID NO 42
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Glu, cysteic acid, homoglutamic acid or
      homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn or an acidic amino acid
<220> FEATURE:
<221> NAME/KEY: MISC_FEATURE
<222> LOCATION: (24)..(24)
<223> OTHER INFORMATION: Xaa is Thr or an acidic amino acid

<400> SEQUENCE: 42

Phe Thr Ser Xaa Tyr Ser Lys Tyr Leu Xaa Ser Arg Arg Ala Gln Asp
1               5                   10                  15

Phe Val Gln Trp Leu Xaa Xaa Xaa
```

-continued

```
<210> SEQ ID NO 43
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (11)..(11)
<223> OTHER INFORMATION: 20kDa PEG group attached to Cys at position 11
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn or an acidic amino acid
<220> FEATURE:
<221> NAME/KEY: MISC_FEATURE
<222> LOCATION: (24)..(24)
<223> OTHER INFORMATION: Xaa is Thr or an acidic amino acid

<400> SEQUENCE: 43

Phe Thr Ser Xaa Tyr Ser Lys Tyr Leu Xaa Cys Arg Arg Ala Gln Asp
1               5                   10                  15

Phe Val Gln Trp Leu Xaa Xaa Xaa
            20

<210> SEQ ID NO 44
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
```

```
<222> LOCATION: (16)..(16)
<223> OTHER INFORMATION: 20kDa PEG group attached to Cys at position 16
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn or an acidic amino acid
<220> FEATURE:
<221> NAME/KEY: MISC_FEATURE
<222> LOCATION: (24)..(24)
<223> OTHER INFORMATION: Xaa is Thr or an acidic amino acid

<400> SEQUENCE: 44

Phe Thr Ser Xaa Tyr Ser Lys Tyr Leu Xaa Ser Arg Arg Ala Gln Cys
1               5                   10                  15

Phe Val Gln Trp Leu Xaa Xaa Xaa
            20

<210> SEQ ID NO 45
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (19)..(19)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn or an acidic amino acid
<220> FEATURE:
<221> NAME/KEY: MISC_FEATURE
<222> LOCATION: (24)..(24)
<223> OTHER INFORMATION: Xaa is Thr or an acidic amino acid

<400> SEQUENCE: 45

Phe Thr Ser Xaa Tyr Ser Lys Tyr Leu Xaa Ser Arg Arg Ala Gln Asp
1               5                   10                  15

Phe Val Cys Trp Leu Xaa Xaa Xaa
            20

<210> SEQ ID NO 46
<211> LENGTH: 35
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn or an acidic amino acid
<220> FEATURE:
<221> NAME/KEY: MISC_FEATURE
<222> LOCATION: (24)..(24)
<223> OTHER INFORMATION: Xaa is Thr or an acidic amino acid
<220> FEATURE:
<221> NAME/KEY: MISC_FEATURE
<222> LOCATION: (25)..(25)
<223> OTHER INFORMATION: Xaa is Lys, Cys, Orn, homocycstein or acetyl
      phenylanaline
<220> FEATURE:
<221> NAME/KEY: MISC_FEATURE
<222> LOCATION: (25)..(25)
<223> OTHER INFORMATION: Pegylated

<400> SEQUENCE: 46

Phe Thr Ser Xaa Tyr Ser Lys Tyr Leu Xaa Ser Arg Arg Ala Gln Asp
1               5                   10                  15

Phe Val Gln Trp Leu Xaa Xaa Xaa Xaa Gly Pro Ser Ser Gly Ala Pro
            20                  25                  30

Pro Pro Ser
        35

<210> SEQ ID NO 47
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
```

```
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn or an acidic amino acid
<220> FEATURE:
<221> NAME/KEY: MISC_FEATURE
<222> LOCATION: (24)..(24)
<223> OTHER INFORMATION: Xaa is Thr or an acidic amino acid
<220> FEATURE:
<221> NAME/KEY: MISC_FEATURE
<222> LOCATION: (35)..(35)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (35)..(35)
<223> OTHER INFORMATION: Pegylated

<400> SEQUENCE: 47

Phe Thr Ser Xaa Tyr Ser Lys Tyr Leu Xaa Ser Arg Arg Ala Gln Asp
1               5                   10                  15

Phe Val Gln Trp Leu Xaa Xaa Xaa Gly Pro Ser Ser Gly Ala Pro Pro
            20                  25                  30

Pro Ser Xaa
        35

<210> SEQ ID NO 48
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 48

His Ser Gln Gly Thr Phe Thr Ser Asp Tyr Ser Arg Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Pro Ser
        35

<210> SEQ ID NO 49
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
```

```
<222> LOCATION: (22)..(22)
<223> OTHER INFORMATION: Xaa is Met , Leu or Nle
<220> FEATURE:
<221> NAME/KEY: MISC_FEATURE
<222> LOCATION: (35)..(35)
<223> OTHER INFORMATION: Xaa is Lys, Cys, Orn, homocysteine or acetyl
      phenylalanine
<220> FEATURE:
<221> NAME/KEY: MISC_FEATURE
<222> LOCATION: (35)..(35)
<223> OTHER INFORMATION: Pegylated

<400> SEQUENCE: 49

Phe Thr Ser Xaa Tyr Ser Xaa Tyr Leu Asp Ser Arg Arg Ala Gln Asp
1               5                   10                  15

Phe Val Gln Trp Leu Xaa Asn Thr Gly Pro Ser Ser Gly Ala Pro Pro
                20                  25                  30

Pro Ser Xaa
        35

<210> SEQ ID NO 50
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (1)..(1)
<223> OTHER INFORMATION: N-terminal amino group replaced with hydroxy
      group

<400> SEQUENCE: 50

Phe Thr Ser Glu Tyr Ser Lys Tyr Leu Asp Ser Arg Arg Ala Gln Asp
1               5                   10                  15

Phe Val Gln Trp Leu Met Asn Thr
                20

<210> SEQ ID NO 51
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 51

Tyr Ser Lys Tyr Leu Asp Ser Arg Arg Ala Gln Asp Phe Val Gln Trp
1               5                   10                  15

Leu Met Asn Thr
        20

<210> SEQ ID NO 52
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
```

```
<223> OTHER INFORMATION: Xaa is Homocysteic acid

<400> SEQUENCE: 52

Phe Thr Ser Xaa Tyr Ser Lys Tyr Leu Asp Ser Arg Arg Ala Gln Asp
1               5                   10                  15

Phe Val Gln Trp Leu Met Asn Thr
            20

<210> SEQ ID NO 53
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy
      terminal 10 amino acids of Exendin-4
<220> FEATURE:
<221> NAME/KEY: MISC_FEATURE
<222> LOCATION: (11)..(11)
<223> OTHER INFORMATION: Xaa is Lys, Cys, Orn, homocysteine or acetyl
      phenylalanine

<400> SEQUENCE: 53

Gly Pro Ser Ser Gly Ala Pro Pro Pro Ser Xaa
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Thr is linked to Phenyl Lactic Acid (PLA) via
      ester bond

<400> SEQUENCE: 54

His Ser Gln Gly Thr
1               5

<210> SEQ ID NO 55
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Thr is linked to Phenyl Lactic Acid (PLA) via
      ester bond

<400> SEQUENCE: 55

Ser Gln Gly Thr
1

<210> SEQ ID NO 56
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Thr is linked to Phenyl Lactic Acid (PLA) via
``` ester bond

<400> SEQUENCE: 56

Gln Gly Thr
1

<210> SEQ ID NO 57
<211> LENGTH: 2
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Thr is linked to Phenyl Lactic Acid (PLA) via
      ester bond

<400> SEQUENCE: 57

Gly Thr
1

<210> SEQ ID NO 58
<211> LENGTH: 1
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Thr is linked to Phenyl Lactic Acid (PLA) via
      ester bond

<400> SEQUENCE: 58

Thr
1

<210> SEQ ID NO 59
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of His,
      D-histidine, alpha, alpha-dimethyl imidiazole acetic acid (DMIA),
      N-methyl histidine, alpha-methyl histidine, imidazole acetic acid,
      desaminohistidine, hydroxyl-histidine, acetyl-histidine and
<220> FEATURE:
<221> NAME/KEY: MISC_FEATURE
<222> LOCATION: (2)..(2)
<223> OTHER INFORMATION: Xaa is selected from a group consisting of Ser,
      D-serine, D-alanine, Val, Gly, N-methyl serine, N-methyl alanine,
      and aminoisobutyric acid (AIB)
<220> FEATURE:
<221> NAME/KEY: MISC_FEATURE
<222> LOCATION: (3)..(3)
<223> OTHER INFORMATION: Xaa is selected from a group consisting of Glu
      or Gln
<220> FEATURE:
<221> NAME/KEY: MISC_FEATURE
<222> LOCATION: (5)..(5)
<223> OTHER INFORMATION: Thr is linked to Phenyl Lactic Acid (PLA) via
      ester bond

<400> SEQUENCE: 59

Xaa Xaa Xaa Gly Thr
1               5

```
<210> SEQ ID NO 60
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Ser,
      D-serine, D-alanine, Val, Gly, N-methyl serine, N-methyl alanine,
      and aminoisobutyric acid (AIB)
<220> FEATURE:
<221> NAME/KEY: MISC_FEATURE
<222> LOCATION: (2)..(2)
<223> OTHER INFORMATION: Xaa is selected from a group consisting of Glu
      or Gln
<220> FEATURE:
<221> NAME/KEY: MISC_FEATURE
<222> LOCATION: (4)..(4)
<223> OTHER INFORMATION: Thr is linked to Phenyl Lactic Acid (PLA) via
      ester bond

<400> SEQUENCE: 60

Xaa Xaa Gly Thr
1

<210> SEQ ID NO 61
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Glu
      and Gln
<220> FEATURE:
<221> NAME/KEY: MISC_FEATURE
<222> LOCATION: (3)..(3)
<223> OTHER INFORMATION: Thr is linked to Phenyl Lactic Acid (PLA) via
      ester bond

<400> SEQUENCE: 61

Xaa Gly Thr
1

<210> SEQ ID NO 62
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AL
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (24)..(24)
<223> OTHER INFORMATION: C-terminal alpha carboxylate optionally
      replaced with amide

<400> SEQUENCE: 62

Phe Thr Ser Asp Tyr Ser Lys Tyr Leu Asp Ser Arg Arg Ala Gln Asp
1               5                   10                  15

Phe Val Gln Trp Leu Met Asp Thr
```

```
<210> SEQ ID NO 63
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AM
<220> FEATURE:
<221> NAME/KEY: MISC_FEATURE
<222> LOCATION: (28)..(28)
<223> OTHER INFORMATION: C-terminal alpha carboxylate optionally
      replaced with amide

<400> SEQUENCE: 63

Ser Gln Gly Thr Phe Thr Ser Glu Tyr Ser Lys Tyr Leu Asp Ser Arg
1               5                   10                  15

Arg Ala Gln Asp Phe Val Gln Trp Leu Met Asn Thr
            20                  25

<210> SEQ ID NO 64
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AN
<220> FEATURE:
<221> NAME/KEY: MISC_FEATURE
<222> LOCATION: (1)..(1)
<223> OTHER INFORMATION: Alpha amine of Thr is peptide bonded to SEQ ID
      NO: 55 via carboxylate of Phenyl Lactic Acid (PLA)
<220> FEATURE:
<221> NAME/KEY: MISC_FEATURE
<222> LOCATION: (23)..(23)
<223> OTHER INFORMATION: C-terminal alpha carboxylate replaced with
      amide

<400> SEQUENCE: 64

Thr Ser Glu Tyr Ser Lys Tyr Leu Asp Ser Arg Arg Ala Gln Asp Phe
1               5                   10                  15

Val Gln Trp Leu Met Asn Thr
            20

<210> SEQ ID NO 65
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AO
<220> FEATURE:
<221> NAME/KEY: MISC_FEATURE
<222> LOCATION: (1)..(1)
<223> OTHER INFORMATION: Alpha amine of Thr is peptide bonded to SEQ ID
      NO: 54 via carboxylate of Phenyl Lactic Acid (PLA)
<220> FEATURE:
<221> NAME/KEY: MISC_FEATURE
<222> LOCATION: (23)..(23)
<223> OTHER INFORMATION: C-terminal alpha carboxylate replaced with
      amide

<400> SEQUENCE: 65

Thr Ser Glu Tyr Ser Lys Tyr Leu Asp Ser Arg Arg Ala Gln Asp Phe
```

```
1               5                   10                  15
Val Gln Trp Leu Met Asn Thr
            20

<210> SEQ ID NO 66
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AQ
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(11)
<223> OTHER INFORMATION: Xaa is amino isobutyric acid

<400> SEQUENCE: 66

Phe Thr Ser Asp Tyr Ser Lys Tyr Leu Asp Xaa Arg Arg Ala Gln Asp
1               5                   10                  15

Phe Val Gln Trp Leu Met Asn Thr
            20

<210> SEQ ID NO 67
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AT
<220> FEATURE:
<221> NAME/KEY: MISC_FEATURE
<222> LOCATION: (1)..(1)
<223> OTHER INFORMATION: N-terminal amino group replaced with hydroxy
      group

<400> SEQUENCE: 67

Phe Thr Ser Asp Tyr Ser Lys Tyr Leu Asp Glu Arg Arg Ala Gln Asp
1               5                   10                  15

Phe Val Gln Trp Leu Met Asn Thr
            20

<210> SEQ ID NO 68
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of His,
      D-histidine, alpha, alpha-dimethyl imidiazole acetic acid (DMIA),
      N-methyl histidine, alpha-methyl histidine, imidazole acetic acid,
      desaminohistidine, hydroxyl-histidine, acetyl-histidine and
<220> FEATURE:
<221> NAME/KEY: MISC_FEATURE
<222> LOCATION: (2)..(2)
<223> OTHER INFORMATION: Xaa is selected from a group consisting of Ser,
      D-serine, D-alanine, Val, Gly, N-methyl serine, N-methyl alanine,
      and aminoisobutyric acid (AIB)
<220> FEATURE:
<221> NAME/KEY: MISC_FEATURE
```

```
<222> LOCATION: (3)..(3)
<223> OTHER INFORMATION: Xaa is selected from a group consisting of Glu
      or Gln

<400> SEQUENCE: 68

Xaa Xaa Xaa Thr Gly Phe
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Ser,
      D-serine, D-alanine, Val, Gly, N-methyl serine, N-methyl alanine,
      and aminoisobutyric acid (AIB)
<220> FEATURE:
<221> NAME/KEY: MISC_FEATURE
<222> LOCATION: (2)..(2)
<223> OTHER INFORMATION: Xaa is selected from a group consisting of Glu
      or Gln

<400> SEQUENCE: 69

Xaa Xaa Thr Gly Phe
1               5

<210> SEQ ID NO 70
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Glu
      or Gln

<400> SEQUENCE: 70

Xaa Thr Gly Phe
1

<210> SEQ ID NO 71
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (24)..(24)
<223> OTHER INFORMATION: C-terminal alpha carboxylate optionally
      replaced with an amide

<400> SEQUENCE: 71

Phe Thr Ser Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 72
```

```
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, D9]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 72

Phe Thr Ser Asp Tyr Ser Lys Tyr Leu Asp Ser Arg Arg Ala Gln Asp
1               5                   10                  15

Phe Val Gln Trp Leu Met Asn Thr
            20

<210> SEQ ID NO 73
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, D9]Glucagon(aa6-29)-COOH
<220> FEATURE:
<221> NAME/KEY: MISC_FEATURE
<222> LOCATION: (1)..(1)
<223> OTHER INFORMATION: N-terminal amino group replaced with hydroxy
      group

<400> SEQUENCE: 73

Phe Thr Ser Asp Tyr Ser Lys Tyr Leu Asp Ser Arg Arg Ala Gln Asp
1               5                   10                  15

Phe Val Gln Trp Leu Met Asn Thr
            20

<210> SEQ ID NO 74
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, E9]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 74

Phe Thr Ser Glu Tyr Ser Lys Tyr Leu Asp Ser Arg Arg Ala Gln Asp
1               5                   10                  15

Phe Val Gln Trp Leu Met Asn Thr
            20
```

<210> SEQ ID NO 75
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, hCys(SO3)9]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy group
<220> FEATURE:
<221> NAME/KEY: MISC_FEATURE
<222> LOCATION: (4)..(4)
<223> OTHER INFORMATION: Xaa is homocysteic acid
<220> FEATURE:
<221> NAME/KEY: MISC_FEATURE
<222> LOCATION: (24)..(24)
<223> OTHER INFORMATION: C-terminal alpha carboxylate replaced with amide

<400> SEQUENCE: 75

Phe Thr Ser Xaa Tyr Ser Lys Tyr Leu Asp Ser Arg Arg Ala Gln Asp
1               5                   10                  15

Phe Val Gln Trp Leu Met Asn Thr
            20

<210> SEQ ID NO 76
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, D9, D28] Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy group
<220> FEATURE:
<221> NAME/KEY: MISC_FEATURE
<222> LOCATION: (24)..(24)
<223> OTHER INFORMATION: C-terminal alpha carboxylate replaced with amide

<400> SEQUENCE: 76

Phe Thr Ser Asp Tyr Ser Lys Tyr Leu Asp Ser Arg Arg Ala Gln Asp
1               5                   10                  15

Phe Val Gln Trp Leu Met Asp Thr
            20

<210> SEQ ID NO 77
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, E9]Glucagon (aa6-29+CEX)-NH2
<220> FEATURE:
<221> NAME/KEY: MISC_FEATURE
<222> LOCATION: (1)..(1)
<223> OTHER INFORMATION: N-terminal amino group replaced with hydroxy group
<220> FEATURE:

<221> NAME/KEY: MISC_FEATURE
<222> LOCATION: (34)..(34)
<223> OTHER INFORMATION: C-terminal alpha carboxylate replaced with
      amide

<400> SEQUENCE: 77

Phe Thr Ser Glu Tyr Ser Lys Tyr Leu Asp Ser Arg Arg Ala Gln Asp
1               5                   10                  15

Phe Val Gln Trp Leu Met Asn Thr Gly Pro Ser Ser Gly Ala Pro Pro
            20                  25                  30

Pro Ser

<210> SEQ ID NO 78
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [Ac-PLA6, E9]Glucagon(aa6-29)-NH2
<220> FEATURE:
<221> NAME/KEY: MISC_FEATURE
<222> LOCATION: (1)..(1)
<223> OTHER INFORMATION: Xaa is acylated phenyl lactic acid (PLA)
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 78

Xaa Thr Ser Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 79
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA5 E9]Glucagon(aa5-29)-NH2
<220> FEATURE:
<221> NAME/KEY: MISC_FEATURE
<222> LOCATION: (1)..(1)
<223> OTHER INFORMATION: Xaa is phenyl lactic acid (PLA)
<220> FEATURE:
<221> NAME/KEY: MISC_FEATURE
<222> LOCATION: (25)..(25)
<223> OTHER INFORMATION: C-terminal alpha carboxylate replaced with
      amide

<400> SEQUENCE: 79

Xaa Phe Thr Ser Glu Tyr Ser Lys Tyr Leu Asp Ser Arg Arg Ala Gln
1               5                   10                  15

Asp Phe Val Gln Trp Leu Met Asn Thr
            20                  25

<210> SEQ ID NO 80
<211> LENGTH: 26
<212> TYPE: PRT
<213> ORGANISM: Artificial Sequence
<220> FEATURE:
<223> OTHER INFORMATION: Synthetic polypeptide
<220> FEATURE:

```
<221> NAME/KEY: MISC_FEATURE
<223> OTHER INFORMATION: [PLA4, E9]Glucagon(aa4-29)-NH2
<220> FEATURE:
<221> NAME/KEY: MISC_FEATURE
<222> LOCATION: (1)..(1)
<223> OTHER INFORMATION: Xaa is phenyl lactic acid (PLA)
<220> FEATURE:
<221> NAME/KEY: MISC_FEATURE
<222> LOCATION: (26)..(26)
<223> OTHER INFORMATION: C-terminal alpha carboxylate replaced with
      amide

<400> SEQUENCE: 80

Xaa Thr Phe Thr Ser Glu Tyr Ser Lys Tyr Leu Asp Ser Arg Arg Ala
1               5                   10                  15

Gln Asp Phe Val Gln Trp Leu Met Asn Thr
            20                  25

<210> SEQ ID NO 81
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, C8(20kDaPEG), E9]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (3)..(3)
<223> OTHER INFORMATION: Covalently bound to a 20 kDa PEG
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 81

Phe Thr Cys Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 82
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, E9, C11(20kDaPEG)]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (6)..(6)
<223> OTHER INFORMATION: Covalently bound to a 20 kDa PEG
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 82
```

Phe Thr Ser Glu Tyr Cys Lys Tyr Leu Asp Ser Arg Arg Ala Gln Asp
1               5                   10                  15

Phe Val Gln Trp Leu Met Asn Thr
            20

<210> SEQ ID NO 83
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, E9, C24(20kDaPEG)]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (19)..(19)
<223> OTHER INFORMATION: Covalently bound to a 20 kDa PEG
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 83

Phe Thr Ser Glu Tyr Ser Lys Tyr Leu Asp Ser Arg Arg Ala Gln Asp
1               5                   10                  15

Phe Val Cys Trp Leu Met Asn Thr
            20

<210> SEQ ID NO 84
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, C8(1.2kDaPEG), E9]Glucagon(aa6-29) -NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (3)..(3)
<223> OTHER INFORMATION: Covalently bound to a 1.2 kDa PEG
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 84

Phe Thr Cys Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 85
<211> LENGTH: 24
<212> TYPE: PRT
<213> ORGANISM: Artificial Sequence
<220> FEATURE:

<223> OTHER INFORMATION: Synthetic polypeptide
<220> FEATURE:
<221> NAME/KEY: MISC_FEATURE
<223> OTHER INFORMATION: [PLA6, C8(5kDaPEG), E9]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (3)..(3)
<223> OTHER INFORMATION: Covalently bound to a 5 kDa PEG
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 85

Phe Thr Cys Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 86
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, C8(20kDaPEG), E9]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (3)..(3)
<223> OTHER INFORMATION: Covalently bound to a 20 kDa PEG
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 86

Phe Thr Cys Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 87
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, E9 ,C24(1.2kDaPEG)]Glucagon(aa6-29)-NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (19)..(19)
<223> OTHER INFORMATION: Covalently bound to a 1.2 kDa PEG

```
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 87

Phe Thr Ser Glu Tyr Ser Lys Tyr Leu Asp Ser Arg Arg Ala Gln Asp
1               5                   10                  15

Phe Val Cys Trp Leu Met Asn Thr
            20

<210> SEQ ID NO 88
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: [PLA6, E9, C24(20kDaPEG)]Glucagon(aa6-29) -NH2
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (19)..(19)
<223> OTHER INFORMATION: Covalently bound to a 20 kDa PEG
<220> FEATURE:
<221> NAME/KEY: MISC_FEATURE
<222> LOCATION: (24)..(24)
<223> OTHER INFORMATION: C-terminal alpha carboxylate replaced with
      amide

<400> SEQUENCE: 88

Phe Thr Ser Glu Tyr Ser Lys Tyr Leu Asp Ser Arg Arg Ala Gln Asp
1               5                   10                  15

Phe Val Cys Trp Leu Met Asn Thr
            20
```